(12) United States Patent
Hirata et al.

(10) Patent No.: US 11,269,263 B2
(45) Date of Patent: Mar. 8, 2022

(54) BISCHLOROFORMATE COMPOSITION, BISCHLOROFORMATE COMPOSITION PRODUCTION METHOD, BISCHLOROFORMATE COMPOSITION-CONTAINING SOLUTION, POLYCARBONATE RESIN, POLYCARBONATE RESIN PRODUCTION METHOD, COATING LIQUID, ELECTROPHOTOGRAPHIC PHOTORECEPTOR, AND ELECTROPHOTOGRAPHIC DEVICE

(71) Applicant: IDEMITSU KOSAN CO., LTD., Tokyo (JP)

(72) Inventors: Kengo Hirata, Chiba (JP); Takaaki Hikosaka, Chiba (JP); Hironobu Morishita, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 16/062,442

(22) PCT Filed: Dec. 16, 2016

(86) PCT No.: PCT/JP2016/087692
§ 371 (c)(1),
(2) Date: Jun. 14, 2018

(87) PCT Pub. No.: WO2017/104849
PCT Pub. Date: Jun. 22, 2017

(65) Prior Publication Data
US 2018/0364598 A1 Dec. 20, 2018

(30) Foreign Application Priority Data
Dec. 16, 2015 (JP) .............................. JP2015-245711

(51) Int. Cl.
*G03G 5/05* (2006.01)
*C07C 69/96* (2006.01)
(Continued)

(52) U.S. Cl.
CPC ............... *G03G 5/05* (2013.01); *C07C 68/02* (2013.01); *C07C 69/96* (2013.01); *C08G 64/06* (2013.01);
(Continued)

(58) Field of Classification Search
CPC ........ G03G 5/05; G03G 5/0564; C08L 69/00; C07C 68/02; C07C 69/96; C08G 64/26
See application file for complete search history.

(56) References Cited

U.S. PATENT DOCUMENTS

| | | | |
|---|---|---|---|
| 5,604,063 A * | 2/1997 | Endo | G03G 5/0564 430/58.4 |
| 8,344,092 B2 | 1/2013 | Hikosaka et al. | |

(Continued)

FOREIGN PATENT DOCUMENTS

| | | |
|---|---|---|
| CN | 102453251 A | 5/2012 |
| CN | 102803198 A | 11/2012 |

(Continued)

OTHER PUBLICATIONS

English Translation of the International Preliminary Report on Patentability, dated Jun. 19, 2018, from PCT application PCT/JP2016/087692.

(Continued)

*Primary Examiner* — Duane Smith
*Assistant Examiner* — Nicholas E Brown
(74) *Attorney, Agent, or Firm* — Millen, White, Zelano & Branigan, PC; Ryan Pool

(57) ABSTRACT

A bischloroformate composition is represented by a formula (1) below, contains a plurality of Ar components, and has an (Continued)

average number of monomer units (m1), which is calculated by an expression (Numerical Expression 1) below, ranging from 1.0 to 1.99. The plurality of Ar components are each independently $Ar_1$ or $Ar_2$. The plurality of Ar components include at least one $Ar_1$ and at least one $Ar_2$. $Ar_1$ is a group represented by a formula (2) below. $Ar_2$ is a group represented by a formula (3) below. A molar composition ratio represented by $Ar_1/(Ar_1+Ar_2)$ ranges from 45 mol % to 99 mol %.

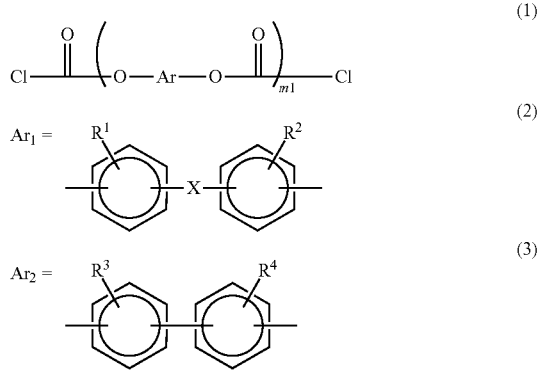

average number of monomer units (m1)=1+(Mav−M1)/M2 (Numerical Expression 1)

16 Claims, 2 Drawing Sheets

(51) Int. Cl.
```
C08G 64/06    (2006.01)
C08G 64/18    (2006.01)
C08L 69/00    (2006.01)
C08G 64/26    (2006.01)
C07C 68/02    (2006.01)
```
(52) U.S. Cl.
CPC ............ *C08G 64/18* (2013.01); *C08G 64/26* (2013.01); *C08L 69/00* (2013.01); *G03G 5/0564* (2013.01)

(56) References Cited

U.S. PATENT DOCUMENTS

| | | | |
|---|---|---|---|
| 8,470,957 | B2 | 6/2013 | Hikosaka et al. |
| 9,188,887 | B2 | 11/2015 | Hirata et al. |
| 9,458,291 | B2 | 10/2016 | Hirata et al. |
| 9,529,285 | B2 | 12/2016 | Hirata et al. |
| 9,551,946 | B2 | 1/2017 | Hirata et al. |
| 10,241,427 | B2 * | 3/2019 | Hirata .................... C08G 64/14 |
| 2012/0101292 | A1 | 4/2012 | Hikosaka et al. |
| 2013/0066037 | A1 | 3/2013 | Hikosaka et al. |
| 2013/0337373 | A1 * | 12/2013 | Hirata .................... C08G 63/64 |
| | | | 430/96 |
| 2014/0363760 | A1 | 12/2014 | Hirata |
| 2015/0010859 | A1 | 1/2015 | Hirata et al. |
| 2016/0116854 | A1 | 4/2016 | Hirata et al. |
| 2017/0075237 | A1 | 3/2017 | Hirata et al. |

FOREIGN PATENT DOCUMENTS

| | | |
|---|---|---|
| CN | 103391958 A | 11/2013 |
| CN | 103998486 A | 8/2014 |
| CN | 103998487 A | 8/2014 |
| JP | H11172003 A | 6/1999 |
| JP | 2005139339 A | 6/2005 |
| JP | 2011006367 A | 1/2011 |
| JP | 2011026308 A | 2/2011 |
| JP | 2012051983 A | 3/2012 |
| WO | 2010150888 A1 | 12/2010 |
| WO | 2012115088 A1 | 8/2012 |
| WO | 2013099965 A1 | 7/2013 |
| WO | 2013125229 A1 | 8/2013 |
| WO | 2014192633 A1 | 12/2014 |
| WO | 2015174533 A1 | 11/2015 |
| WO | WO-2015174533 A1 * | 11/2015 ........... G03G 5/0564 |

OTHER PUBLICATIONS

English Translation of the International Search Report for PCT/JP2016/087692 dated Mar. 14, 2017.
English Abstract of JPH11172003, Publication Date: Jun. 29, 1999.
English Abstract of JP2005139339, Publication Date: Jun. 2, 2005.
English Abstract of JP2012051983, Publication Date: Mar. 15, 2012.
Office Action issued in corresponding Chinese patent application No. 201680072720.6 dated Aug. 26, 2020 (received an Sep. 3, 2020) pp. 1-13.

* cited by examiner

BISCHLOROFORMATE COMPOSITION, BISCHLOROFORMATE COMPOSITION PRODUCTION METHOD, BISCHLOROFORMATE COMPOSITION-CONTAINING SOLUTION, POLYCARBONATE RESIN, POLYCARBONATE RESIN PRODUCTION METHOD, COATING LIQUID, ELECTROPHOTOGRAPHIC PHOTORECEPTOR, AND ELECTROPHOTOGRAPHIC DEVICE

TECHNICAL FIELD

The present invention relates to a bischloroformate composition, a production method of the bischloroformate composition, a bischloroformate-composition-containing solution, a polycarbonate resin, a production method of the polycarbonate resin, a coating liquid, an electrophotographic photoreceptor, and an electrophotographic device.

BACKGROUND ART

Typical examples of known phenols include phenol, biphenol composed of two phenols directly bonded to each other, and bisphenol composed of two phenols bonded to each other via a linking group. It has been suggested that phenolic hydroxyl groups of the above phenols are chloroformatized to synthesize chloroformate compounds.

Patent Literature 1 discloses a method of producing a bischloroformate compound from a material including at least a divalent phenol compound and a phosgene compound using a hydrophobic organic solvent, particularly disclosing a method of bischloroformatizing dihydric phenol compounds such as biphenol and bisphenol.

Further, a polycarbonate resin produced from the above chloroformate compound is excellent in mechanical properties, thermal properties and electrical properties, so that it is usable as a binder resin for an organic electrophotographic photoreceptor.

Patent Literature 2 discloses a polycarbonate resin produced from a bischloroformate compound having a biphenol skeleton with an average number of monomer units ranging from 1.0 to 1.3, the polycarbonate resin being reported to have good mechanical properties.

CITATION LIST

Patent Literatures

Patent Literature 1: International Publication No. WO 2010/150888
Patent Literature 2: International Publication No. WO 2014/192633

SUMMARY OF THE INVENTION

Problems to be Solved by the Invention

Unfortunately, although the technique of Patent Literature 1 enables bischloroformatizing dihydric phenol compounds such as biphenol or bisphenol, the bischloroformate compound having a biphenol skeleton, such as 3,3'-dimethyl-4,4'-dihydroxybiphenyl, is less soluble in a solvent, lowering the solution stability. The technique of Patent Literature 2 has a problem similar to that of Patent Literature 1. Specifically, in producing a polycarbonate resin consisting mainly of a biphenol skeleton from a bischloroformate compound having a biphenol skeleton, the bischloroformate compound is less soluble in a solvent, lowering the solution stability.

Such biphenol-based bischloroformate compounds produced by the typical methods are less soluble in a solvent and thus lower the solution stability, for instance, when stored in the form of a solution for a long period.

Further, resins produced from the above materials (biphenols) are structurally unstable, resulting in a wide variety of structures of the resin. The physical properties of the resins are thus uncontrollable. Moreover, such a resin produced by the typical method exhibits an insufficient wear resistance due to, for instance, poor copolymerization of wear resistance components.

Although polycarbonate resins are required to be well soluble under a wide range of conditions to widen conditions for application of wet molding, some resins produced by the typical techniques are substandard in solubility.

An object of the invention is to provide a bischloroformate composition improved in solvent solubility and, consequently, in solution stability, a production method of the bischloroformate composition, and a bischloroformate-composition-containing solution.

Another object of the invention is to provide a well-soluble polycarbonate resin excellent in wear resistance, a production method of the polycarbonate resin, coating liquid and electrophotographic photoreceptor produced from the polycarbonate resin, and an electrophotographic device including the electrophotographic photoreceptor.

Means for Solving the Problems

According to an aspect of the invention, a bischloroformate composition that is represented by a formula (1) below, contains a plurality of Ar components, and has an average number of monomer units (m1), which is calculated by an expression (Numerical Expression 1) below, ranging from 1.0 to 1.99, in which the plurality of Ar components are each independently $Ar_1$ or $Ar_2$, the plurality of Ar components include at least one $Ar_1$ and at least one $Ar_2$, $Ar_1$ is a group represented by a formula (2) below and $Ar_2$ is a group represented by a formula (3) below, and a molar composition ratio represented by $Ar_1/(Ar_1+Ar_2)$ ranges from 45 mol % to 99 mol %.

[Formula 1]

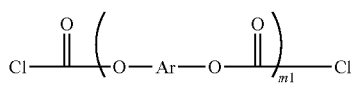
(1)

In the formula (1), Ar is the group represented by the formula (2) below or the formula (3) below and m1 represents the average number of monomer units of the bischloroformate composition.

[Formula 2]

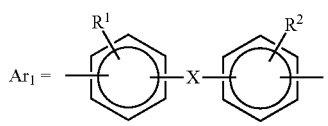
(2)

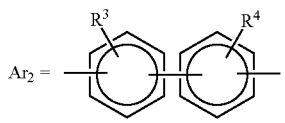

(3)

$R^1$ and $R^2$ in the formula (2) are each independently a hydrogen atom or a substituent, $R^1$ and $R^2$ as substituents being each independently selected from the group consisting of a trifluoromethyl group and an alkyl group having 1 to 3 carbon atoms;

X is selected from the group consisting of —O—, —CO—, —S—, —SO$_2$—, —CR$^5$R$^6$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below;

$R^5$ and $R^6$ are each independently a hydrogen atom or a substituent, $R^5$ and $R^6$ as substituents being each independently selected from the group consisting of an alkyl group having 1 to 5 carbon atoms, a trifluoromethyl group, and a substituted or unsubstituted aryl group having 6 to 12 carbon atoms; and $R^3$ and $R^4$ in the formula (3) are each independently selected from the group consisting of a perfluoroalkyl having 1 to 3 carbon atoms and an alkyl group having 1 to 3 carbon atoms.

[Formula 3]

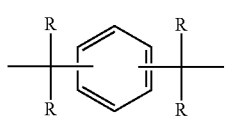

(100)

In the formula (100), R are each independently an aliphatic hydrocarbon group having 1 to 6 carbon atoms.

[Numerical Expression 1]

average number of monomer units(*m*1)=1+(*Mav*−*M*1)/*M*2      (Numerical Expression 1)

In the expression (Numerical Expression 1):
May represents (2×1000/(CF number));
M1 represents an average molecular weight of a bischloroformate compound present at the ratio represented by Ar$_1$/(Ar$_1$+Ar$_2$) in the bischloroformate composition with the average number of monomer units (m1) being 1.0;
M2 represents (M1−Y);
the CF number [a mole number of a chlorine atom/kg] is (CF value/concentration) of a bischloroformate composition solution produced by fully dissolving the bischloroformate composition in an organic solvent;
the CF value [N] is the mole number of the chlorine atom in the bischloroformate compound contained in 1 L of the bischloroformate composition solution;
the concentration [kg/L] is an amount of a solid content obtained by condensing 1 L of the bischloroformate composition solution; and Y is a total atom weight of two chlorine atoms, one oxygen atom and one carbon atom which are desorbed at polycondensation of the bischloroformate compound and a phenol compound.

In a production method of the bischloroformate composition according to another aspect of the invention, at least a hydrophobic organic solvent, a bisphenol compound represented by a formula (4) below, a biphenol compound represented by a formula (5) below, and a phosgene compound are used.

[Formula 4]

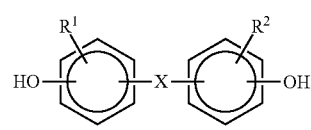

(4)

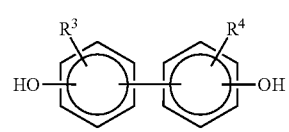

(5)

$R^1$, $R^2$ and X in the formula (4) respectively mean the same as $R^1$, $R^2$ and X in the formula (2); and $R^3$ and $R^4$ in the formula (5) respectively mean the same as $R^3$ and $R^4$ in the formula (3).

According to still another aspect of the invention, a bischloroformate-composition-containing solution contains the bischloroformate composition and a solvent.

In a production method of a polycarbonate resin according to yet another aspect of the invention, at least the bischloroformate composition and a biphenol compound represented by a formula (5) below are used.

[Formula 5]

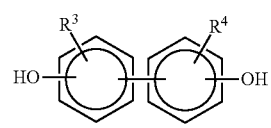

(5)

In the formula (5), $R^3$ and $R^4$ respectively mean the same as $R^3$ and $R^4$ in the formula (3).

According to a further aspect of the invention, a production method of a polycarbonate resin, in which at least the bischloroformate composition, an organic solvent, an alkali solution, and a dihydric phenol compound are used, includes mixing the organic layer and an aqueous layer to cause interfacial polycondensation.

According to a still further aspect of the invention, a polycarbonate resin that is represented by a formula (A1) below and has a molar composition ratio represented by Ar$_2$/(Ar$_1$+Ar$_2$) ranging from 40 mol % to 75 mol %.

[Formula 6]

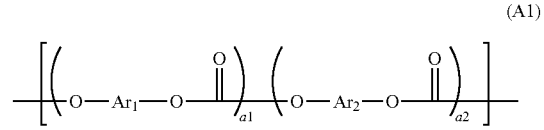

(A1)

In the formula (A1): $Ar_1$ is a group represented by a formula (2) below; $Ar_2$ is a group represented by a formula (3) below; a1 represents an average chain length of the component $Ar_1$; a2 represents an average chain length of the component $Ar_2$; and a1 and a2 are each independently more than 1.0 but not more than 2.7.

[Formula 7]

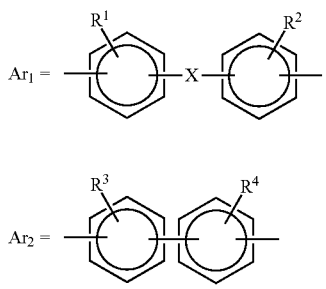

$R^1$ and $R^2$ in the formula (2) are each independently a hydrogen atom or a substituent, $R^1$ and $R^2$ as substituents being each independently selected from the group consisting of a trifluoromethyl group and an alkyl group having 1 to 3 carbon atoms;

X is selected from the group consisting of —O—, —CO—, —S—, —SO$_2$—, —CR$^5$R$^6$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below;

$R^5$ and $R^6$ are each independently a hydrogen atom or a substituent, $R^5$ and $R^6$ as substituents being each independently selected from the group consisting of an alkyl group having 1 to 5 carbon atoms, a trifluoromethyl group, and a substituted or unsubstituted aryl group having 6 to 12 carbon atoms; and $R^3$ and $R^4$ in the formula (3) are each independently selected from the group consisting of a perfluoroalkyl having 1 to 3 carbon atoms and an alkyl group having 1 to 3 carbon atoms.

[Formula 8]

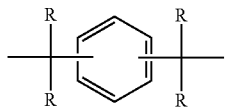

In the formula (100), R are each independently an aliphatic hydrocarbon group having 1 to 6 carbon atoms.

According to a yet further aspect of the invention, a polycarbonate resin that is represented by a formula (A2) below and has a molar composition ratio represented by $Ar_2/(Ar_1+Ar_2)$ ranging from 40 mol % to 75 mol %.

[Formula 9]

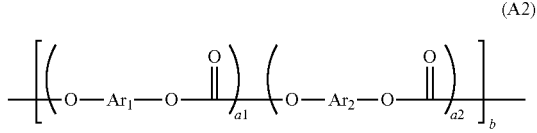

In the formula (A2): $Ar_i$ is a group represented by a formula (2) below; $Ar_2$ is a group represented by a formula (3) below; a1 represents an average chain length of the component $Ar_1$; a2 represents an average chain length of the component $Ar_2$; a1 and a2 are each independently more than 1.0 but not more than 2.7; b represents the number of repetition of a unit in a square bracket; and (a1+a2)×b, which represents an average number of repetition of the resin, is a value of 30 to 300.

[Formula 10]

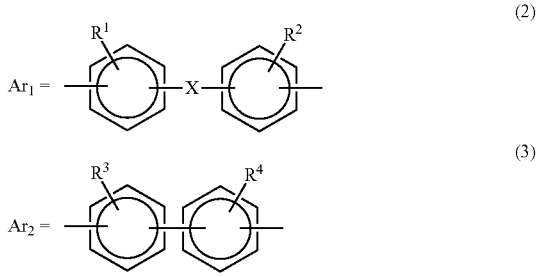

$R^1$ and $R^2$ in the formula (2) are each independently a hydrogen atom or a substituent, $R^1$ and $R^2$ as substituents being each independently selected from the group consisting of a trifluoromethyl group and an alkyl group having 1 to 3 carbon atoms;

X is selected from the group consisting of —O—, —CO—, —S—, —SO$_2$—, —CR$^5$R$^6$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below;

$R^5$ and $R^6$ are each independently a hydrogen atom or a substituent, $R^5$ and $R^6$ as substituents being each independently selected from the group consisting of an alkyl group having 1 to 5 carbon atoms, a trifluoromethyl group, and a substituted or unsubstituted aryl group having 6 to 12 carbon atoms; and $R^3$ and $R^4$ in the formula (3) are each independently selected from the group consisting of a perfluoroalkyl having 1 to 3 carbon atoms and an alkyl group having 1 to 3 carbon atoms.

[Formula 11]

In the formula (100), R are each independently an aliphatic hydrocarbon group having 1 to 6 carbon atoms.

According to a yet further aspect of the invention, a coating liquid includes the polycarbonate resin and an organic solvent.

According to a yet further aspect of the invention, an electrophotographic photoreceptor includes the polycarbonate resin.

According to a yet further aspect of the invention, an electrophotographic photoreceptor includes a substrate and a photosensitive layer on the substrate, the photosensitive layer containing the polycarbonate resin.

According to a yet further aspect of the invention, an electrophotographic device including the electrophotographic photoreceptor.

According to the above aspects of the invention, a bischloroformate composition improved in solvent solubility and, consequently, in solution stability, a production method of the bischloroformate composition, and a bischloroformate-composition-containing solution can be provided. Further, according to the above aspects of the invention, a well-soluble polycarbonate resin excellent in wear resistance, a production method of the polycarbonate resin, coating liquid and electrophotographic photoreceptor produced from the polycarbonate resin, and an electrophotographic device including the electrophotographic photoreceptor can be provided.

BRIEF DESCRIPTION OF DRAWING(S)

DESCRIPTION OF EMBODIMENT(S)

Figure 1:
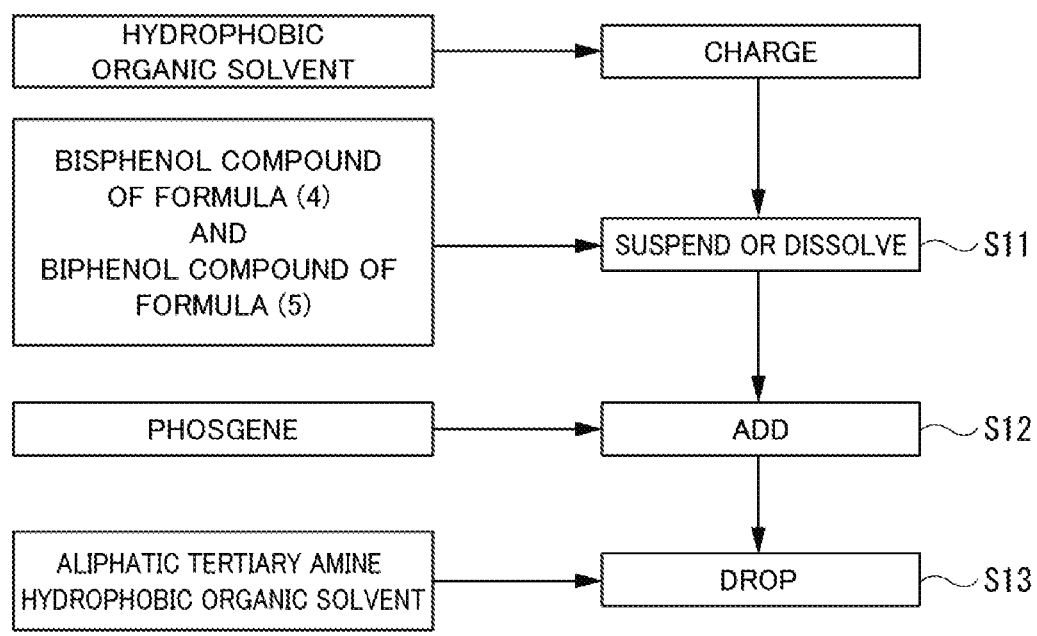
FIG. 1 is a flow chart showing an example of a production method of a bischloroformate composition.

Detailed description is made below on a bischloroformate composition, a production method of the bischloroformate composition, a bischloroformate-composition-containing solution, a polycarbonate resin (occasionally referred to as "polycarbonate copolymer" or "PC copolymer" below), a production method of the polycarbonate resin, a coating liquid, an electrophotographic photoreceptor, and an electrophotographic device according to an exemplary embodiment of the invention.

Bischloroformate Composition

A bischloroformate composition of this exemplary embodiment, i.e., a bischloroformate composition represented by a formula (1) below, contains a plurality of Ar components. The bischloroformate composition of this exemplary embodiment contains as Ar at least one $Ar_1$ and at least one $Ar_2$.

[Formula 12]

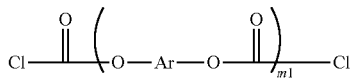
(1)

In the formula (1), m1 represents an average number of monomer units in the bischloroformate composition. The average number of monomer units (m1) of the bischloroformate composition is calculated using an expression (Numerical Expression 1) below. m1 is from 1.0 to 1.99, preferably 1.5 or less, more preferably 1.15 or less.

In the formula (1), Ar is a group ($Ar_1$) represented by a formula (2) below or a group ($Ar_2$) represented by a formula (3) below.

[Formula 13]

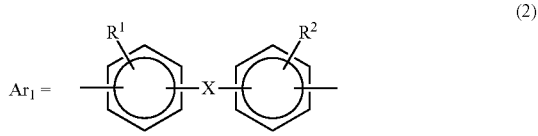
(2)

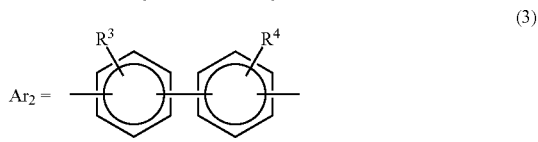
(3)

In the formula (2), $R^1$ and $R^2$ are each independently a hydrogen atom or a substituent, $R^1$ and $R^2$ as substituents being each independently selected from the group consisting of a trifluoromethyl group and an alkyl group having 1 to 3 carbon atoms.

X is selected from the group consisting of
—O—, —CO—, —S—, —$SO_2$—, —$CR^5R^6$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below.

[Formula 14]

(100)

In the formula (100), R are each independently an aliphatic hydrocarbon group having 1 to 6 carbon atoms.

Examples of the aliphatic hydrocarbon group having 1 to 6 carbon atoms include a methyl group, an ethyl group, a propyl group, a butyl group, and a hexyl group.

$R^5$ and $R^6$ are each independently a hydrogen atom or a substituent, $R^5$ and $R^6$ as substituents being each independently selected from the group consisting of an alkyl group having 1 to 5 carbon atoms, a trifluoromethyl group, and a substituted or unsubstituted aryl group having 6 to 12 carbon atoms.

In the formula (3), $R^3$ and $R^4$ are each independently selected from the group consisting of a perfluoroalkyl group having 1 to 3 carbon atoms and an alkyl group having 1 to 3 carbon atoms.

In the bischloroformate composition of this exemplary embodiment, a molar composition ratio represented by $Ar_1/(Ar_1+Ar_2)$ ranges from 45 mol % to 99 mol %, the molar composition ratio meaning a mole percentage of a skeleton represented by $Ar_1$ with respect to the total mole percentage (100 mol %) of the skeleton represented by $Ar_1$ and a skeleton represented by $Ar_2$. The molar composition ratio in the above range enables an improvement in the solubility of the bischloroformate composition in a solvent and, consequently, in the solution stability.

The molar composition ratio represented by $Ar_1/(Ar_1+Ar_2)$ preferably ranges from 55 mol % to 99 mol %, more preferably from 60 mol % to 90 mol %, further preferably from 67 mol % to 90 mol %, particularly preferably from 70 mol % to 85 mol %.

When $Ar_1$ represents a well-soluble skeleton, i.e., BPCZ, the solubility is considerably improved at a molar composition ratio represented by $Ar_1/(Ar_1+Ar_2)$ of 67 mol % or more. When $Ar_1$ represents BPZ, the solubility is considerably improved at a molar composition ratio represented by $Ar_1/(Ar_1+Ar_2)$ of 71 mol % or more.

In the bischloroformate composition of this exemplary embodiment, the average number of monomer units (m1) calculated using an expression (Numerical Expression 1) below is 1.99 or less. The average number of monomer units (m1) means an average of the monomer units of a bischloroformate compound(s) contained in the bischloroformate composition. For instance, when the bischloroformate composition contains one molecule in the form of a bischloroformate compound X having a single monomer unit and one molecule in the form of a bischloroformate compound Y having two monomer units, the bischloroformate composition has an average number of monomer units (m1) of 1.5 as calculated below.

[Numerical Expression 1]

$$m1 = \frac{\text{monomer unit(s) of bischloroformate compound } X + \text{monomer unit(s) of bischloroformate compound } Y}{\text{total number of molecules of bischloroformate compound(s)}} = \frac{1+2}{2} = 1.5$$

The lower limit of the average number of monomer units (m1) is 1.0 or more. The average number of monomer units (m1) of the bischloroformate composition preferably ranges from 1.0 to 1.5, more preferably from 1.0 to 1.3.

[Numerical Expression 3]

average number of monomer units(m1)=1+(Mav−M1)/M2  (Numerical Expression 1)

In the expression (Numerical Expression 1), May represents (2×1000/(CF number)). M1 is an average molecular weight of a bischloroformate compound(s) contained in the bischloroformate composition at a ratio of $Ar_1/(Ar_1+Ar_2)$ with an average number of monomer units (m1) of 1.0 (i.e., an average molecular weight of a bischloroformate compound(s) contained in the bischloroformate composition determined when the molecular weight of Ar is a weight average of respective molecular weights of $Ar_1$ and $Ar_2$, where $Ar_1$ is present at a ratio of $Ar_1/(Ar_1+Ar_2)$, with the average number of monomer units (m1) of 1.0).

M2 is (M1−Y).

The CF number [the mole number of a chlorine atom/kg] is (CF value/concentration) of a bischloroformate composition solution produced by fully dissolving the bischloroformate composition in an organic solvent.

The CF value [N] is the mole number of a chlorine atom in the bischloroformate compound contained in 1 L of the bischloroformate composition solution. [N] is also represented as [mol/L].

The wording "the mole number of a chlorine atom in the bischloroformate compound" means the mole number of a chlorine atom bonded to a carbonyl group in the bischloroformate compound. When a molecule has a chlorine atom not bonded to the carbonyl group in the same molecule, the chlorine atom is not counted in the CF value.

The concentration [kg/L] means an amount of a solid content obtained by condensing 1 L of the bischloroformate composition solution.

Y is a total atom weight of two chlorine atoms, one oxygen atom and one carbon atom which are desorbed at polycondensation of a bischloroformate compound and a phenol compound. In other words, Y is a total atom weight of atoms (two chlorine atoms, one oxygen atom, and one carbon atoms) remaining after the following moiety is removed from the structure represented by the formula (1).

[Formula 15]

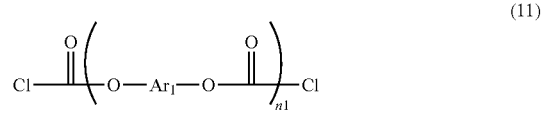

The bischloroformate composition of this exemplary embodiment preferably contains at least one first bischloroformate compound represented by a formula (11) below and at least one second bischloroformate compound represented by a formula (12) below.

[Formula 16]

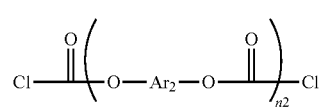

(11)

(12)

In the formula (11), $Ar_1$ represents a group represented by the formula (2). n1 is an integer of 1 or more, preferably an integer of 1 to 5, more preferably an integer of 1 to 3, further preferably 1 or 2, particularly preferably 1.

In the formula (12), $Ar_e$ represents a group represented by the formula (3). n2 is an integer of 1 or more, preferably an integer of 1 to 5, more preferably an integer of 1 to 3, further preferably 1 or 2, particularly preferably Examples of the first bischloroformate compound include compounds represented by formulae (11A) to (11C) below.

[Formula 17]

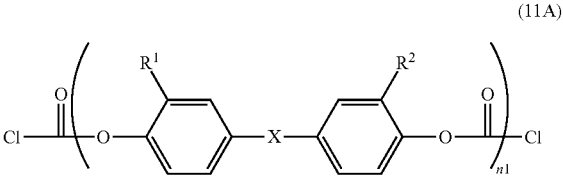

(11A)

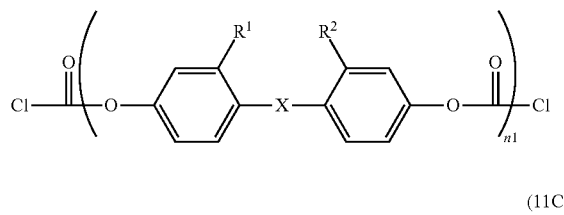

(11B)

(11C)

In the formulae (11A) to (11C), $R^1$, $R^2$ and X respectively mean the same as $R^1$, $R^2$ and X in the formula (2). n1 means the same as n1 in the formula (11).

Examples of the second bischloroformate compound include compounds represented by formulae (12A) to (12C) below.

[Formula 18]

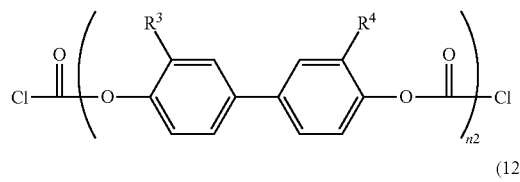

(12A)

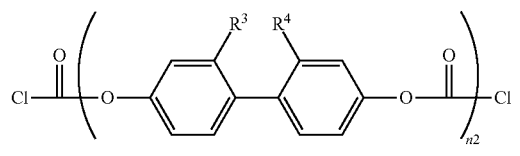

(12B)

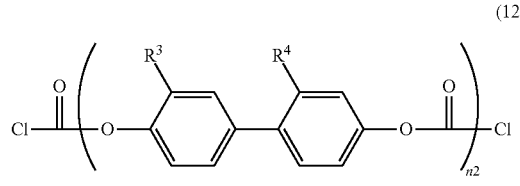

(12C)

In the formulae (12A) to (12C), $R^3$ and $R^4$ respectively mean the same as $R^3$ and $R^4$ in the formula (3). n2 means the same as n2 in the formula (12).

The bischloroformate composition of this exemplary embodiment preferably contains, as the first bischloroformate compound, a compound represented by a formula (6) below, which has a 1,1-bis(phenylene-4-yl)cyclohexane skeleton with excellent mechanical strength and electrical characteristics.

The term "electrical characteristics" means basic characteristics of a photoreceptor such as surface electrification, exposure sensitivity, dark decay, and potential stability, which are associated with an image quality in an electrophotographic process.

[Formula 19]

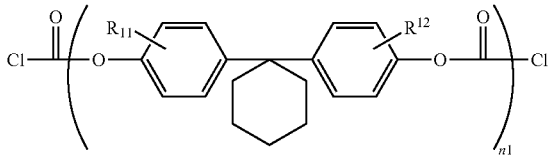

(6)

In the formula (6), n1 means the same as n1 in the formula (11). $R^{11}$ and $R^{12}$ are each independently a hydrogen atom or a methyl group.

The bischloroformate composition of this exemplary embodiment preferably contains, as the second bischloroformate compound, a compound represented by a formula (7) below, which has a 3,3'-dimethylbiphenyl-4,4'-diyl skeleton with excellent mechanical strength and electrical strength. As a high quality image has been increasingly used in recent years, an AC/DC superimposing electrification method in which an AC voltage is superimposed on a DC voltage is used as a method of electrifying a surface of a photosensitive layer of the electrophotographic photoreceptor. According to the AC/DC superimposing electrification method, stability of the electrophotographic photoreceptor is improved, whereas an electrical discharge amount of a surface of the electrophotographic photoreceptor is drastically increased since the AC voltage is superimposed. For this reason, a resin is deteriorated to increase a wear amount of the electrophotographic photoreceptor. A resistance against such a deterioration caused by electrification is referred to as "electrical strength". The electrophotographic photoreceptor has been required to have an electrical strength in addition to a mechanical strength.

[Formula 20]

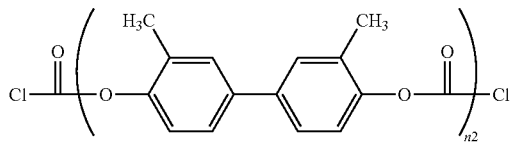

(7)

In the formula (7), n2 means the same as n2 in the formula (12).

The bischloroformate composition of this exemplary embodiment may contain plural types of the first bischloroformate compound and plural types of the second bischloroformate compound.

The bischloroformate composition of this exemplary embodiment preferably contains one type of the first bischloroformate compound and one type of the second bischloroformate compound, and more preferably contains the first bischloroformate compound represented by the formula (6) and the second bischloroformate compound represented by the formula (7),In this case, the bischloroformate composition may contain another bischloroformate compound in addition to the first bischloroformate compound and the second bischloroformate compound.

The term "one type of the first bischloroformate compound" means one of bischloroformate compounds with Ar1 in the formula (11) being the same. When the bischloroformate composition contains plural types of the first bischloroformate compound represented by the formula (11), the respective monomer units n1 of these first bischloroformate compounds may be mutually the same or different. For instance, one type of the first bischloroformate compound may be a bischloroformate compound with Ar1 being the same and n1 being different.

Similarly, the term "one type of the second bischloroformate compound" means one of bischloroformate compounds with Ar2 in the formula (12) being the same. When the bischloroformate composition contains plural types of the second bischloroformate compound represented by the formula (12), the respective monomer units n2 of these second bischloroformate compounds may be mutually the same or different. For instance, one type of the second bischloroformate compound may be a bischloroformate compound with Ar2 being the same and n2 being different.

Production Method of Bischloroformate Composition

According to a production method of the bischloroformate composition of this exemplary embodiment, the bischloroformate composition of this exemplary embodiment is produced, using at least a hydrophobic organic solvent, from a bisphenol compound represented by a formula (4) below, a biphenol compound represented by a formula (5) below, and a phosgene compound.

[Formula 21]

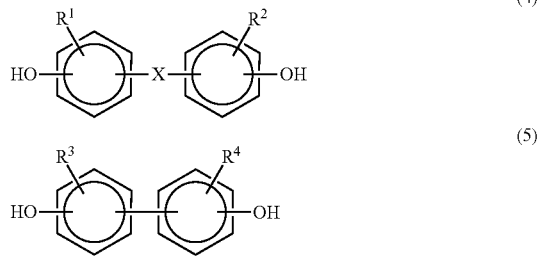

(4)

(5)

In the formula (4), $R^1$, $R^2$ and X respectively mean the same as $R^1$, $R^2$ and X in the formula (2).

In the formula (5), $R^3$ and $R^4$ respectively mean the same as $R^3$ and $R^4$ in the formula (3).

According to the production method of the bischloroformate composition of this exemplary embodiment, the bischloroformate composition of this exemplary embodiment is also preferably produced, using at least a hydrophobic organic solvent, from a bisphenol compound represented by the formula (4), a biphenol compound represented by the formula (5), a phosgene compound, and an aliphatic tertiary amine.

The production method of the bischloroformate composition of this exemplary embodiment is explained below through examples referred to as first to fourth production methods.

First Production Method

According to the first production method, the bischloroformate composition of this exemplary embodiment is produced by mixing a bisphenol compound represented by the formula (4), a biphenol compound represented by the formula (5), a phosgene compound, and an aliphatic tertiary amine in a hydrophobic organic solvent.

Specific steps of the first production method of the bischloroformate composition are as follows.

As shown in FIG. 1, the first production method includes: a suspending/dissolving step (S11) for suspending or dissolving the bisphenol compound represented by the formula (4) and the biphenol compound represented by the formula (5) in the hydrophobic organic solvent; a phosgene-adding step (S12) for adding the phosgene compound to the prepared suspension or solution; and a dropping step (S13) for dropping the aliphatic tertiary amine, which has been diluted with the hydrophobic organic solvent, into a mixture prepared in the phosgene-adding step.

Suspending/Dissolving Step

In the suspending/dissolving step (S11), a suspension or a solution is prepared by mixing the hydrophobic organic solvent, the bisphenol compound represented by the formula (4), and the biphenol compound represented by the formula (5).

Specific examples of the bisphenol compound of the formula (4) include 1,1-bis(3-methyl-4-hydroxyphenyl)methane, 1,1-bis(3-methyl-4-hydroxyphenyl)ethane, 1,1-bis(4-hydroxyphenyl)ethane, 1,2-bis(4-hydroxyphenyl)ethane, 2,2-bis(4-hydroxyphenyl)propane, 2,2-bis(3-methyl-4-hydroxyphenyl)butane, 2,2-bis(4-hydroxyphenyl)butane, 1,1-bis(4-hydroxyphenyl)-1,1-diphenylmethane, 1,1-bis(4-hydroxyphenyl)-1-phenylethane, 1,1-bis(4-hydroxyphenyl)-1-phenylmethane, 1,1-bis(4-hydroxyphenyl)-1-phenylpropane, 1,1-bis(4-hydroxyphenyl)cyclopentane, 1,1-bis(3-methyl-4-hydroxyphenyl)cyclopentane, 1,1-bis(4-hydroxyphenyl)cyclohexane, 1,1-bis(4-hydroxyphenyl)-3,3,5-trimethylcyclohexane, 1,1-bis(4-hydroxyphenyl)cyclodecane, 2,2-bis(3-methyl-4-hydroxyphenyl)propane, 1,1-bis(3-methyl-4-hydroxyphenyl)cyclohexane, 1,1-bis(3-ethyl-4-hydroxyphenyl)cyclohexane, 1,1-bis(3-trifluoromethyl-4-hydroxyphenyl)methane, 2,2-bis(3-trifluoromethyl-4-hydroxyphenyl)ethane, 2,2-bis(2-methyl-4-hydroxyphenyl)propane, 2,2-bis(3-trifluoromethyl-4-hydroxyphenyl)propane, 2,2-bis(3-trifluoromethyl-4-hydroxyphenyl)butane, 1,1-bis(3-trifluoromethyl-4-hydroxyphenyl)cyclohexane, 9,9-bis(4-hydroxyphenyl)fluorene, 9,9-bis(3-methyl-4-hydroxyphenyl)fluorene, 1,3-bis(2-(4-hydroxyphenyl)-2-propyl)benzene, and 1,4-bis(2-(4-hydroxyphenyl)-2-propyl)benzene.

Among the above bisphenol compounds, 1,1-bis(3-methyl-4-hydroxyphenyl)ethane, 1,1-bis(4-hydroxyphenyl)ethane, 2,2-bis(3-methyl-4-hydroxyphenyl)butane, 2,2-bis(4-hydroxyphenyl)butane, 1,1-bis(4-hydroxyphenyl)cyclohexane, 1,1-bis(3-methyl-4-hydroxyphenyl)cyclohexane, 1,1-bis(3-ethyl-4-hydroxyphenyl)cyclohexane, 1,1-bis(3-trifluoromethyl-4-hydroxyphenyl)cyclohexane, and 2,2-bis(3-methyl-4-hydroxyphenyl)propane are preferable, and 1,1-bis(4-hydroxyphenyl)cyclohexane, 1,1-bis(3-ethyl-4-hydroxyphenyl)cyclohexane, 2,2-bis(4-hydroxyphenyl)adamantane, 1,3-bis(4-hydroxyphenyl)adamantane, 2,2-bis(3-methyl-4-hydroxyphenyl)adamantane, 1,3-bis(3-methyl-4-hydroxyphenyl)adamantane, and 2,2-bis(4-hydroxyphenyl)butane are more preferable.

Specific examples of the biphenol compound represented by the formula (5) include 3,3'-dimethyl-4,4'-dihydroxybiphenyl, 2,2'-dimethyl-4,4'-dihydroxybiphenyl, 3,3'-diethyl-4,4'-dihydroxybiphenyl, 2,2'-diethyl-4,4'-dihydroxybiphenyl, 3,3'-dipropyl-4,4'-dihydroxybiphenyl, 3,3'-dibutyl-4,4'-dihydroxybiphenyl, 3,3'-bis(trifluoromethyl)-4,4'-dihydroxybiphenyl, 2,2'-bis(trifluoromethyl)-4,4'-dihydroxybiphenyl, and 3,3'-bis(pentafluoroethyl)-4,4'-dihydroxybiphenyl.

Among the above biphenol compounds, 3,3'-dimethyl-4,4'-dihydroxybiphenyl, 3,3'-diethyl-4,4'-dihydroxybiphenyl and 3,3'-bis(trifluoromethyl)-4,4'-dihydroxybiphenyl are preferable and 3,3'-dimethyl-4,4'-dihydroxybiphenyl is more preferable.

Examples of the hydrophobic organic solvent include an aromatic hydrocarbon solvent, aliphatic hydrocarbon solvent, halogenated hydrocarbon solvent, ketone solvent, and ether solvent.

Examples of the aromatic hydrocarbon solvent include toluene, xylene, and benzene.Examples of the aliphatic hydrocarbon solvent include pentane, heptane, hexane, octane, isooctane, cyclobutane, cyclopentane, cyclohexane, and 1,3-dimethylcyclohexane.Examples of the halogenated hydrocarbon solvent include dichloromethane and chloroform. Examples of the ketone solvent include methylisobutylketone, methylethylketone and cyclohexanone. Examples of the ether solvent include diethylether, diisopropylether, and dibutylether.

One of the above solvents may be used alone or two or more thereof may be used in combination.

The usage of the hydrophobic organic solvent is not limited but is preferably determined such that a total concentration of the materials, namely, the bisphenol compound represented by the formula (4) and the biphenol compound represented by the formula (5), falls within a range from 30 (g/L) to 420 (g/L), more preferably from 60 (g/L) to 250 (g/L).

When the concentration of the materials, namely the bisphenol compound represented by the formula (4) and the biphenol compound represented by the formula (5), is 30 (g/L) or more, the bisphenol compound and the biphenol compound (materials) react well with phosgene. When the concentration is 420 (g/L) or less, the produced bischloroformate composition is well soluble in a solvent.

Phosgene-Adding Step

In the phosgene-adding step (S12), the phosgene compound is added to the suspension or solution prepared in the suspending/dissolving step.

In adding the phosgene compound, for instance, a phosgene solution containing the phosgene compound may be mixed with the suspension or solution containing the bisphenol compound represented by the formula (4) and the biphenol compound represented by the formula (5) at a time or, alternatively, the phosgene solution containing the phosgene compound may be dropped into the suspension or solution containing the bisphenol compound represented by the formula (4) and the biphenol compound represented by the formula (5).

Examples of the phosgene compound include phosgene, diphosgene, and triphosgene. One of the above substances may be used alone or two or more thereof may be used in combination.

The usage of the phosgene compound is not limited but is preferably 0.95 equivalent or more with respect to all the hydroxyl groups in the materials, namely, the bisphenol compound represented by the formula (4) and the biphenol compound represented by the formula (5). The usage of the phosgene compound preferably ranges from 0.97 equivalent to 1.60 equivalent from an economic perspective.

Dropping Step

In the dropping step (S13), the aliphatic tertiary amine having been diluted with the hydrophobic organic solvent is dropped into the mixture of the suspension or solution with the phosgene compound, thus producing the bischloroformate composition of this exemplary embodiment.

In the dropping step (S13), a reaction temperature preferably ranges from −10 degrees C. to 40 degrees C., more preferably from 0 degrees C. to 30 degrees C. A suitable reaction temperature in a reacting step, which is subsequent to the dropping step, is the same as above. At a reaction temperature of −10 degrees C. or more, the solubility of the bischloroformate composition increases, thus allowing a reduction of the usage of the hydrophobic solvent. Further, at a reaction temperature of 40 degrees C. or less, a bischloroformate composition having 1.99 monomer units or less can be efficiently produced.

A reaction time preferably ranges from 0.1 hours to 20 hours, more preferably from 0.1 hours to 6 hours. The "reaction time" herein means a time elapsed from the start of dropping to the start of cleaning.

Examples of the aliphatic tertiary amine include trialkylamines such as triethylamine, trimethylamine, and tripropylamine. One of the above substances may be used alone or two or more thereof may be used in combination.

The usage of the phosgene compound is not limited but is preferably 1.1 equivalent or less with respect to all the hydroxyl groups in the materials, namely, the bisphenol compound represented by the formula (4) and the biphenol compound represented by the formula (5). If an excessive amount of the aliphatic tertiary amine is used, a part of the amine would react with a chloroformate group or a phosgene compound, producing a by-product having a carbamate group (—O—CO—N($C_2H_5$)$_2$). When a ratio of the carbamate group to all the terminal functional groups in the reaction product exceeds 10 mol %, the substitution reaction of the carbamate group does not proceed any more. Thus, production of a high molecular weight polymer may end in failure irrespective of the use of the bisphenol compound represented by the formula (4). Accordingly, the ratio of the carbamate group to all the terminal function groups is preferably 10 mol % or less.

After the dropping step (S13), water is added to the reaction solution to extract hydrochloride for purification. The purified organic layer is taken out and an organic solvent of the organic layer is partly or fully removed to produce the bischloroformate composition of this exemplary embodiment. The purified organic layer itself may be provided as a later-described bischloroformate-composition-containing solution.

In adding water to the reaction solution to separate the aqueous layer and the organic layer from each other after synthesis of the bischloroformate composition of this exemplary embodiment, the hydrogen ion concentration (pH) of the aqueous layer is preferably 4 or less, more preferably in a range from 1 to 3. At a hydrogen ion concentration of 4 or less, an amine salt can be efficiently carried to the aqueous layer, thus reducing thehydrolysis of the bischloroformate composition. The hydrogen ion concentration is adjustable using hydrochloric acid or the like.

Second Production Method

Next, the second production method of the bischloroformate composition is described.

The second production method of the bischloroformate composition may use the bisphenol compound represented by the formula (4), the biphenol compound represented by the formula (5), the aliphatic tertiary amine, the hydrophobic organic solvent, and the phosgene compound as used in the first production method.

Figure 2:
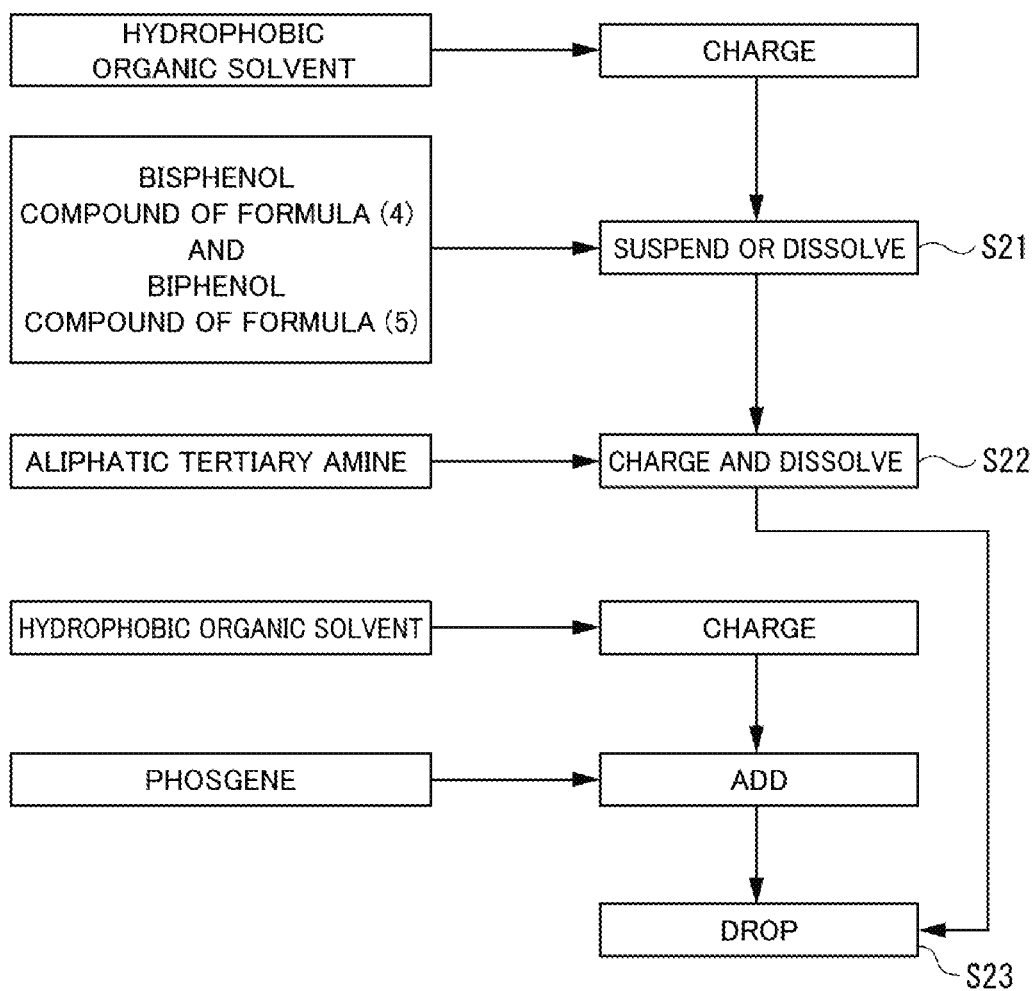
FIG. 2 is a flow chart showing another example of the production method of the bischloroformate composition.

As shown in FIG. 2, the second production method includes: a suspending/dissolving step (S21) for suspending or dissolving the bisphenol compound represented by the formula (4) and the biphenol compound represented by the formula (5) in the hydrophobic organic solvent; an amine-adding step (S22) for adding the aliphatic tertiary amine in the prepared suspension or solution; and an amine-dropping step (phosgene-mixing step) (S23) for dropping the prepared solution added with the aliphatic tertiary amine into the phosgene compound having been diluted with the hydrophobic organic solvent.

In the suspending/dissolving step (S21), a suspension or a solution is prepared by mixing the hydrophobic organic solvent, the bisphenol compound represented by the formula (4), and the biphenol compound represented by the formula (5). In the amine-adding step (S22), the prepared suspension or solution is mixed with the aliphatic tertiary amine to prepare a solution. In the phosgene-mixing step (S23), a phosgene solution is prepared from the phosgene compound and the hydrophobic organic solvent and the solution prepared in the amine-adding step is dropped into this phosgene solution, thus producing the bischloroformate composition of this exemplary embodiment.

After the phosgene-mixing step (S23), water is added to the reaction solution to extract hydrochloride for purification in the same manner as in the first production method. The purified organic layer is taken out and an organic solvent of the organic layer is partly or fully removed to produce the bischloroformate composition of this exemplary embodiment. The purified organic layer itself may be provided as a later-described bischloroformate-composition-containing solution.

Third Production Method

Next, the third production method of the bischloroformate composition is described.

The third production method of the bischloroformate composition may use the bisphenol compound represented by the formula (4), the biphenol compound represented by the formula (5), the hydrophobic organic solvent, and the phosgene compound as used in the first production method.

According to the third production method, a solution prepared by dissolving the bisphenol compound represented by the formula (4) and the biphenol compound represented by the formula (5) in an alkali solution is continuously reacted with the phosgene compound in a micrometer-order fine flow path under the presence of the hydrophobic organic solvent.

Specifically, the third production method includes: preparing a starting solution by dissolving the bisphenol compound represented by the formula (4) and the biphenol compound represented by the formula (5) in the alkali solution; preparing a phosgene solution by dissolving the phosgene compound in the hydrophobic organic solvent; and continuously reacting the starting solution with the phosgene solution in the micrometer-order fine flow path.

The starting solution is prepared by, for instance, dissolving the bisphenol compound represented by the formula (4) and the biphenol compound represented by the formula (5) in the alkali solution prepared by dissolving sodium hydroxide in water.

The sodium hydroxide is replaceable with any other alkali metal hydroxide (e.g., potassium hydroxide, lithium hydroxide, and cesium hydroxide), alkaline earth metal hydroxide (e.g., calcium hydroxide and barium hydroxide), and alkali metal carbonate (e.g., sodium carbonate and potassium carbonate).

The water may be any normal water such as tap water, distilled water, and ion-exchange water. Such normal water, distilled water and ion-exchange water may be deaerated under a reduced pressure. Alternatively, these waters may be cooled under a stream of nitrogen gas after being boiled.

The phosgene solution is prepared by dissolving the phosgene compound in the hydrophobic organic solvent. The hydrophobic organic solvent may be used at any amount but is preferably used at an amount ranging from 3 parts by mass to 50 parts by mass with respect to the bisphenol compound represented by the formula (4) and the biphenol compound represented by the formula (5) being 100 parts by mass, more preferably used at an amount ranging from 5 parts by mass to 20 parts by mass.

The phosgene compound may be used at any amount but is preferably used at an amount of 0.95 equivalent or more with respect to all the hydroxyl groups in the bisphenol compound represented by the formula (4) and the biphenol compound represented by the formula (5), more preferably at an amount ranging from 0.95 equivalent to 10 equivalent, further preferably at an amount ranging from 1.0 equivalent to 3.0 equivalent. By using the phosgene compound at an amount corresponding to an excessive amount of alkali or more, the reacted mixture can have a relatively high hydrogen ion concentration, thus preventing the bischloroformate compound from reacting with the alkali water during liquid separation. Further, the bischloroformate compound can also be prevented from reacting with the alkali water by suppressing the used amount of the phosgene compound and adding an acid solution corresponding to an excessive amount of alkali at a mixer outlet.

By regulating the flow rate of the starting solution and the flow rate of the phosgene solution, the usage of the phosgene compound per a predetermined time can be theoretically determined.

In the third production method, since the starting solution and phosgene solution are mixed in a micrometer-order reaction space, these solution can be instantly mixed. When the solvent in the phosgene solution is a hydrophobic organic solvent, the phosgene solution is unlikely to mix with the starting solution. However, by continuously reacting the starting solution with the phosgene solution in the micrometer-order fine flow path, the bisphenol compound represented by the formula (4) and the biphenol compound represented by the formula (5) can be easily mixed with phosgene, preventing oligomerization and polymerization of the bisphenol compound represented by the formula (4) and the biphenol compound represented by the formula (5). Thus, a monomer-like bischloroformate composition having an average number of monomer units (m1) of 1.99 or less can be favorably produced.

Examples of a reactor with a flow path fine enough for instant mixing include commercially available micromixer and mixroreactor. Since many of such commercially available reactors have flow paths shaped to enable instant mixing, the inner diameter of the fine flow path herein cannot be unambiguously determined. Accordingly, a wording "micrometer order" is used herein.

Although the inner diameter of the reactor cannot be unambiguously determined as described above, the fine flow path, which has a minimum number of mixing members for mixing solutions therein, is only required to have a micrometer-order major axis (an inner diameter of a cross section of the fine flow path taken vertically with respect to a longitudinal Idirection) of 1 mm or shorter. Supposing that mixing members are juxtaposed with one another in a pipe to form a plurality of fine flow paths, the major axis of the pipe is likely to exceed 1 mm. The major axis of each fine flow path preferably falls within a range from 10 µm to 1000 µm, more preferably from 10 µm to 700 µm. When the major axis of each fine flow path is 1000 µm or less, a time elapsed before the solutions are mixed can be reduced, efficiently producing the bischloroformate composition having an average number of monomer units (m1) of 1.99 or less. There is no lower limit of the major axis. However, when the major axis is 10 μm or more, a mixing portion can be easily processed, increasing a flow rate and, consequently, improving the productivity.

In the micro-meter order fine flow path, a linear velocity of the mixture of the starting solution and the phosgene solution preferably falls within a range from 0.2 m/sec to 50 m/sec, more preferably 0.2 m/sec to 30 m/sec. When the linear velocity is 0.2 m/sec or more, the bischloroformate composition having an average number of monomer units (m1) of 1.99 or less can be favorably produced. Further, when the linear velocity is 50 m/sec or less, a pressure for introducing the starting solution and the phosgene solution into a reacting portion of the micrometer-order fine flow path can be prevented from excessively increasing.

A temperature of the reacting portion of the micrometer-order fine flow path is preferably regulated to fall within a range from -10 degrees C. to 60 degrees C. using a temperature control tank, more preferably from 0 degrees C. to 40 degrees C. When the temperature of the reacting portion of the micrometer-order fine flow path is 60 degrees C. or less, the bischloroformate composition having an average number of monomer units (m1) of 1.99 or less can be favorably produced.

A production machine according to the third production method may be a production machine disclosed in International Publication No. WO 2010/150888.

Fourth Production Method

Next, the fourth production method of the bischloroformate composition is described.

According to the fourth production method of the bischloroformate composition, the bisphenol compound represented by the formula (4) and the biphenol compound represented by the formula (5) are separately suspended or dissolved in respective hydrophobic organic solvents in the suspending/dissolving step according to the first and second production methods. Different bischloroformate compounds are separately synthesized from the bisphenol compound represented by the formula (4) and from the biphenol compound represented by the formula (5). Respective solutions of these bischloroformate compounds are then mixed to prepare a solution such that a molar composition ratio represented by $Ar_1/(Ar_1+Ar_2)$ ranges from 45 mol % to 99 mol %. An organic solvent is then partly or fully removed from the solution prepared by mixing to produce the bischloroformate composition of this exemplary embodiment. The solution itself prepared by mixing may be provided as a later-described bischloroformate-composition-containing solution. Further, one or both of the bischloroformate compound synthesized from the bisphenol compound represented by the formula (4) and the bischloroformate compound synthesized from the bisphenol compound represented by the formula (5) may be respectively replaced with the bischloroformate compound produced from the bisphenol compound represented by the formula (4) and the bischloroformate compound produced from the bisphenol compound represented by the formula (5) by the corresponding third production method.

Through a dedicatedly study of a bischloroformate composition improved in solvent solubility and solution stability and a bischloroformate-composition-containing solution, the inventors have found that the solvent-solubility and the solution stability are improved by adding a bischloroformate compound having a well-soluble bisphenol skeleton ($Ar_1$ skeleton) to a bischloroformate compound having a biphenol skeleton with high crystallinity and low solution stability ($Ar_2$ skeleton) at a molar composition ratio of $Ar_1/(Ar_1+Ar_2)$ ranging from 45 mol % to 99 mol % with respect to the total amount of these compounds. Further, the inventors have found that a polycarbonate resin consisting mainly of a biphenol skeleton that is produced from a bisphenol-skeleton-containing bischloroformate composition has an improved molecular weight stability.

The bischloroformate composition of this exemplary embodiment, which contains a bischloroformate compound having a biphenol skeleton with high crystallinity and low solution stability and a bischloroformate compound having a well-soluble bisphenol skeleton, is well-soluble in a solvent. Further, the solution stability is improved, since the bischloroformate compound having the well-soluble bisphenol skeleton is contained in an amount ranging from 45 mol % to 99 mol % with respect to the total amount of these compounds. Consequently, a solid content concentration with respect to the solvent can also be improved.

Bischloroformate-Composition-Containing Solution

The bischloroformate-composition-containing solution of this exemplary embodiment contains at least the bischloroformate composition of this exemplary embodiment and a solvent.

A single solvent or a mixture of a plurality of solvents may be used as the solvent used in the bischloroformate-composition-containing solution of this exemplary embodiment, considering the characteristic of the bischloroformate composition of this exemplary embodiment and other materials, such as solubility, dispersibility, viscosity, evaporation speed, chemical stability, and stability against physical changes.

The solvent preferably contains an organic solvent. Specific examples of the organic solvent include an aromatic hydrocarbon solvent, ketone solvent, ester solvent, halogenated hydrocarbon solvent, ether solvent, amide solvent, and sulfoxide solvent.

Examples of the aromatic hydrocarbon solvent include benzene, toluene, xylene, and chlorobenzene. Examples of the ketone solvent include acetone, methylethylketone, cyclohexanone, cyclopentanone, methylisobutylketone. Examples of the ester solvent include acetic ether, ethyl cellosolve, and ccaprolactam. Examples of the halogenated hydrocarbon solvent include carbon tetrachloride, carbon tetrabromide, chloroform, dichloromethane, and tetrachloroethane. Examples of the ether solvent include tetrahydrofuran, dioxolane, and dioxane. Examples of the amide solvent include dimethylformamide and diethylformamide. Examples of the sulfoxide solvent include dimethylsulfoxide.

One of the above solvents may be used alone or two or more thereof may be used together as a mixture solvent.

In the bischloroformate-composition-containing solution of this exemplary embodiment, a component concentration of the bischloroformate composition preferably ranges from 60 g/L to 210 g/L, more preferably from 90 g/L to 200 g/L, further preferably from 120 g/L to 190 g/L, considering convenience in producing a resin from the bischloroformate composition of this exemplary embodiment.

The bischloroformate-composition-containing solution of this exemplary embodiment may contain one type of the bischloroformate composition according to this exemplary embodiment alone or two or more types thereof.

The bischloroformate composition of this exemplary embodiment, which is well soluble in a solvent, neither whitens nor gels when dissolved in the solvent. The bischloroformate-composition-containing solution of this exemplary embodiment, which contains the bischloroformate composition of this exemplary embodiment and the solvent, can be stably stored without either whitening or gelation of a component such as the bischloroformate composition over a long period of time.

Polymer

The bischloroformate composition of this exemplary embodiment is usable as a polymer material. A copolymer can be synthesized using the bischloroformate composition of this exemplary embodiment. The copolymer may be a polycarbonate resin (occasionally simply referred to as "PC resin" hereinbelow).

The polycarbonate resin of this exemplary embodiment is represented by a formula (A1) below and has a molar composition ratio represented by $Ar_2/(Ar_1+Ar_2)$ ranging from 40 mol % to 75 mol %.

[Formula 22]

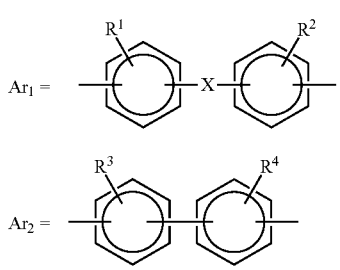

(A1)

In the formula (A1), $Ar_1$ is a group represented by a formula (2) below, $Ar_2$ is a group represented by a formula (3) below, a1 represents an average chain length of the component $Ar_1$, a2 represents an average chain length of the component $Ar_2$, and a1 and a2 are each independently more than 1.0 but not more than 2.7.

[Formula 23]

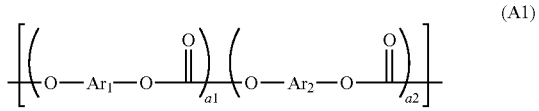

(2)

(3)

In the formula (2):

$R^1$ and $R^2$ are each independently a hydrogen atom or a substituent, $R^1$ and $R^2$ as substituents being each independently selected from the group consisting of a trifluoromethyl group, and an alkyl group having 1 to 3 carbon atoms;

X is selected from the group consisting of —O—, —CO—, —S—, —SO$_2$—, —CR$^5$R$^6$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below; and $R^5$ and $R^6$ are each independently a hydrogen atom or a substituent, $R^5$ and $R^6$ as substituents being each independently selected from the group consisting of an alkyl group having 1 to 5 carbon atoms, a trifluoromethyl group, and a substituted or unsubstituted aryl group having 6 to 12 carbon atoms.

In the formula (3), $R^3$ and $R^4$ are each independently selected from the group consisting of a perfluoroalkyl group having 1 to 3 carbon atoms, and an alkyl group having 1 to 3 carbon atoms.

[Formula 24]

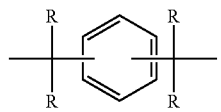

(100)

In the formula (100), R are each independently an aliphatic hydrocarbon group having 1 to 6 carbon atoms.

It should be noted that the term "component $Ar_1$" according to the invention means a structure (block unit) represented by a formula (a1) below. Similarly, the term "component $Ar_2$" according to the invention means a structure (block unit) represented by a formula (a2) below.

[Formula 25]

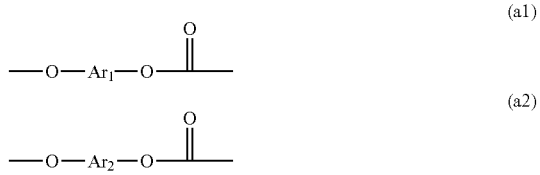

(a1)

(a2)

a1 of the resin represented by the formula (A1) is more than 1.0 but not more than 2.7, preferably more than 1.0 but not more than 2.3, more preferably more than 1.0 but not more than 2.2, further preferably more than 1.0 but not more than 1.99. a2 is more than 1.0 but not more than 2.7, preferably more than 1.0 but not more than 2.3, more preferably more than 1.0 but not more than 2.2, further preferably more than 1.0 but not more than 1.99.

b×(a1+a2) is a value of 30 to 300. When b×(a1+a2) is 30 or more, the resin has a good durability. When b×(a1+a2) is 300 or less, a viscosity becomes suitable for resin-molding. b×(a1+a2) is preferably a value of 40 to 200, more preferably a value of 50 to 150.

Preferably, a solution prepared by dissolving the polycarbonate resin of this exemplary embodiment in methylene chloride at a concentration of 10 mass % has a haze value of less than 10% at an optical path length of 10 mm and a solution prepared by dissolving the polycarbonate resin of this exemplary embodiment in tetrahydrofuran at a concentration of 20 mass % (hereinafter occasionally abbreviated as "THF") has a haze value of less than 10% at an optical path length of 10 mm. When the solution prepared by dissolving the PC resin in methylene chloride at 10 mass % or in THF at 20 mass % has a haze value of less than 10% at an optical path length of 10 mm, a resin product produced by wet molding has an excellent transparency. Further, an electrophotographic photoreceptor using such a resin has excellent electrical characteristics.

The haze value can be measured using a full automatic haze computer (HGM-2D) manufactured by Suga Test Instruments Co.,Ltd. in accordance with JIS K7105.

When a solution prepared by dissolving the polycarbonate resin of this exemplary embodiment in THF at a concentration of 40 mass % is left still at a room temperature (20 to 28 degrees C.) for three hours or more, added with THF so that a solid content concentration of the resin reaches 20 mass %, and further dissolved by stirring and shaking at a room temperature (20 to 28 degrees C.) for five hours or more, the solution preferably contains neither gel component nor insoluble component and has a haze value of less than 10% at an optical path length of 10 mm.

For resin solubility, a solubility test is typically performed using a predetermined solvent at a predetermined concentration. However, such a typical solubility test entails some problems in association with an actual dissolving step. Specifically, the solubility inevitably differs (e.g., occurrence of insoluble matter and white turbidity) depending on a dissolving operation and a possible change in the appearance (e.g., gelation) of the solution kept in storage cannot be determined at an initial stage.

These problems are supposed to occur because a large-scale "dissolving operation" makes the solution locally have different ratios between the solvent and the resin from the ratio as a whole and, consequently, the resin is transformed (e.g, crystalized) by the solvent.

To seek a solubility test capable of evaluation considering the above-described non-uniformity and tendency of transformation by a solvent, the inventors have found a method in which the initial concentration is set at 40 mass % and then the solution is diluted to 20 mass % and established a method capable of evaluating a material even in terms of "applicability to a solution-producing step". The resin produced by this method preferably has a haze value of less than 10% at an optical path length of 10 mm, more preferably a haze value of 5% or less.

The polycarbonate resin of this exemplary embodiment is preferably represented by the formula (A1) in which $Ar^1$ is a group represented by a formula (2a) below and $Ar^2$ is a group represented by a formula (3a) below.

[Formula 26]

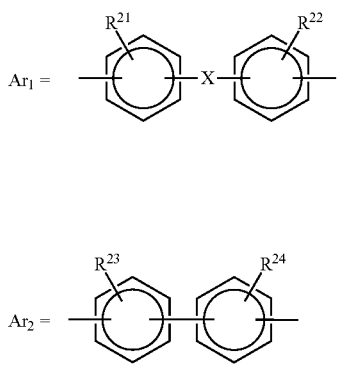

In the formula (2a):
$R^{21}$ and $R^{22}$ are each independently a hydrogen atom or a substituent, $R^{21}$ and $R^{22}$ as substituents being each independently selected from the group consisting of a trifluoromethyl group, and an alkyl group having 1 to 3 carbon atoms;

X is selected from the group consisting of —O—, —CO—, —S—, —SO$_2$—, —CR$^{25}$R$^{26}$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below;

$R^{25}$ and $R^{26}$ are each independently a hydrogen atom or a substituent, $R^{25}$ and $R^{26}$ as substituents being each independently selected from the group consisting of an alkyl group having 1 to 5 carbon atoms, a trifluoromethyl group, and a substituted or unsubstituted aryl group having 6 to 12 carbon atoms; and when X is an unsubstituted cyclohexylidene group, $R^{21}$ and $R^{22}$ are not simultaneously methyl groups.

In the formula (3a), $R^{23}$ and $R^{24}$ are each independently selected from the group consisting of an alkyl group having 1 to 3 carbon atoms.

[Formula 27]

In the formula (100), R are each independently an aliphatic hydrocarbon group having 1 to 6 carbon atoms.

When $Ar^1$ in the formula (A1) is a group represented by the formula (2a) and $Ar^2$ in the formula (A1) is a group represented by the formula (3a), a2 in the formula (A1) is preferably, in terms of the solubility of the PC resin, more than 1.0 but not more than 1.99, more preferably more than 1.0 but not more than 1.8, further preferably more than 1.0 but not more than 1.7. When $Ar^1$ in the formula (A1) is a group represented by the formula (2a), $Ar^2$ in the formula (A1) is a group represented by the formula (3a), and a2 in the formula (A1) is more than 1.0 but not more than 1.99, the solubility of the resin is improved. When a2 is more than 1.0 but not more than 1.8, the solubility of the resin is more improved. When a2 is more than 1.0 but not more than 1.7, the solubility of the resin is further more improved. Especially, when a2 is 1.62 or less, a transparent solution can also be produced by the above-described method in which the initial concentration is set at 40 mass % and then the solution is diluted to 20 mass % (i.e., the solubility test capable of evaluation considering the above problems associated with a dissolving operation, such as non-uniformity and tendency of transformation by a solvent).

The polycarbonate resin of this exemplary embodiment is also preferably represented by a formula (A1-1) below with a molar composition ratio thereof represented by $Ar_2/(Ar_1+Ar_2)$ ranging from 59 mol % to 72 mol %.

[Formula 28]

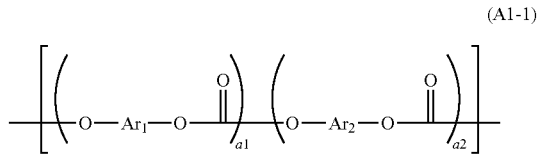

In the formula (A1-1), $Ar_1$ is a group represented by a formula (2b) below, $Ar_2$ is a group represented by a formula (3b) below, a1 represents an average chain length of the component $Ar_1$, a2 represents an average chain length of the component $Ar_2$, and a1 and a2 are each independently more than 1.0 but not more than 2.7.

[Formula 29]

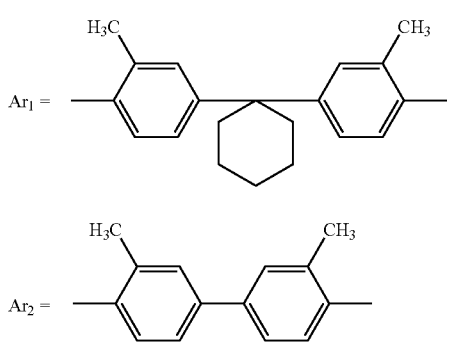

In the formula (A2-1), a molar composition ratio represented by $Ar_2/(Ar_1+Ar_2)$ of 59 mol % or more provides an excellent wear resistance.

In the formula (A2-1), a2 preferably ranges from 1.0 to 2.3, more preferably from 1.0 to 2.2, further preferably from 1.0 to 1.99, particularly preferably from 1.0 to 1.8. BPCZ, which is well-soluble as a base resin as compared with BPZ, improves the solubility of the resin when a2 in the formula (A2-1) (a copolymer of BPCZ and OCBP) is more than 1.0 but not more than 2.3. When a2 is more than 1.0 but not more than 2.2, the solubility of the resin is more improved. When a2 is more than 1.0 but not more than 1.8, the solubility of the resin is further more improved.

The polycarbonate resin of this exemplary embodiment is also preferably represented by a formula (A2) below with a molar composition ratio thereof represented by $Ar_2/(Ar_1+Ar_2)$ ranging from 40 mol % to 75 mol %. A molar composition ratio represented by $Ar_2/(Ar_1+Ar_2)$ of 40 mol % or more provides an excellent wear resistance. Further, a molar composition ratio represented by $Ar_2/(Ar_1+Ar_2)$ of 75 mol % or less is preferable, since the polycarbonate resin has an excellent solubility at this ratio.

The molar composition ratio represented by $Ar_2/(Ar_1+Ar_2)$ more preferably ranges from 50 mol % to 72 mol %, further preferably from 55 mol % to 70 mol %, particularly preferably from 59 mol % to 68 mol %.

[Formula 30]

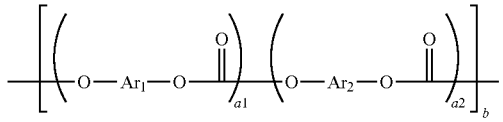

In the formula (A2): $Ar_1$ is a group represented by a formula (2) below; $Ar_2$ is a group represented by a formula (3) below; a1 represents an average chain length of the component $Ar_1$; a2 represents an average chain length of the component $Ar_2$; a1 and a2 are each independently more than 1.0 but not more than 2.7; b represents the number of repetition of a unit in the square bracket; and (a1+a2)×b, which represents an average number of repetition in the resin, is a value of 30 to 300.

[Formula 31]

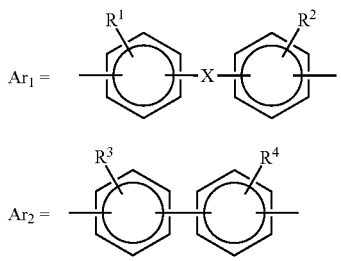

In the formula (2):

$R^1$ and $R^2$ are each independently a hydrogen atom or a substituent, $R^1$ and $R^2$ as substituents being each independently selected from the group consisting of a trifluoromethyl group, and an alkyl group having 1 to 3 carbon atoms;

X is selected from the group consisting of —O—, —CO—, —S—, —SO$_2$—, —CR$^5$R$^6$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below; and $R^5$ and $R^6$ are each independently a hydrogen atom or a substituent, $R^5$ and $R^6$ as substituents being each independently selected from the group consisting of an alkyl group having 1 to 5 carbon atoms, a trifluoromethyl group, and a substituted or unsubstituted aryl group having 6 to 12 carbon atoms.

In the formula (3):

$R^3$ and $R^4$ are each independently selected from the group consisting of a perfluoroalkyl group having 1 to 3 carbon atoms, and an alkyl group having 1 to 3 carbon atoms.

[Formula 32]

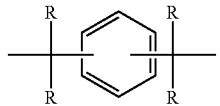

In the formula (100), R are each independently an aliphatic hydrocarbon group having 1 to 6 carbon atoms.

a1 of the resin represented by the formula (A2) is more than 1.0 but not more than 2.7, preferably more than 1.0 but not more than 2.3, more preferably more than 1.0 but not more than 2.2, further preferably more than 1.0 but not more than 1.99. a2 is more than 1.0 but not more than 2.7, preferably more than 1.0 but not more than 2.3, preferably more than 1.0 but not more than 2.2, further preferably more than 1.0 but not more than 1.99. b×(a1+a2) is a value of 30 to 300, preferably a value of 40 to 200, more preferably a value of 50 to 150.

The polycarbonate resin of this exemplary embodiment is also preferably represented by the formula (A2) in which $Ar^1$ is a group represented by a formula (2a) below and $Ar^2$ is a group represented by a formula (3a) below.

[Formula 33]

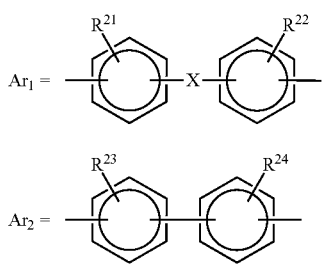

(2a)

(3a)

In the formula (2a):

$R^{21}$ and $R^{22}$ are each independently a hydrogen atom or a substituent, $R^{21}$ and $R^{22}$ as substituents being each independently selected from the group consisting of a trifluoromethyl group, and an alkyl group having 1 to 3 carbon atoms; X is selected from the group consisting of —O—, —CO—, —S—, —SO$_2$—, —CR$^{25}$R$^{26}$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below;

$R^{25}$ and $R^{26}$ are each independently a hydrogen atom or a substituent, $R^{25}$ and $R^{26}$ as substituents being each independently selected from the group consisting of an alkyl group having 1 to 5 carbon atoms, a trifluoromethyl group, and a substituted or unsubstituted aryl group having 6 to 12 carbon atoms; and when X is an unsubstituted cyclohexylidene group, $R^{21}$ and $R^{22}$ are not simultaneously methyl groups.

In the formula (3a), $R^{23}$ and $R^{24}$ are each independently selected from the group consisting of an alkyl group having 1 to 3 carbon atoms.

[Formula 34]

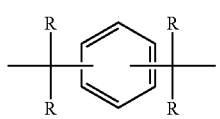

(100)

In the formula (100), R are each independently an aliphatic hydrocarbon group having 1 to 6 carbon atoms.

When Ar$^1$ in the formula (A1) is a group represented by the formula (2a) and Ar$^2$ in the formula (A1) is a group represented by the formula (3a), a2 in the formula (A1) is preferably more than 1.0 but not more than 1.99, more preferably more than 1.0 but not more than 1.8, further preferably more than 1.0 but not more than 1.7.When Ar$^1$ in the formula (A1) is a group represented by the formula (2a), Ar$^2$ in the formula (A1) is a group represented by the formula (3a), and a2 in the formula (A1) is more than 1.0 but not more than 1.99, the solubility of the resin is improved. When a2 is more than 1.0 but not more than 1.8, the solubility of the resin is more improved. When a2 is more than 1.0 but not more than 1.7, the solubility of the resin is further more improved.

The polycarbonate resin of this exemplary embodiment is also preferably represented by a formula (A2-1) below with a molar composition ratio thereof represented by Ar$_2$/(Ar$_1$+Ar$_2$) ranging from 59 mol % to 72 mol %.

[Formula 35]

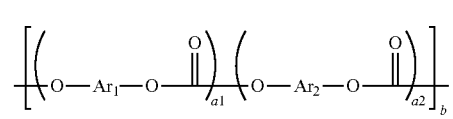

(A2-1)

In the formula (A2-1), Ar$_1$ is a group represented by a formula (2b) below, Ar$_2$ is a group represented by a formula (3b) below, a1 represents an average chain length of the component Ar$_1$, a2 represents an average chain length of the component Ar$_2$, and a1 and a2 are each independently more than 1.0 but not more than 2.7.

[Formula 36]

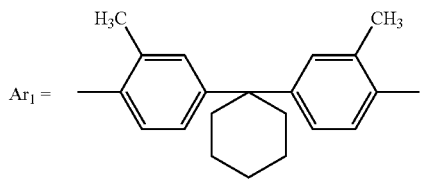

(2b)

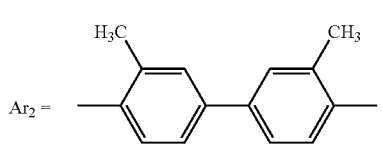

(3b)

In the formula (A2-1), a molar composition ratio represented by Ar$_2$/(Ar$_1$+Ar$_2$) of 59 mol % or more provides an excellent wear resistance.

In the formula (A2-1), a2 is preferably more than 1.0 but not more than 2.3, more preferably more than 1.0 but not more than 2.2, further preferably more than 1.0 but not more than 1.99, particularly preferably more than 1.0 but not more than 1.8.When a2 in the formula (A2-1) is more than 1.0 but not more than 2.3, the solubility of the resin is improved. When a2 is more than 1.0 but not more than 2.2, the solubility of the resin is more improved. When a2 is more than 1.0 but not more than 1.8, the solubility of the resin is further more improved.

The bischloroformate compound of Patent Literature 1, which is less soluble in a solvent, lowers the solution stability. A polymer produced using this compound thus has a lowered molecular weight stability.

Similarly, the technique of Patent Literature 2 entails a problem of the molecular weight stability (molecular weight control) of a polymer, which is attributed to the solution stability lowered by the bischloroformate compound less soluble in an organic solvent. Further, the use of such a bischloroformate compound limits a charging amount of a solid content in a producing process, thus lowering the productivity.

In contrast, the bischloroformate composition of this exemplary embodiment, which contains the bischloroformate compound having the biphenol skeleton (Ar$_2$ skeleton) with high crystallinity and low solution stability and the bischloroformate compound having the well-soluble bisphenol skeleton ($Ar_1$ skeleton), is excellent in solvent solubility and solution stability, thus achieving an excellent production stability when used as a polymer material as compared with a typical biphenol-based bischloroformate compound.

The polymer of this exemplary embodiment is preferably a polymer having a biphenol skeleton as a main skeleton (50 mol % or more with respect to a polymer unit as a whole). Such a polymer having a biphenol skeleton as a main skeleton is more improved in characteristics such as wear resistance and hardness.

Production Method of Polycarbonate Resin

The polycarbonate resin of this exemplary embodiment may be produced by reacting the bischloroformate composition of this exemplary embodiment (material) with a dihydric phenol compound. The use of the bischloroformate composition of this exemplary embodiment improves the solubility of the material.

According to the production method of the polycarbonate resin of this exemplary embodiment, at least one of the bisphenol compound represented by the formula (4) or the biphenol compound represented by the formula (5) is preferably used as the dihydric phenol compound.

According to the production method of the polycarbonate resin of this exemplary embodiment, it is preferable that at least the bischloroformate composition of this exemplary embodiment and the biphenol compound represented by the formula (5) are used. The use of the biphenol compound represented by the formula (5) improves the durability of the produced resin.

The dihydric phenol compound may be dissolved in an alkali solution in use.

Preferable examples of the alkali solution include alkali metal hydroxides and alkaline earth hydroxides. Examples of the alkali metal hydroxides include sodium hydroxide and potassium hydroxide. Examples of the alkaline earth hydroxides include a calcium hydroxide.

Further, trimethylamine may be used as a catalyst to produce the polycarbonate resin of this exemplary embodiment.

According to the production method of the polycarbonate resin of this exemplary embodiment, it is preferable that at least the bischloroformate composition of this exemplary embodiment, an organic solvent, an alkali solution, and a dihydric phenol compound are used and interfacial polycondensation is caused by mixing an organic layer and an aqueous layer.

The organic solvent is preferably an organic solvent substantially immiscible with water and capable of dissolving 5 mass % or more of the polycarbonate resin in a final form.

The organic solvent "substantially immiscible with water" herein means an organic solvent not providing a solution in the form of a uniform layer (a solution containing neither gel nor insoluble matter) when water and the organic solvent are mixed in a composition ratio ranging from 1:9 to 9:1 under normal temperature and normal pressure.

The solubility for the organic solvent to be "capable of dissolving 5 mass % or more of the polycarbonate resin in a final form" refers to the solubility of the polycarbonate resin measured at a temperature ranging from 20 degrees C. to 30 degrees C. under a normal pressure.

The "produced polycarbonate resin in a final form" means a resin produced through a polymerization process according to the production method of the polycarbonate resin of this exemplary embodiment.

Examples of the above-described organic solvent include aromatic hydrocarbons such as toluene, ketones such as cyclohexanone, and halogenated hydrocarbons such as methylene chloride. Among the above, methylene chloride is preferable as being well soluble.

The polymerization process for producing the polycarbonate resin is performed at a temperature ranging from 0 degrees C. to 35 degrees C., preferably from 5 degrees C. to 30 degrees C., further preferably from 5 degrees C. to 25 degrees C.

The repetition components $Ar_1$, $Ar_2$ of the produced resin have respective average chain lengths (a1, a2), which may be measured by $^{13}$C-NMR or $^{1}$H-NMR. For instance, for the resin having BPZ as $Ar_1$ and OCBP as $Ar_2$, a measurement method is as follows.

Measurement Device
   Device: DRX500 manufactured by Bruker BioSpin AG
   Measurement probe: 5-mm TCI CryroProbe Measurement Conditions
   Amount of sample: approximately 50 mg
   Solvent: $CDCl_3$
   Measurement method: $^{13}$C-NMR (reverse gate decoupling method)
   $^{13}$C resonance frequency: 125 MHz
   Frequency of integration: 1024 times
   The number of data points: 64 KB
   Data point interval: 16.65 μsec
   Pulse repetition time: 10 sec
   Measurement temperature: 25 degrees C.
   Measurement center frequency: 100 ppm
   Measurement range: 238 ppm Analyzing Conditions In the $^{13}$C-NMR spectrum, middle one of three peaks attributed to chloroform is set at 77.23 ppm.

At that time, the values of integration of the respective peaks in the following ranges are represented as [1] (BPZ/BPZ), [2] (BPZ/OCBP), and [3] (OCBP/OCBP).

[1]: 152.3 to 152.2 ppm
   [2]: 152.1 to 151.9 ppm
   [3]: 151.9 to 151.7 ppm

In this case, the respective dyad chain fractions (mol %) are as follows.

BPZ/BPZ=100×[1]/([1]+[2]+[3])
   BPZ/OCBP=100×[2]/([1]+[2]+[3])
   OCBP/OCBP=100×[3]/([1]+[2]+[3])

For instance, for the resin having BPCZ as $Ar_1$ and OCBP as $Ar_2$, a measurement method is as follows.

Measurement Device
   Device: JNM-ECA500 manufactured by JEOL Ltd.

Measurement Conditions
   Amount of sample: approximately 250 mg
   Solvent: 3 mL of $CDCl_3$
   $^{13}$C resonance frequency: 125 MHz
   Frequency of integration: 5000 times Analyzing Conditions In the $^{13}$C-NMR spectrum, middle one of three peaks attributed to chloroform is set at 77.07 ppm.

An o-methyl group (16.21 ppm) near a central carbonate bonding in a structure where OCBPs are adjacent to each other (near a carbonate bonding between OCBP and OCBP), an o-methyl group (16.37 ppm) near a central carbonate bonding in a structure where OC-Zs are adjacent to each other (at carbonate bonding between OC-Z and OC-Z), and an o-methyl group (16.18 ppm, 16.40 ppm) near a central carbonate bonding in a structure where OC-BP is adjacent to OC-Z (at a carbonate bonding between OCBP and OC-Z) are different in chemical shift at the peak. Accordingly, ratios of (BPCZ/BPCZ), (BPCZ/OCBP) and (OCBP/OCBP) are calculated from the respective peak areas of o-methyl groups of an OC-BP component and an OC-Z component, which are different in detection position.

At that time, the values of integration of the respective peaks in the following ranges are represented as [1] (BPCZ/BPCZ), [2] (BPCZ/OCBP), and [3] (OCBP/OCBP).

[1]: 16.37 ppm
[2]: 16.18 ppm+16.40 ppm
[3]: 16.21 ppm

In this case, the respective dyad chain fractions (mol %) are as follows.

BPCZ/BPCZ=100×[1]/([1]+[2]+[3])
BPCZ/OCBP=100×[2]/([1]+[2]+[3])
OCBP/OCBP=100×[3]/([1]+[2]+[3])

According to the production method of the polycarbonate resin of this exemplary embodiment, a polycarbonate resin with stable characteristics such as molecular weight can be produced, since the bischloroformate compound of this exemplary embodiment is used as a material. Further, by reducing the average number of repetition of $Ar_1$ and $Ar_2$, the resin with excellent solubility and wear resistance can be produced even when the composition ratio of the highly crystalline $Ar_2$ exceeds 50 mass %.

Coating Liquid

Structure of Coating Liquid

The coating liquid of this exemplary embodiment contains the PC resin of this exemplary embodiment and an organic solvent. The organic solvent is preferably an organic solvent capable of dissolving or dispersing the PC resin. The coating liquid may contain, in addition to the PC resin of this exemplary embodiment and the organic solvent, additives such as a low-molecular compound, a coloring agent (e.g., dye and pigment), a functional compound (e.g., charge transporting material, electron transporting material, hole transporting material, and charge generating material), a filler (e.g., inorganic or organic filler, fiber and fine particles), an antioxidant, an ultraviolet absorber, and an acid scavenger. Substances that may be contained besides the PC resin are exemplified by substances contained in the components of the later-described electrophotographic photoreceptor. The coating liquid may contain other resins as long as the advantages of this exemplary embodiment are not hampered. The coating liquid is exemplified by the following components of the electrophotographic photoreceptor. As the organic solvent usable in this exemplary embodiment, a single solvent may be used or a plurality of solvents may be used by mixture, considering solubility, dispersibility, viscosity, evaporation speed, chemical stability and stability against physical changes of the PC resin according to this exemplary embodiment and other materials.

The solvent is exemplified by the components of the later-described electrophotographic photoreceptor.

A concentration of the PC resin component in the coating liquid of this exemplary embodiment is not limited as long as the coating liquid has a viscosity suitable for the intended use thereof. The concentration of the PC resin component in the coating liquid preferably ranges from 0.1 mass % to 40 mass %, more preferably from 1 mass % to 35 mass %, further preferably from 5 mass % to 30 mass %. When the concentration of the PC resin component in the coating liquid is 40 mass % or less, the viscosity is not excessively high and the coating liquid is easy to apply. When the concentration is 0.1 mass % or more, a suitable viscosity can be maintained, allowing formation of a uniform film. The concentration in the above range is also suitable for reducing a time of drying after coating and for easily forming a film with a desired thickness.

The PC resin of this exemplary embodiment is well compatible with the charge transporting material and, further, neither whitens nor gels even when dissolved in the organic solvent. Accordingly, the coating liquid of this exemplary embodiment, which contains the PC resin of this exemplary embodiment and the organic solvent, can be stably stored over a long period of time without whitening or gelation of the PC resin component over a long period of time even when additionally containing the charge transporting material. Further, an excellent electrophotographic photoreceptor causing no defect on an image can be produced by forming a photosensitive layer thereof from this coating liquid (the coating liquid containing the charge transporting material), since the photosensitive layer is not crystalized.

A ratio between the PC resin and the charge transporting substance in the coating liquid typically ranges from 20:80 to 80:20 in mass ratio, preferably from 30:70 to 70:30.

In the coating liquid of this exemplary embodiment, one type of the PC resin of this exemplary embodiment may be used alone or two or more thereof may be used together.

The coating liquid of this exemplary embodiment is preferably used for forming the charge transporting layer of a laminated electrophotographic photoreceptor in which a sensitive layer at least includes the charge generating layer and the charge transporting layer. When the coating liquid further contains the charge generating substance, the coating liquid is also usable for forming a sensitive layer of a single-layer electrophotographic photoreceptor.

The PC resin of this exemplary embodiment may be used to form an optical member such as an electrophotographic photoreceptor. The electrophotographic photoreceptor containing the PC resin of this exemplary embodiment is excellent in mechanical strength such as wear resistance, electrical strength, and electrical characteristics. The electrophotographic photoreceptor thus exhibits sensitivity and electrical characteristics sufficient for an electrophotographic process.

Structure of Electrophotographic Photoreceptor

The electrophotographic photoreceptor of this exemplary embodiment contains the PC resin of this exemplary embodiment. For instance, the electrophotographic photoreceptor may include a substrate and a photosensitive layer on the substrate, the photosensitive layer containing the PC resin of this exemplary embodiment.

The electrophotographic photoreceptor has been demanded to have a predetermined sensitivity, electrical characteristics and optical characteristics depending on an electrophotography process to be applied. A surface of the photosensitive layer of the electrophotographic photoreceptor is repeatedly subjected to operations such as corona electrification, toner development, transfer onto paper, and cleaning, so that electrical and mechanical external forces are applied to the surface in each operation. Accordingly, the photosensitive layer provided on the surface of the electrophotographic photoreceptor is required to have durability against these external forces in order to maintain electrophotography image quality for a long period of time. Moreover, since the electrophotographic photoreceptor is typically manufactured by dissolving a functional material and a binder resin in an organic solvent and film-casting the obtained solution on a conductive substrate or the like, the solubility and stability in the organic solvent are demanded.

A surface of the electrophotographic photoreceptor has typically been charged by bringing a charge roller into direct contact with a surface of a photosensitive drum (a contact-charging method). Further, a DC-voltage applying method has been suggested to charge the charge roller. However, such a DC-contact charging method, which enables charging according to Paschen's law, considerably lowers the charging stability, causing slight irregularity in discharge and, consequently, irregularity in charge potential. To overcome the above disadvantages, an AC/DC superimposing electrification method, in which an AC voltage is superimposed on a DC voltage, has been created. This electrification method extremely improves the stability in charging. However, superimposing the AC voltage considerably increases a discharge amount on the surface of the electrophotographic photoreceptor, thus increasing a scraped amount of the electrophotographic photoreceptor. To address such a problem, not only a mechanical strength but also an electrical strength has been demanded.

In the polycarbonate copolymer of Patent Literature 2, electrical discharge occurs at a contact nip between an electrophotographic photoreceptor and a charge roll to break intermolecular bonding, thereby causing electrification deterioration. As a result, the wear resistance of the polycarbonate copolymers is extremely reduced. A polyarylate resin as disclosed in Patent Literature 3, which is inferior to a polycarbonate resin in terms of sensitivity and electrical characteristics for an electrophotographic process, is unlikely to provide an electrophotographic photoreceptor that is excellent in mechanical strength and electrical strength and has sensitivity and electrical characteristics sufficient for an electrophotographic process.

In contrast, the electrophotographic photoreceptor of this exemplary embodiment, which includes the photosensitive layer containing the PC resin of this exemplary embodiment, is excellent in mechanical strength, such as wear resistance, and electrical strength. This exemplary embodiment can thus provide an excellent electrophotographic photoreceptor with sensitivity and electrical characteristics sufficient for an electrophotographic process.

The electrophotographic photoreceptor of this exemplary embodiment, which may be in any form such as various known electrophotographic photoreceptors or other electrophotographic photoreceptors as long as the photosensitive layer contains the PC resin of this exemplary embodiment, is preferably in the form of a laminated electrophotographic photoreceptor including a photosensitive layer containing at least one charge generating layer and at least one charge transporting layer or in the form of a single-layer electrophotographic photoreceptor including a single layer containing both a charge generating substance and a charge transporting substance.

The PC resin may be used in any part of the photosensitive layer. However, in order for the invention to sufficiently provide an advantage, the PC resin is preferably used as a binder resin of the charge transporting substance in the charge transporting layer or as a binder resin in the single photosensitive layer. Further, the PC resin is desirably used as a surface protective layer in addition to the photosensitive layer. When the electrophotographic photoreceptor has double charge transporting layers (i.e., multilayer electrophotographic photoreceptor), the PC resin is preferably used in either one of the charge transporting layers.

In the electrophotographic photoreceptor of this exemplary embodiment, one type of the PC resin of this exemplary embodiment may be used alone or two or more types thereof may be used together. Further, as long as an object of the invention is not hampered, a binder-resin component such as another polycarbonate may be contained as desired. In addition, an additive such as an antioxidant may be contained.

The electrophotographic photoreceptor of this exemplary embodiment includes a conductive substrate and a photosensitive layer provided on the conductive substrate. When the photosensitive layer has the charge generating layer and the charge transporting layer, the charge transporting layer may be laminated on the charge generating layer or, reversely, the charge generating layer may be laminated on the charge transporting layer. Alternatively, the photosensitive layer may consist of a single layer simultaneously containing both the charge generating substance and the charge transporting substance. Further, when necessary, a surface layer of the electrophotographic photoreceptor may be provided with a conductive or insulating protective film. Using the PC resin of this exemplary embodiment in the surface layer allows the electrophotographic photoreceptor to be excellent in mechanical strength and electrical strength and have sensitivity and electrical characteristics sufficient for an electrophotographic process.

Furthermore, the electrophotographic photoreceptor may be further provided with an intermediate layer(s) such as adhesive layer for enhancing adhesion between layers and blocking layer for blocking charges.

Conductive substrate materials usable in the electrophotographic photoreceptor of this exemplary embodiment may be a variety of known materials, specific examples of which include: a plate, a drum, and a sheet made of a material such as aluminum, nickel, chrome, palladium, titanium, molybdenum, indium, gold, platinum, silver, copper, zinc, brass, stainless steel, lead oxide, tin oxide, indium oxide, ITO (indium tin oxide; tin-doped indium oxide) and graphite; glass, cloth, paper, plastic film, plastic sheet and seamless belt having been made electrically conductive by coating through vapor deposition, sputtering or application; and a metal drum having been metal-oxidized by electrode oxidation or the like.

The charge generating layer contains at least a charge generating material. The charge generating layer can be obtained by forming a layer of the charge generating material on the underlying substrate by vacuum deposition, sputtering or the like, or by forming a layer in which the charge generating material is bound onto the underlying substrate with use of a binder resin. Various known methods are usable as the method for forming the charge generating layer using the binder resin. The charge generating layer is usually favorably formed as a wet molding by a method including applying, for instance, a coating agent prepared by dispersing or dissolving both the charge generating material and the binder resin in a suitable solvent onto a predetermined underlying substrate, and drying the coating agent.

Various known materials are usable as the charge generating material in the charge generating layer. Specific examples of such materials include: elementary selenium (e.g., amorphous selenium and trigonal selenium), selenium alloy (e.g., selenium-tellurium), selenium compound or selenium-containing composition (e.g., $As_2Se_3$), inorganic material formed of 12 group element(s) and 16 group element(s) in the periodic table (e.g., zinc oxide and CdS—Se), oxide-base semiconductor (e.g., titanium oxide), silicon-base material (e.g., amorphous silicon), metal-free phthalocyanine pigment (e.g., T-type metal-free phthalocyanine and x-type metal-free phthalocyanine), metal phthalocyanine pigment (e.g., a-type copper phthalocyanine, p-type copper phthalocyanine, y-type copper phthalocyanine, c-type copper phthalocyanine, X-type copper phthalocyanine, A-type titanyl phthalocyanine, B-type titanyl phthalocyanine, C-type titanyl phthalocyanine, D-type titanyl phthalocyanine, E-type titanyl phthalocyanine, F-type titanyl phthalocyanine, G-type titanyl phthalocyanine, H-type titanyl phthalocyanine, K-type titanyl phthalocyanine, L-type titanyl phthalocyanine, M-type titanyl phthalocyanine, N-type titanyl phthalocyanine, Y-type titanyl phthalocyanine, oxotitanyl phthalocyanine, titanyl phthalocyanine whose black angle 2θ has its strong diffraction peak at 27.3±0.2 degrees in an X-ray diffraction diagram, and gallium phthalocyanine), cyanine dye; anthracene pigment; bisazo pigment; pyrene pigment; polycyclic quinone pigment; quinacridone pigment; indigo pigment; perylene pigment; pyrylium dye; squarium pigment; anthoanthrone pigment; benzimidazole pigment; azo pigment; thioindigo pigment; quinoline pigment; lake pigment; oxazine pigment; dioxazine pigment; triphenylmethane pigment; azulenium dye; triarylmethane dye; xanthine dye; thiazine dye; thiapyrylium dye; polyvinyl carbazole; and bisbenzimidazole pigment. One of the above compounds may be used alone or two or more thereof may be mixed for use as the charge generating substance. Among the above charge generating substances, a charge generating substance specifically disclosed in JP 11-172003 A is suitable.

The charge transporting layer can be obtained as a wet molding by forming a layer in which the charge transporting substance is bound onto the underlying substrate by a binder resin.

The binder resin for the charge generating layer and the charge transporting layer is not specifically limited. Various known resins are usable. Specific examples of such resins include polystyrene, polyvinyl chloride, polyvinyl acetate, vinyl chloride-vinyl acetate copolymer, polyvinyl acetal, alkyd resin, acrylic resin, polyacrylonitrile, polycarbonate, polyurethane, epoxy resin, phenol resin, polyamide, polyketone, polyacrylamide, butyral resin, polyester resin, vinylidene chloride-vinyl chloride copolymer, methacrylic resin, styrene-butadiene copolymer, vinylidene chloride-acrylonitrile copolymer, vinyl chloride-vinyl acetate-maleic anhydride copolymer, silicone resin, silicone-alkyd resin, phenol-formaldehyde resin, styrene-alkyd resin, melamine resin, polyether resin, benzoguanamine resin, epoxy-acrylate resin, urethane acrylate resin, poly-N-vinylcarbazole, polyvinyl butyral, polyvinyl formal, polysulphone, casein, gelatine, polyvinyl alcohol, ethyl cellulose, cellulose nitrate, carboxymethyl cellulose, vinylidene chloride-base polymer latex, acrylonitrile-butadiene copolymer, vinyl toluene-styrene copolymer, soybean oil-modified alkyd resin, nitrated polystyrene, polymethylstyrene, polyisoprene, polythiocarbonate, polyarylate, polyhaloarylate, polyallyl ether, polyvinyl acrylate, and polyester acrylate.

One of the above resins may be used alone or two or more thereof may be mixed for use. The binder resin used in the charge generating layer and/or the charge transporting layer is suitably the PC resin of this exemplary embodiment.

While various known methods are usable for forming the charge transporting layer, the charge transporting layer is preferably obtained as a wet molding formed by applying a coating liquid in which both the charge transporting substance and the PC resin of this exemplary embodiment are dispersed or dissolved in a suitable solvent onto a predetermined underlying substrate and drying the applied coating liquid. For forming the charge transporting layer, the charge transporting substance and the PC resin are mixed together preferably at a mass ratio of 20:80 to 80:20, more preferably 30:70 to 70:30.

In the charge transporting layer, one type of the PC resin of this exemplary embodiment may be singularly used, or two or more types thereof may be used together. As long as an object of the invention is not hampered, the charge transporting layer may also contain another binder resin in addition to the PC resin of this exemplary embodiment.

The thickness of the thus-formed charge transporting layer is typically approximately in a range from 5 µm to 100 µm, preferably in a range from 10 µm to 30 µm. When the thickness of the charge transporting layer is 5 µm or more, the initial potential does not become low. When the thickness of the charge transporting layer is 100 µm or less, degradation of electrophotographic characteristics can be prevented.

Various known compounds are usable as the charge transporting substance that is usable together with the PC resin of this exemplary embodiment. Preferable examples of such compounds include carbazole compound, indole compound, imidazole compound, oxazole compound, pyrazole compound, oxadiazole compound, pyrazoline compound, thiadiazole compound, aniline compound, hydrazone compound, aromatic amine compound, aliphatic amine compound, stilbene compound, fluorenone compound, butadiene compound, quinone compound, quinodimethane compound, thiazole compound, triazole compound, imidazolone compound, imidazolidine compound, bisimidazolidine compound, oxazolone compound, benzothiazole compound, benzimidazole compound, quinazoline compound, benzofuran compound, acridine compound, phenazine compound, poly-N-vinylcarbazole, polyvinyl pyrene, polyvinyl anthracene, polyvinyl acridine, poly-9-vinyl phenyl anthracene, pyrene-formaldehyde resin, ethylcarbazole resin, and a polymer having the above structure in the main chain or side chain. One of the above compounds may be used alone or two or more thereof may be used together.

Among the above charge transporting substances, a compound specifically disclosed in JP 11-172003 A and a charge transporting substance represented by the following structures are particularly preferably usable.

[Formula 37]
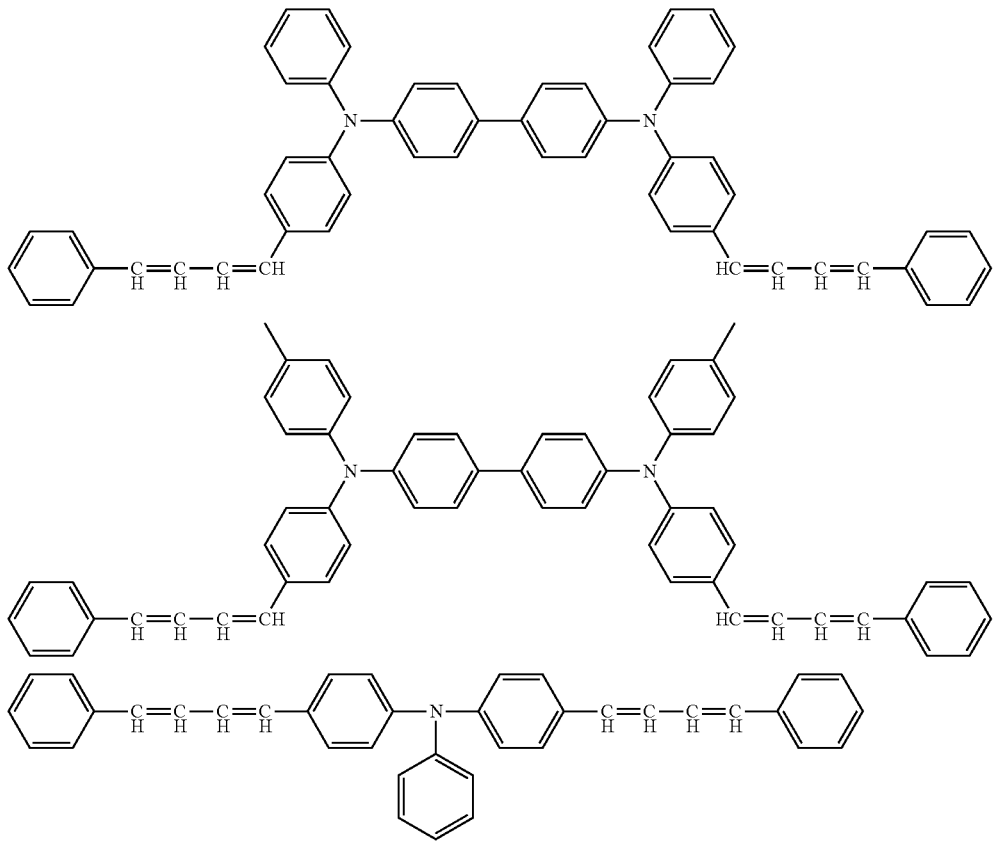
[Formula 38]
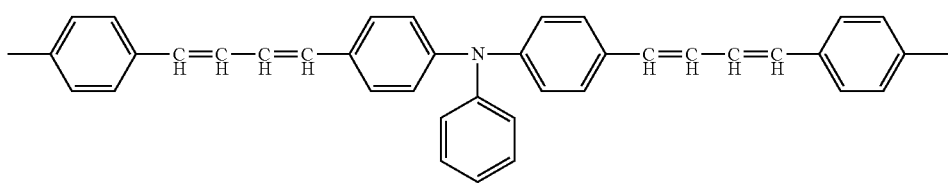
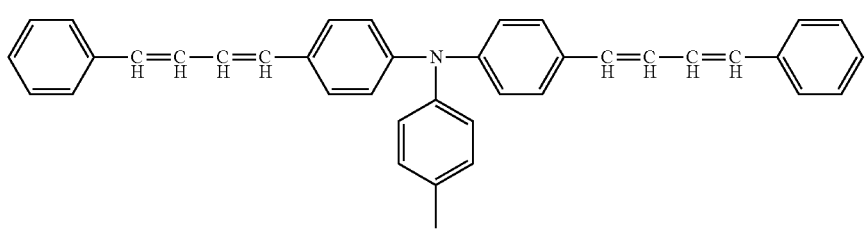
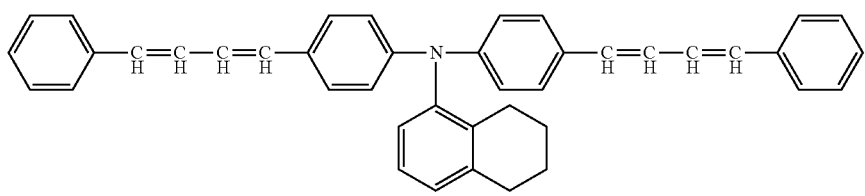

-continued
[Formula 39]
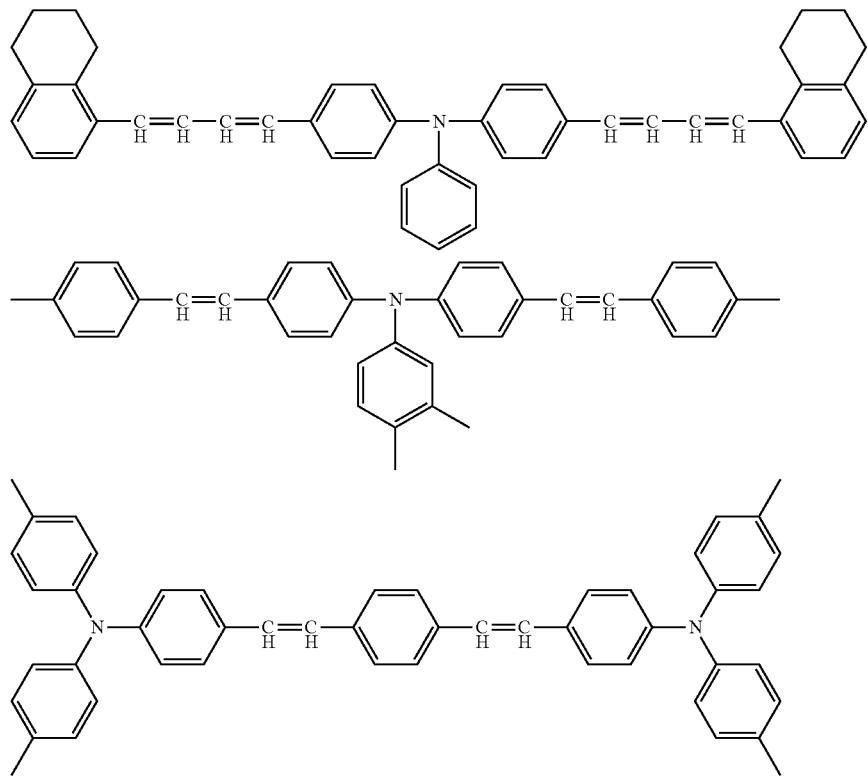
[Formula 40]
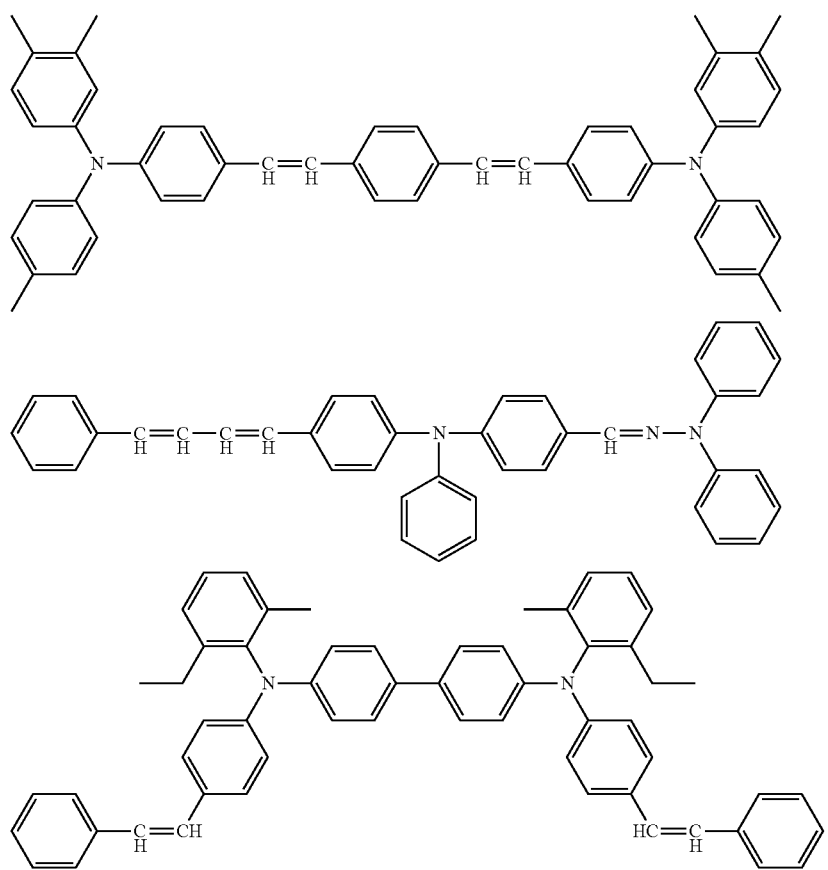

[Formula 41]
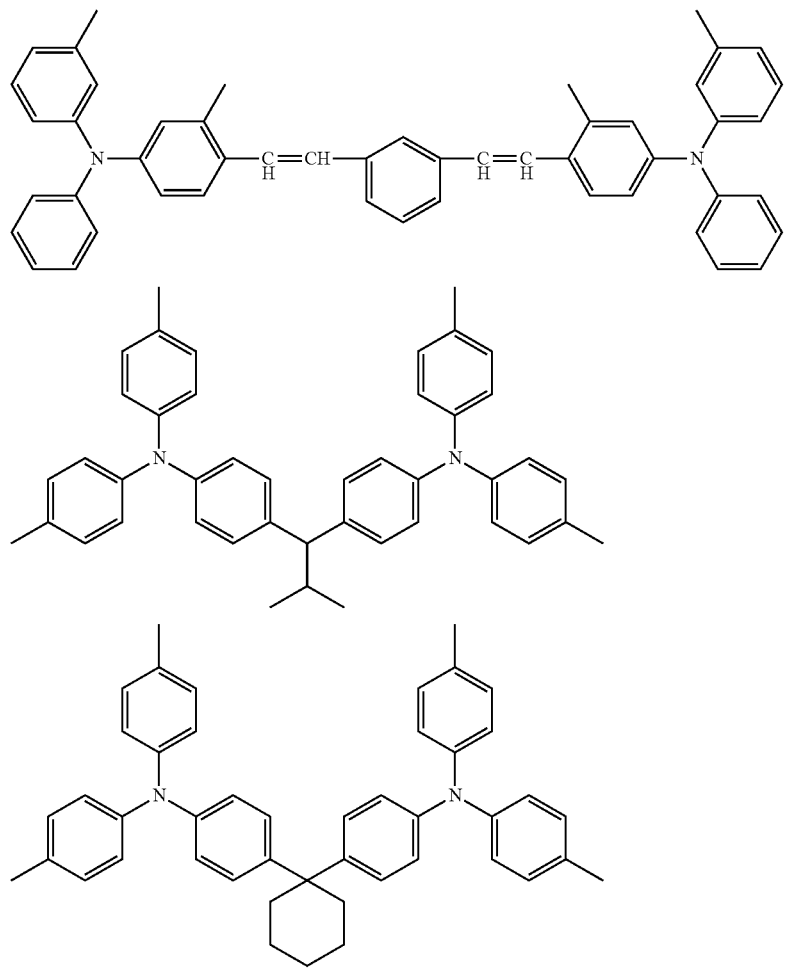
[Formula 42]
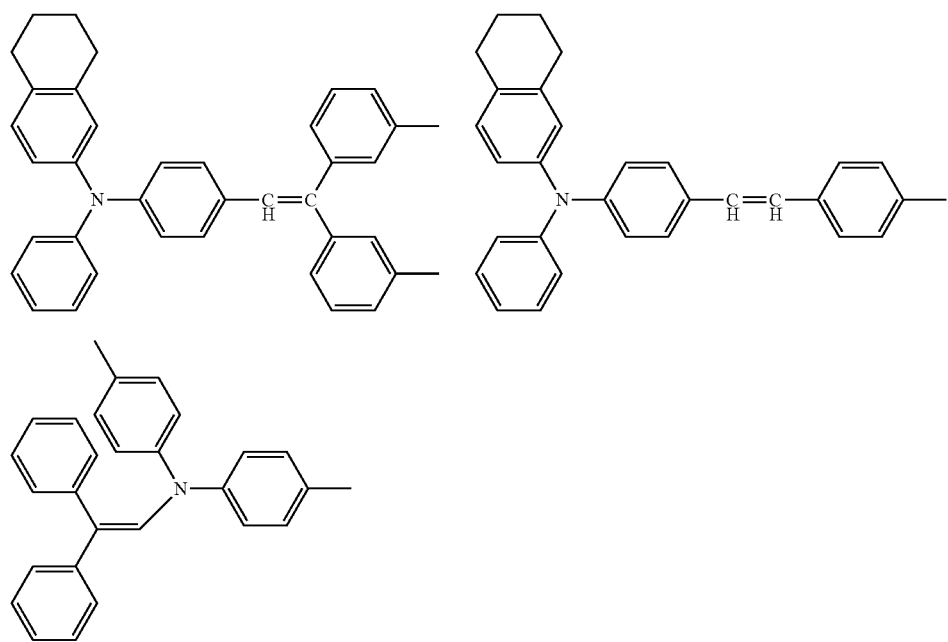

[Formula 43]
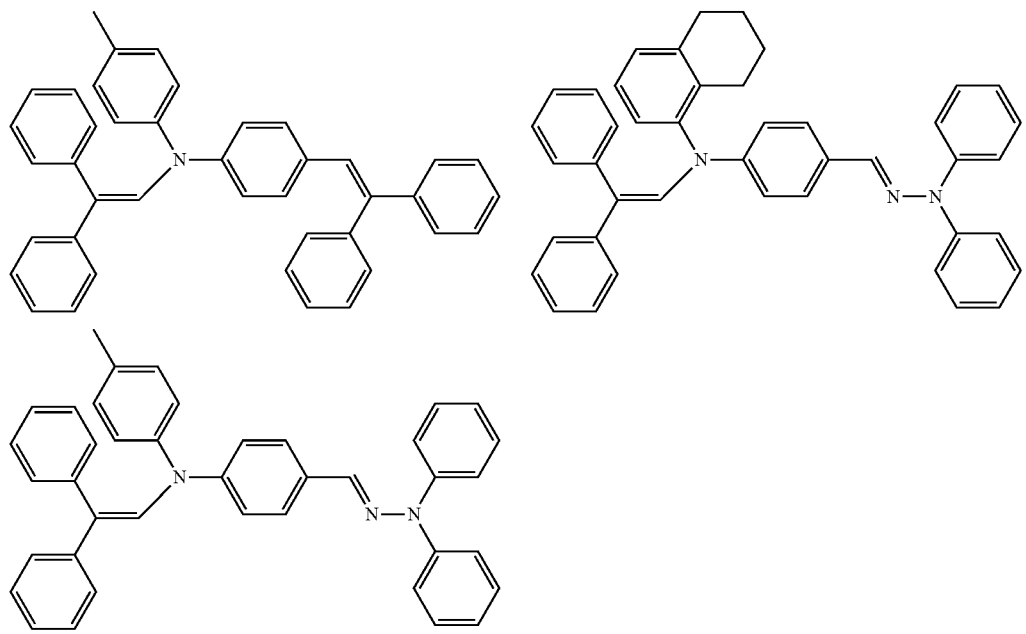
[Formula 44]
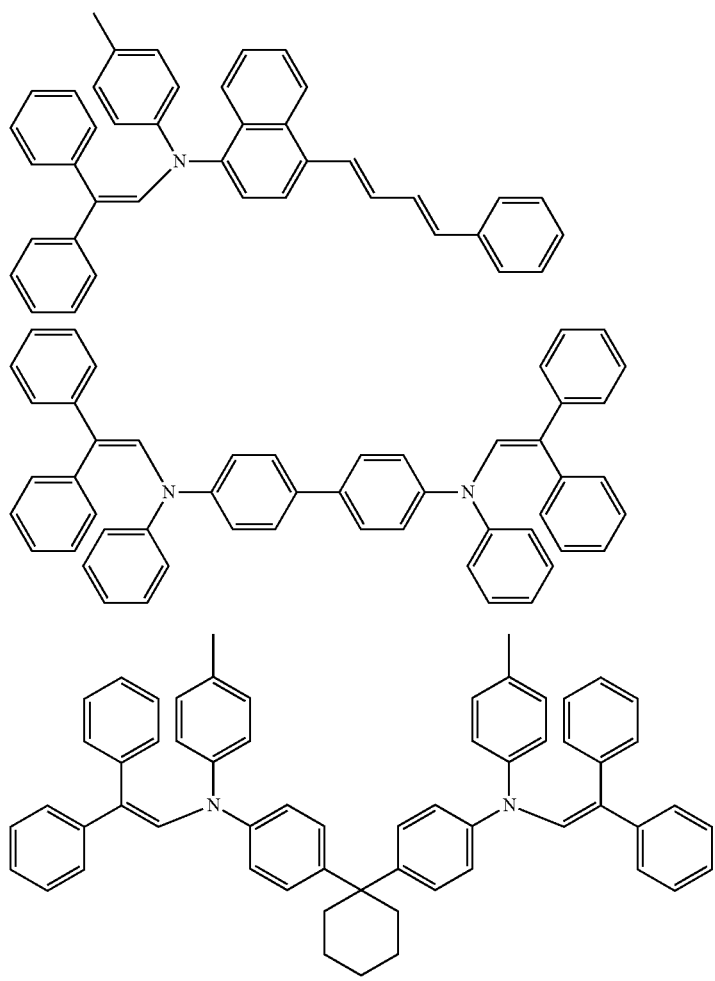

[Formula 45]
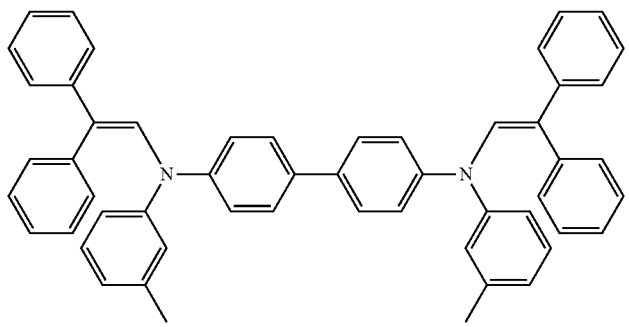
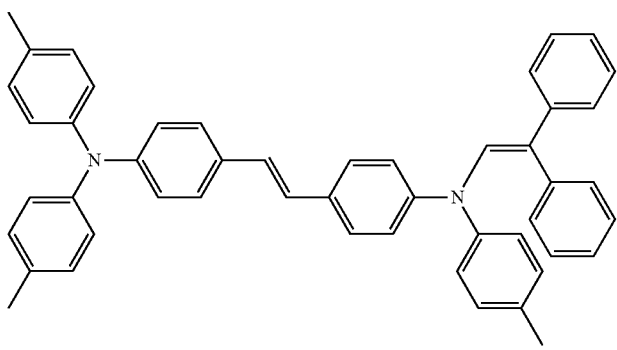
[Formula 46]
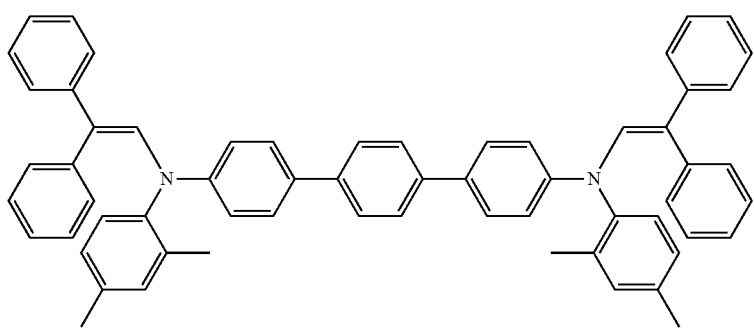
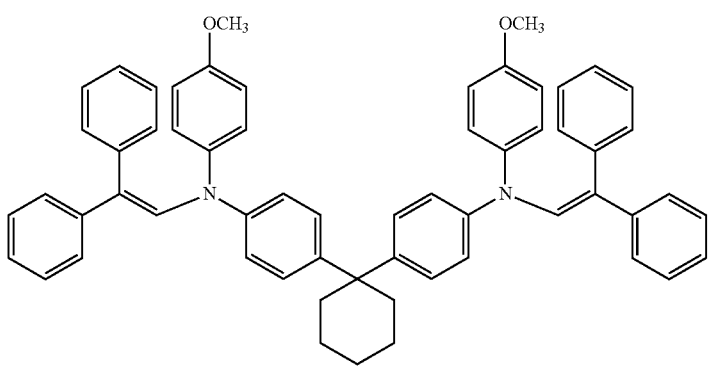

-continued
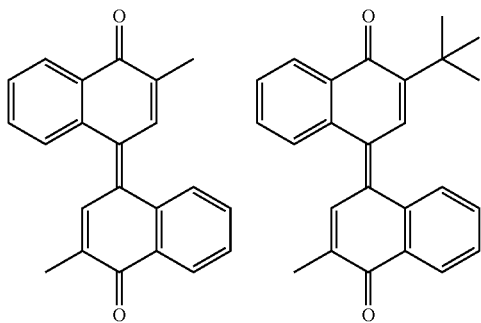
[Formula 47]
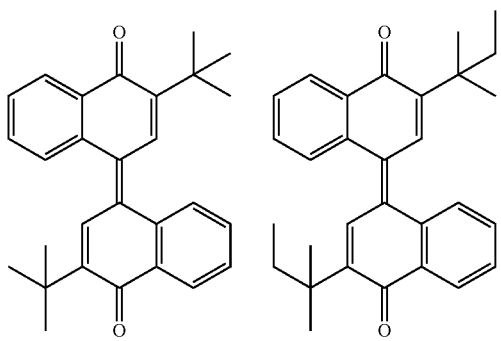
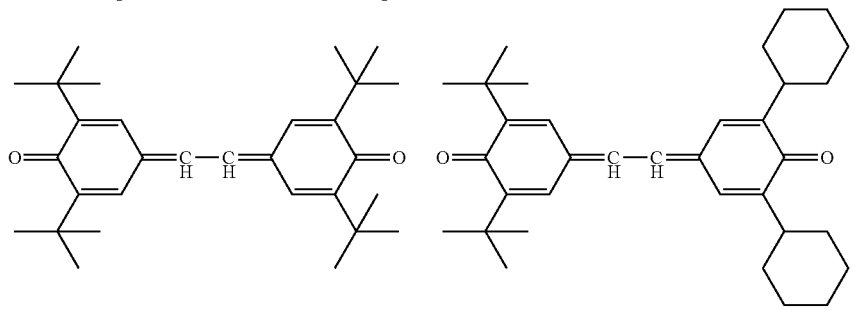
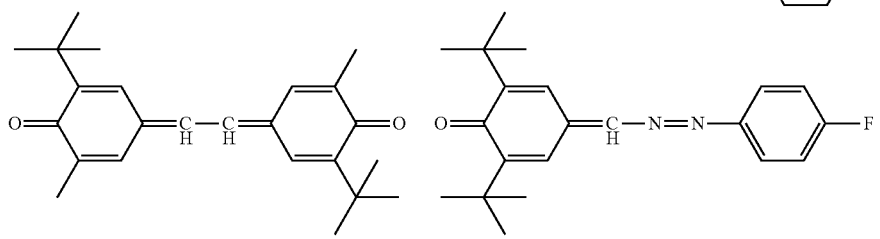
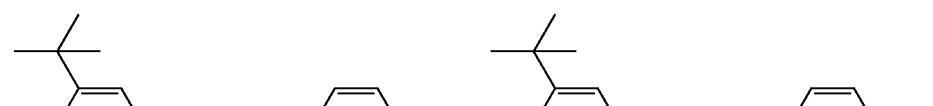
[Formula 48]
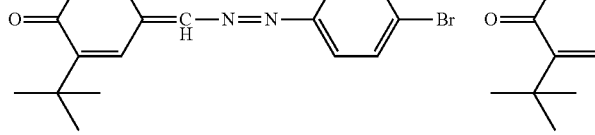
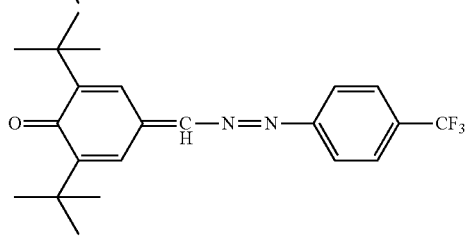

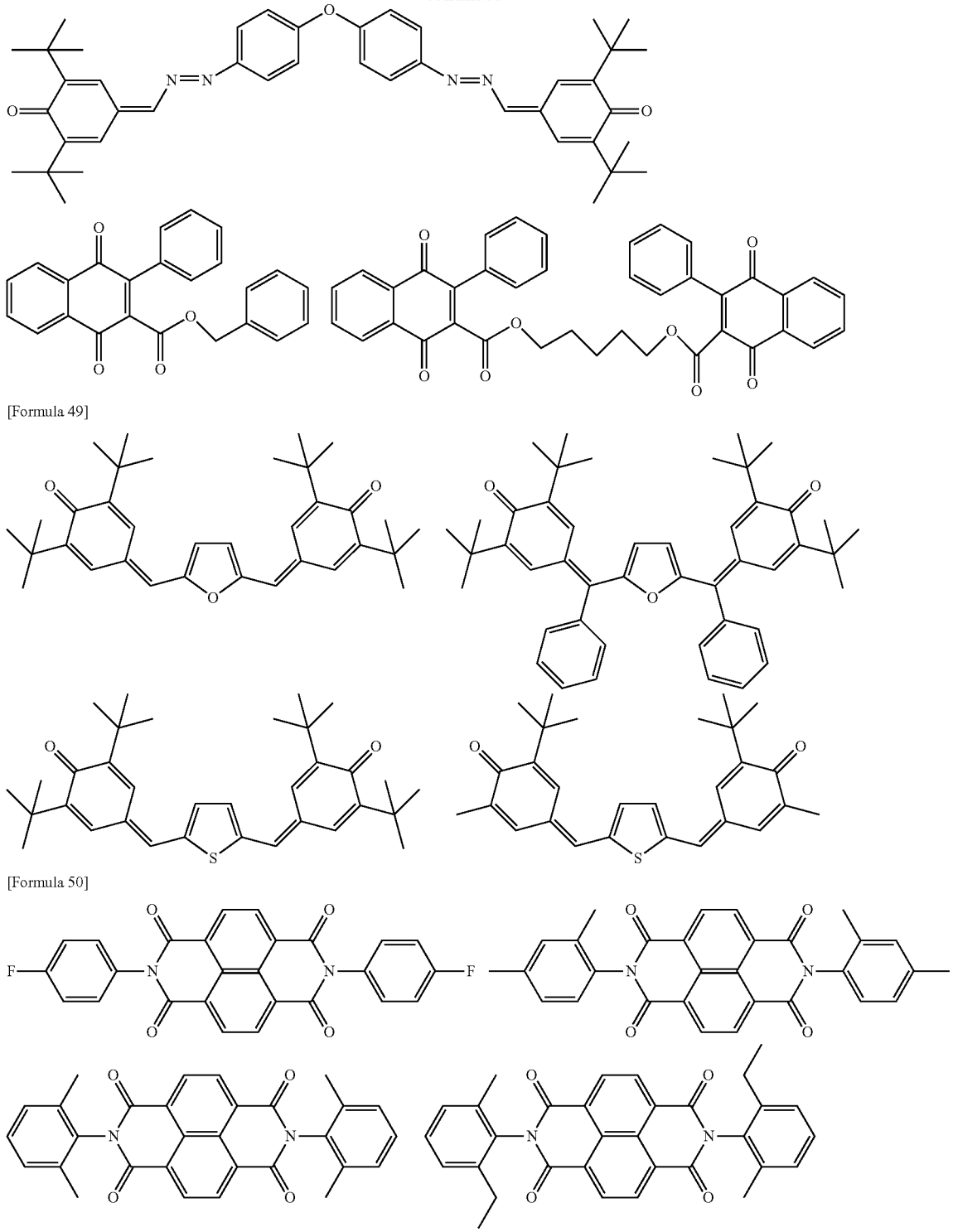

[Formula 49]

[Formula 50]

In the electrophotographic photoreceptor of this exemplary embodiment, the PC resin of this exemplary embodiment is suitably used as the binder resin in at least either one of the charge generating layer and the charge transporting layer.

The electrophotographic photoreceptor of this exemplary embodiment may be provided with a typically used undercoat layer between the conductive substrate and the photosensitive layer. Examples of the undercoat layer include particles (e.g., titanium oxide, aluminum oxide, zirconia, titanic acid, zirconic acid, lanthanum lead, titanium black, silica, lead titanate, barium titanate, tin oxide, indium oxide and silicon oxide), and components such as polyamide resin, phenol resin, casein, melamine resin, benzoguanamine resin, polyurethane resin, epoxy resin, cellulose, cellulose nitrate, polyvinyl alcohol, and polyvinyl butyral resin. The resin usable for the undercoat layer may be the above binder resin or the PC resin of this exemplary embodiment. One of the above particles and the resins may be singularly used or a variety thereof may be mixed together in use. When the mixture is used, a combination of inorganic particles and resin is preferable because a flat and smooth film can be made.

The thickness of the undercoat layer is in a range from 0.01 µm to 10 µm, preferably in a range from 0.1 µm to 7 µm. When the thickness of the undercoat layer is 0.01 µm or more, it becomes possible to form an even undercoat layer. On the other hand, when the thickness of the undercoat layer is 10 µm or less, it is possible to prevent degradation of the electrophotographic characteristics.

The electrophotographic photoreceptor of this exemplary embodiment may be provided with a typically-used known blocking layer between the conductive substrate and the photosensitive layer. The blocking layer may be made of the same resin as the binder resin. Alternatively, the blocking layer may be made of the PC resin of this exemplary embodiment. The thickness of the blocking layer is in a range from 0.01 µm to 20 µm, preferably in a range from 0.1 µm to 10 µm. When the thickness of the blocking layer is 0.01 µm or more, it becomes possible to form an even blocking layer. When the thickness thereof is 20 µm or less, it is possible to prevent degradation of the electrophotographic characteristics.

The electrophotographic photoreceptor of this exemplary embodiment may be further provided with a protective layer laminated on the photosensitive layer. The protective layer may be made of the same resin as the binder resin. Alternatively, it is further preferable that the protective layer is the PC resin of this exemplary embodiment. The thickness of the protective layer is in a range from 0.01 µm to 20 µm, preferably in a range from 0.1 µm to 10 µm. The protective layer may contain a conductive material such as the charge generating substance, the charge transporting substance, an additive, a metal, oxide of the metal, nitride of the metal, salt of the metal, alloy of the metal, carbon black and an organic conductive compound.

In order to enhance performance of the electrophotographic photoreceptor, the charge generating layer and the charge transporting layer may be added with a binder, a plasticizer, a curing catalyst, a fluidity adder, a pinhole controller and a spectral-sensitivity sensitizer (sensitizer dye),In addition, in order to prevent increase in residual potential after repeated use, reduction in charged potential and deterioration in sensitivity, various chemical substances and additives such as antioxidant, surfactant, curl inhibitor and leveling agent may be added.

Examples of the binders include silicone resin, polyamide resin, polyurethane resin, polyester resin, epoxy resin, polyketone resin, polycarbonate colopymer, polystyrene resin, polymethacrylate resin, polyacrylamide resin, polybutadiene resin, polyisoprene resin, melamine resin, benzoguanamine resin, polychloroprene resin, polyacrylonitrile resin, ethyl cellulose resin, cellulose nitrate resin, urea resin, phenol resin, phenoxy resin, polyvinyl butyral resin, formal resin, vinyl acetate resin, vinyl acetate/vinyl chloride copolymer resin, and polyester carbonate resin. In addition, at least one of a thermoset resin and a light-curable resin is also usable. The binder is not specifically limited to the above, as long as the binder is an electric-insulating resin from which a film is formable under normal conditions, and as long as an advantage of the invention is not hampered.

Examples of the plasticizer include biphenyl, chlorinated biphenyl, o-terphenyl, halogenated paraffin, dimethylnaphthalene, dimethyl phthalate, dibutyl phthalate, dioctyl phthalate, diethylene glycol phthalate, triphenyl phosphate, diisobutyl adipate, dimethyl sebacate, dibutyl sebacate, laurate butyl, methylphthalyl ethyl glycolate, dimethyl glycol phthalate, methylnaphthalene, benzophenone, polypropylene, polystyrene, and fluorohydrocarbon.

Examples of the curing catalyst include methanesulfonic acid, dodecylbenzenesulfonic acid and dinonylnaphthalene disulfonic acid. Examples of the fluidity adder include Modaflow$^{TM}$ and Acronal 4F™. Examples of the pinhole controller include benzoin and dimethyl phthalate. The above plasticizer, curing catalyst, fluidity adder and pinhole controller are preferably contained at a content of 5 mass % or less with respect to the charge transporting substance.

When a sensitizer dye is used as a spectral-sensitivity sensitizer, suitable examples of the sensitizer dye include triphenylmethane-base dye (e.g., methyl violet, crystal violet, night blue and Victria blue), acridine dye (e.g., erythrosine, Rhodamine B, Rhodamine 3R, acridine orange and frapeosine), thiazine dye (e.g., methylene blue and methylene green), oxazine dye (e.g., capri blue and meldra blue), cyanine dye, merocyanine dye, styryl dye, pyrylium salt dye, and thiopyrylium salt dye.

In order to enhance the sensitivity, reduce the residual potential and reduce fatigue due to repeated use, the photosensitive layer may be added with an electron-accepting substance. Preferable examples of the electron-accepting material include compounds having high electron affinity such as succinic anhydride, maleic anhydride, dibromo maleic anhydride, phthalic anhydride, tetrachloro phthalic anhydride, tetrabromo phthalic anhydride, 3-nitro phthalic anhydride, 4-nitro phthalic anhydride, pyromellitic anhydride, mellitic anhydride, tetracyanoethylene, tetracyanoquinodimethane, o-dinitro benzene, m-dinitro benzene, 1,3,5-trinitro benzene, p-nitrobenzonitrile, picryl chloride, quinone chlorimide, chloranil, bromanil, benzoquinone, 2,3-dichloro benzoquinone, dichloro dicyano parabenzoquinone, naphthoquinone, diphenoquinone, tropoquinone, anthraquinone, 1-chloro anthraquinone, dinitro anthraquinone, 4-nitrobenzophenone, 4,4 -dinitrobenzophenone, 4-nitrobenzal malonodinitrile, α-cyano-β-(p-cyanophenyl)ethyl acrylate, 9-anthracenyl methylmalonodinitrile, 1-cyano-(p-nitrophenyl)-2-(p-chlorophenyl)ethylene, 2,7-dinitro fluorenone, 2,4,7-trinitro fluorenone, 2,4,5,7-tetranitro fluorenone, 9-fluorenylidene-(dicyano methylene malononitrile), polynitro-9-fluorenylidene-(dicyano methylene malonodinitrile), picric acid, o-nitrobenzoic acid, p-nitrobenzoic acid, 3,5-dinitrobenzoic acid, pentafluorobenzoic acid, 5-nitrosalicylic acid, 3,5-dinitrosalicylic acid, phthalic acid, and mellitic acid. The above compounds may be added to either the charge generating layer or the charge transporting layer. An additive ratio of the compounds is in a range from 0.01 to 200 parts by mass, preferably in a range from 0.1 to 50 parts by mass, per 100 parts by mass of the charge generating substance or the charge transporting substance.

Further, in order to improve surface quality, tetrafluoroethylene resin, trifluoroethylene chloride resin, tetrafluoroethylene hexafluoropropylene resin, vinyl fluoride resin, vinylidene fluoride resin, difluoroethylene dichloride resin, copolymer(s) thereof, or fluorine-base graft polymer may be used. An additive ratio of such surface modifiers is in a range from 0.1 mass % to 60 mass % with respect to the binder resin, preferably in a range from 5 mass % to 40 mass %. When the additive ratio is 0.1 mass % or more, surface modification such as enhancement of surface durability and reduction in surface energy becomes sufficient. When the additive ratio is 60 mass % or less, degradation of the electrophotographic characteristics does not occur.

Preferable examples of the antioxidant include a hindered phenol-base antioxidant, aromatic amine-base antioxidant, hindered amine-base antioxidant, sulfide-base antioxidant and organophosphate-base antioxidant. An additive ratio of such antioxidants is typically in a range from 0.01 mass % to 10 mass %, preferably in a range from 0.1 mass % to 2 mass %, with respect to the charge transporting substance.

Preferable examples of such antioxidants include compounds represented by chemical formulae [Formula 94] to [Formula 101] disclosed in the specification of JP 1 1-1 72003 A.

One of the above antioxidants may be singularly used, or two or more of them may be mixed in use. In addition to the photosensitive layer, the above antioxidant may be added to the surface protecting layer, the undercoat layer and the blocking layer.

Examples of the solvent usable in forming the charge generating layer and/or the charge transporting layer include aromatic solvent (e.g., benzene, toluene, xylene and chlorobenzene), ketone (e.g., acetone, methyl ethyl ketone and cyclohexaneone), alcohol (e.g., methanol, ethanol and isopropanol), ester (e.g., acetic ether and ethyl cellosolve), halogenated hydrocarbon (e.g., carbon tetrachloride, carbon tetrabromide, chloroform, dichloromethane and tetrachloroethane), ether (e.g., tetrahydrofuran, dioxolane and dioxane), sulfoxide (e.g., dimethylsulfoxide), and amide (e.g., dimethylformamide and diethylformamide).One of the above solvents may be singularly used, or two or more of them may be used together as a mixture solvent.

The photosensitive layer of a single-layer electrophotographic photoreceptor can be easily formed by applying the PC resin of this exemplary embodiment as the binder resin with use of the charge generating substance, the charge transporting substance and the additive. The charge transporting substance is preferably added with at least one of the above-described hole transporting substance and an electron transporting substance. A charge transporting substance disclosed in JP 2005-139339 A can be suitably applied as the electron transporting substance.

Various coating applicators (e.g., known applicators) can perform application of each layer. Examples of such a coating applicator include an applicator, a spray coater, a bar coater, a chip coater, a roll coater, a dip coater and a doctor blade.

The thickness of the photosensitive layer of the electrophotographic photoreceptor is in a range from 5 µm to 100 µm, preferably 8 µm to 50 µm. When the thickness of the photosensitive layer of the electrophotographic photoreceptor is 5 µm or more, a decrease in the initial potential can be prevented. When the thickness of the photosensitive layer of the electrophotographic photoreceptor is 100 µm or less, degradation of the electrophotographic characteristics can be prevented. A ratio of the charge generating substance for use in manufacturing the electrophotographic photoreceptor to the binder resin is 1:99 to 30:70 by mass, more preferably 3:97 to 15:85 by mass. A ratio of the charge transporting substance to the binder resin is 10:90 to 80:20 by mass, more preferably 30:70 to 70:30 by mass.

Since the electrophotographic photoreceptor thus obtained uses the PC resin of this exemplary embodiment, a coating liquid neither whitens nor gels in manufacturing the photosensitive layer. In addition, since the PC resin of this exemplary embodiment is contained as the binder resin in the photosensitive layer, the electrophotographic photoreceptor has excellent durability (wear resistance) and electrical characteristics (electrification characteristics). Thus, the electrophotographic photoreceptor is a photoreceptor that maintains its excellent electrophotographic characteristics for a long time. Accordingly, the electrophotographic photoreceptor is suitably applicable to various electrophotographic fields such as copier (black and white copier, multi-color copier, full-color copier; analog copier, digital copier), printer (laser printer, LED printer, liquid-crystal shutter printer), facsimile, platemaker, and equipment capable of functioning as a plurality of them.

Additionally, since the PC resin (copolymerized polycarbonate resin) of this exemplary embodiment is also excellent in surface physical properties and the like, when the PC resin is used in the electrophotographic photoreceptor, it is possible to provide the electrophotographic photoreceptor excellent in cleaning characteristics. When the cleaning characteristics are at a high level, it is possible to prevent the toner adhered to the surface of the photoreceptor from passing through a cleaning blade. Additionally, filming hardly occurs on the photoreceptor.

The cleaning characteristics can be confirmed by observing the toner adhered to the surface of the photoreceptor with use of an optical microscope.

The component of the PC resin of this exemplary embodiment related to the cleaning characteristics of the electrophotographic photoreceptor is exemplified by PPE (polyphenylene ether) skeleton. Since the PPE skeleton is contained in the PC resin, excellent cleaning characteristics are exhibited.

The electrophotographic photoreceptor of this exemplary embodiment is electrified in use by corona discharge (corotron, scorotron), contact electrification (charge roll, charge brush) or the like. Examples of the charge roll include a charge roll by DC electrification and a charge roll by AC/DC superimposed electrification in which the AC voltage is superimposed. For exposure, a halogen lamp, a fluorescent lamp, laser (semiconductor, He—Ne), LED or a photoreceptor internal exposure system may be used. For image development, dry developing such as cascade developing, two-component magnetic brush developing, one-component insulating toner developing and one-component conductive toner developing, and wet developing may be used. For transfer, electrostatic transfer (e.g., corona transfer, roller transfer and belt transfer), pressure transfer and adhesive transfer may be used, for example. For fixing, heat roller fixing, radiant flash fixing, open fixing, pressure fixing and the like may be used, for example. For cleaning and neutralizing, brush cleaner, magnetic brush cleaner, electrostatic brush cleaner, magnetic roller cleaner, blade cleaner may be used, for example. Incidentally, a cleaner-less system may be used. Examples of resin for toner include styrene-base resin, styrene-acrylic base copolymer resin, polyester, epoxy resin and cyclic hydrocarbon polymer. The toner may be spherical or amorphous. The toner controlled to have a certain shape (such as spheroidal shape and potato shape) can be also used. The toner may be pulverized toner, suspension-polymerized toner, emulsion-polymerized toner, chemically-pelletized toner, or ester-elongation toner.

Structure of Electric Device

An electric device of this exemplary embodiment includes the electrophotographic photoreceptor of this exemplary embodiment (e.g., a photosensitive drum using the electrophotographic photoreceptor of this exemplary embodiment). Examples of such an electric device include a copier, a printer such as a laser printer, a fax machine, and a complex machine having the functions of the above devices.

Since the electric device of this exemplary embodiment includes the electrophotographic photoreceptor excellent in wear resistance of this exemplary embodiment, the exchange frequency of the photosensitive drum is decreased, so that the electronic device is significantly advantageous in terms of the cost.

Modification of Exemplary Embodiment

The invention is not limited to the above-described exemplary embodiment but may include modifications and improvements not hampering the achievement of an object of the invention. It should be noted that like reference characters are used to indicate the same members and the like as those described in the exemplary embodiment and the description thereof is omitted or simplified hereinbelow.

For instance, the bischloroformate composition of the invention may be a bischloroformate composition containing a bischloroformate compound represented by a formula (10) below.

[Formula 51]

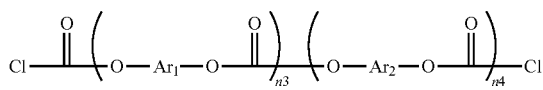

(10)

In the formula (10), $Ar_1$ means the same as $Ar_1$ in the formula (2) and $Ar_2$ means the same as $Ar_2$ in the formula (3).

n3 and n4 are each independently an integer of 1 or more. n3 is preferably an integer of 1 to 3, more preferably 1 to 2.

n4 is preferably an integer of 1 to 3, more preferably 1 to 2.

In applying conditions for reacting two or more materials (monomers) with phosgene (a method described in relation to Example(s) below), a component consisting of a dimer or a larger aggregate is sometimes partly generated. Such a partly generated component consisting of a dimer or a larger aggregate is any of a reactant of $Ar_1$ and $Ar_1$, a reactant of $Ar_1$ and $Ar_2$ (a bischloroformate compound represented by the formula (10)), and a reactant of $Ar_2$ and $Ar_2$ depending on a molar ratio of the monomers being used. For instance, when a material forming a unit of "—O—$Ar_1$—O—(C=O)—" (hereinafter referred to as "$Ar_1$ unit"), which is hereinafter referred to as "$Ar_1$ monomer", is reacted with another material forming a unit of "—O—$Ar_2$—O—(C=O)—" (hereinafter referred to as "$Ar_2$ unit"), which is hereinafter referred to as "$Ar_2$ monomer", in the same amount, a compound represented by the formula (10), in which the $Ar_1$ unit is bonded to the $Ar_2$ unit, stochastically accounts for 50% or more of the component consisting of a dimer or larger aggregate. According to a scope of the invention, at a ratio of $Ar_1/(Ar_1+Ar_2)$ closer to 50 mol %, the compound represented by the formula (10) is generated more easily as the composition is being produced more.

The composition according to the invention may be prepared by separately reacting the $Ar_1$ monomer with phosgene and the $Ar_2$ monomer with phosgene and mixing the resulting products. However, in this case, no compound represented by the formula (10) with the bonding of the $Ar_1$ unit and the $Ar_2$ unit is generated.

It should be noted that the bonding of the $Ar_1$ unit and the $Ar_2$ unit can be determined by NMR ($^1$H, $^{13}$C).

In the bischloroformate compound represented by the formula (10), the $Ar_1$ unit may be continuously present. Similarly, the $Ar_2$ unit may be continuously present. Alternatively, the $Ar_1$ unit and the $Ar_2$ unit may be present alternately or at random.

Further, for instance, the bischloroformate composition according to the invention may be a bischloroformate composition containing the bischloroformate compound represented by the formula (10), the first bischloroformate compound represented by the formula (11), and the second bischloroformate compound represented by the formula (12).

EXAMPLES

The invention will be described further in more detail with reference to Examples and Comparative Examples. Incidentally, the descriptions of Examples by no means limit the invention.

Description is first made on Example 1-1 to Example 1-12 in relation to a bischloroformate compound produced by the first production method.

Example 1-1

Bischloroformate Composition of BPZ and OCBP 28.9 g (0.108 mol) of 1,1-bis-(4-hydroxyphenyl)cyclohexane (bisphenol Z, occasionally abbreviated as "BPZ" herein), 4.7 g (0.022 mol) of 3,3'-dimethyl-4,4'-dihydroxybiphenyl (occasionally abbreviated as "OCBP" herein), 525 mL of dichloromethane (abbreviated as "MDC" hereinbelow), and 38.6 g (0.39 mol) of phosgene were mixed into a solution. To the mixed solution, a solution prepared by diluting 29.0 g (0.287 mol) of trimethylamine (abbreviated as "TEA" hereinbelow) with 100 mL of MDC was dropped in a temperature range of 8 degrees C. to 16 degrees C. over a period of 3 hours and 10 minutes. After stirred in a temperature range of 15 degrees C. to 16 degrees C. for 1 hour and 30 minutes, the reactant mixture was cleaned by adding therein 2.5 mL of concentrated hydrochloric acid and 140 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.94 mol/L, a solid content concentration of $186\times10^{-3}$ kg/L, and an average number of monomer units (m1) of 1.04.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

$Mav = 2 \times 1000/(CF\ number) = 2 \times 1000/(CF\ value/concentration) =$ $2 \times 1000/(0.94/(186 \times 10^{-3})) = 395.74$ $M1 = 393.26 \times 0.83 + 339.17 \times 0.17 = 384.06$ $M2 = M1 - Y = 384.06 - 98.92 = 285.14$ average number of monomer units $(m1) = 1 + (Mav - M1)/M2 = 1.04$ The molar composition ratio of the bischloroformate composition of this Example was calculated using $^1$H-NMR spectrum.

$Ar_1/(Ar_1+Ar_2)=83$ (mol %)

Example 1-2

Bischloroformate Composition of BPCZ and OCBP 32.0 g (0.108 mol) of 1,1-bis-(4-hydroxy-3-methylphenyl)cyclohexane (bisphenol CZ, occasionally abbreviated as "BPCZ" herein), 4.7 g (0.022 mol) of OCBP, 525 mL of MDC, and 38.6 g (0.39 mol) of phosgene were mixed into a solution. To the mixed solution, a solution prepared by diluting 29.0 g (0.287 mol) of TEA with 100 mL of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 2.5 mL of concentrated hydrochloric acid and 140 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.87 mol/L, a solid content of $178\times10^{-3}$ kg/L, and an average number of monomer units (m1) of 1.01.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=409.20
M1=407.35
M2=308.43
average number of monomer units (m1)=1.01

The molar composition ratio of the bischloroformate composition of this Example was calculated using $^1$H-NMR spectrum.

$Ar_1/(Ar_1+Ar_2)=83$ (mol %)

Example 1-3

Bischloroformate Composition of BPZ and OCBP 22.8 g (0.085 mol) of BPZ, 9.8 g (0.046 mol) of OCBP, 525 mL of MDC, and 38.6 g (0.39 mol) of phosgene were mixed into a solution. To the mixed solution, a solution prepared by diluting 29.0 g (0.287 mol) of TEA with 100 mL of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 2.5 mL of concentrated hydrochloric acid and 140 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.88 mol/L, a solid content of $173\times10^{-3}$ kg/L, and an average number of monomer units (m1) of 1.07.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=393.18
M1=374.33
M2=275.41
average number of monomer units (m1)=1.07

The molar composition ratio of the bischloroformate composition of this Example was calculated using $^1$H-NMR spectrum.

$Ar_1/(Ar_1+Ar_2)=65$ (mol %)

Example 1-4

Bischloroformate Composition of BPB and OCBP 21.3 g (0.088 mol) of 2,2-bis(4-hydroxyphenyl)butane (bisphenol B, occasionally abbreviated as "BPB" herein), 9.0 g (0.042 mol) of OCBP, 525 mL of MDC, and 38.6 g (0.39 mol) of phosgene were mixed into a solution. To the mixed solution, a solution prepared by diluting 29.0 g (0.287 mol) of TEA with 100 mL of MDC was dropped in a temperature range of 8 degrees C. to 16 degrees C. over a period of 3 hours. After stirred in a temperature range of 15 degrees C. to 16 degrees C. for 1 hour and 40 minutes, the reactant mixture was cleaned by adding therein 2.5 mL of concentrated hydrochloric acid and 140 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.84 mol/L, a solid content of $165\times10^{-3}$ kg/L, and an average number of monomer units (m1) of 1.13.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=392.86
M1=358.24
M2=259.32
average number of monomer units (m1)=1.13

The molar composition ratio of the bischloroformate composition of this Example was calculated using $^1$H-NMR spectrum.

$Ar_1/(Ar_1+Ar_2)=68$ (mol %)

Example 1-5

Bischloroformate Composition of BPZ and OCBP

In Example 1-5, triphosgene was used as a phosgene compound. 28.9 g (0.108 mol) of BPZ, 4.7 g (0.022 mol) of OCBP, and 525 mL of MDC were mixed into a solution. To the mixed solution, a solution prepared by diluting 38.7 g (0.13 mol) of triphosgene(bis(trichloromethyl)cabonate) with 200 mL of MDC was dropped in a temperature range of 3 degrees C. to 5 degrees C. over a period of 26 minutes. To the mixed solution, another mixed solution of 29.0 g (0.287 mol) of TEA and 70 ml of MDC was dropped in a temperature range of 11 degrees C. to 18 degrees C. over a period of 3 hours. After the mixed solution was fully dropped, the reactant mixture was stirred in a temperature range of 17 degrees C. to 17.5 degrees C. for 1 hour and then cleaned by adding therein 2.4 mL of concentrated hydrochloric acid and 140 mL of deionized water. Washing with water was then repeated until an aqueous layer became neutral. After the washing with water, an MDC layer was taken out and condensed under a reduced pressure. The thus-obtained bischloroformate-composition-containing solution had a CF value of 0.90 mol/L, a solid content of $180 \times 10^{-3}$ kg/L, and an average number of monomer units (m1) of 1.06.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=400.00
M1=383.52
M2=284.60
average number of monomer units (m1)=1.06

The molar composition ratio of the bischloroformate composition of this Example was calculated using $^1$H-NMR spectrum.

$Ar_1/(Ar_1+Ar_2)=82$(mol %)

Example 1-6: Bischloroformate Composition of BPZ and OCBP 136 g (0.51 mol) of BPZ, 58 g (0.27 mol) of OCBP, 3.15 L of MDC, and 232 g (2.3 mol) of phosgene were mixed into a solution. To the mixed solution, a solution prepared by diluting 174 g (1.72 mol) of TEA with 0.6 L of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 15 mL of concentrated hydrochloric acid and 840 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.57 mol/L, a solid content of $110 \times 10^{-3}$ kg/L, and an average number of monomer units (m1) of 1.04.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=385.96
M1=374.33
M2=275.41
average number of monomer units (m1)=1.04

The molar composition ratio of the bischloroformate composition of this Example was calculated using $^1$H-NMR spectrum.

$Ar_1/(Ar_1+Ar_2)=65$(mol %)

Example 1-7

Bischloroformate Composition of BPCZ and OCBP 23.1 g (0.078 mol) of BPCZ, 11.1 g (0.052 mol) of OCBP, 525 mL of MDC, and 38.6 g (0.39 mol) of phosgene were mixed into a solution. To the mixed solution, a solution prepared by diluting 29.0 g (0.287 mol) of TEA with 100 mL of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 2.5 mL of concentrated hydrochloric acid and 140 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.76 mol/L, a solid content of $148 \times 10^{-3}$ kg/L, and an average number of monomer units (m1) of 1.01.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=391.53
M1=388.12
M2=289.20
average number of monomer units (m1)=1.01

The molar composition ratio of the bischloroformate composition of this Example was calculated using $^1$H-NMR spectrum.

$Ar_1/(Ar_1+Ar_2)=60$(mol %)

Example 1-8

Bischloroformate Composition of BPZ and OCBP 142 g (0.53 mol) of BPZ, 54 g (0.25 mol) of OCBP, 3.15 L of MDC, and 232 g (2.3 mol) of phosgene were mixed into a solution. To the mixed solution, a solution prepared by diluting 174 g (1.72 mol) of TEA with 0.6 L of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 15 mL of concentrated hydrochloric acid and 840 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.57 mol/L, a solid content of $111 \times 10^{-3}$ kg/L, and an average number of monomer units (m1) of 1.05.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=388.75
M1=375.64
M2=276.72
average number of monomer units (m1)=1.05

The molar composition ratio of the bischloroformate composition of this Example was calculated using $^1$H-NMR spectrum.

$Ar_1/(Ar_1+Ar_2)=68$(mol %)

Example 1-9

Bischloroformate Composition of BPZ and OCBP 147 g (0.55 mol) of BPZ, 49 g (0.23 mol) of OCBP, 3.15 L of MDC, and 232 g (2.3 mol) of phosgene were mixed into a solution. To the mixed solution, a solution prepared by diluting 174 g (1.72 mol) of TEA with 0.6 L of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 15 mL of concentrated hydrochloric acid and 840 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.58 mol/L, a solid content of $114 \times 10^{-3}$ kg/L, and an average number of monomer units (m1) of 1.05.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=390.41
M1=377.26
M2=278.34
average number of monomer units (m1)=1.05

The molar composition ratio of the bischloroformate composition of this Example was calculated using $^1$H-NMR spectrum.

$Ar_1/(Ar_1+Ar_2)=71$(mol %)

Example 1-10

Bischloroformate Composition of BPCZ and OCBP 21.2 g (0.072 mol) of BPCZ, 12.5 g (0.059 mol) of OCBP, 525 mL of MDC, and 38.6 g (0.39 mol) of phosgene were mixed into a solution. To the mixed solution, a solution prepared by diluting 29.0 g (0.287 mol) of TEA with 100 mL of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 2.5 mL of concentrated hydrochloric acid and 140 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.73 mol/L, a solid content of $141 \times 10^{-3}$ kg/L, and an average number of monomer units (m1) of 1.01.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=387.36
M1=384.02
M2=285.10
average number of monomer units (m1)=1.01

The molar composition ratio of the bischloroformate composition of this Example was calculated using $^1$H-NMR spectrum.

$Ar_1/(Ar_1+Ar_2)=55$(mol %)

Example 1-11

Bischloroformate Composition of BPCZ and OCBP 19.2 g (0.065 mol) of BPCZ, 13.9 g (0.065 mol) of OCBP, 525 mL of MDC, and 38.6 g (0.39 mol) of phosgene were mixed into a solution. To the mixed solution, a solution prepared by diluting 29.0 g (0.287 mol) of TEA with 100 mL of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 2.5 mL of concentrated hydrochloric acid and 140 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.70 mol/L, a solid content of $134 \times 10^{-3}$ kg/L, and an average number of monomer units (m1) of 1.01.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=381.77
M1=379.92
M2=281.00
average number of monomer units (m1)=1.01

The molar composition ratio of the bischloroformate composition of this Example was calculated using $^1$H-NMR spectrum.

$Ar_1/(Ar_1+Ar_2)=50$(mol %)

Example 1-12

Bischloroformate Composition of BPCZ and OCBP 25.8 g (0.087 mol) of BPCZ, 9.2 g (0.043 mol) of OCBP, 525 mL of MDC, and 38.6 g (0.39 mol) of phosgene were mixed into a solution. To the mixed solution, a solution prepared by diluting 29.0 g (0.287 mol) of TEA with 100 mL of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 2.5 mL of concentrated hydrochloric acid and 140 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.80 mol/L, a solid content of $159 \times 10^{-3}$ kg/L, and an average number of monomer units (m1) of 1.01.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=397.50
M1=393.86
M2=294.94
average number of monomer units (m1)=1.01

The molar composition ratio of the bischloroformate composition of this Example was calculated using $^1$H-NMR spectrum.

$Ar_1/(Ar_1+Ar_2) = 67 (mol\%)$

Comparative Example

Bischloroformate Composition of BPCZ and OCBP 15.4 g (0.052 mol) of BPCZ, 16.7 g (0.078 mol) of OCBP, 525 mL of MDC, and 38.6 g (0.39 mol) of phosgene were mixed into a solution. To the mixed solution, a solution prepared by diluting 29.0 g (0.287 mol) of TEA with 100 mL of MDC was dropped in a temperature range of 8 degrees C. to 16 degrees C. over a period of 3 hours and 10 minutes. After stirred in a temperature range of 15 degrees C. to 16 degrees C. for 1 hour and 40 minutes, the reactant mixture was cleaned by adding therein 2.5 mL of concentrated hydrochloric acid and 140 mL of deionized water. Washing with water was then repeated until an aqueous layer became neutral. After the aqueous layer became neutral, an MDC layer was condensed under a reduced pressure. The thus-obtained bischloroformate-composition-containing solution had a CF value of 0.66 mol/L, a solid content of $122 \times 10^{-3}$ kg/L, and an average number of monomer units (m1) of 1.00.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=371.95
M1=371.72
M2=272.80
average number of monomer units (m1)=1.00

The molar composition ratio of the bischloroformate composition of this
Example was calculated using $^1$H-NMR spectrum.

$Ar_1/(Ar_1+Ar_2) = 40 (mol\%)$

Description is next made on Example 2-1 in relation to a bischloroformate composition produced by the second production method.

Example 2-1

Bischloroformate Composition of BPZ and OCBP 59.8 g (0.223 mol) of BPZ, 11.6 g (0.054 mol) of OCBP, and 510 mL of MDC were mixed into a suspension and 55.3 g (0.546 mol) of TEA was mixed and dissolved in the suspension. In a solution prepared by dissolving 54.5 g (0.551 mol) of phosgene in 225 mL of MDC, the mixture was dropped in a temperature range of 14 degrees C. to 18.5 degrees C. over a period of 2 hours and 50 minutes. After the mixture was fully dropped, the solution was stirred in a temperature range of 18.5 degrees C. to 19 degrees C. for 1 hour, cleaned by adding 4.5 mL of concentrated hydrochloric acid and 73 mL of deionized water, and repeatedly washed with water until an aqueous layer became neutral. An MDC layer was then taken out and condensed under a reduced pressure. The thus-obtained bischloroformate-composition-containing solution had a CF value of 0.92 mol/L, a solid content of $183 \times 10^{-3}$ kg/L, and an average number of monomer units (m1) of 1.05.

The CF value was calculated by quantifying chlorine ions liberated by hydrolysis. The solid content concentration was determined by measuring the amount of a solid residue after removal of the solvent from the solution. The average number of monomer units (m1) was calculated with Y=98.92.

Mav=397.83
M1=383.52
M2=284.60
average number of monomer units (m1)=1.05

The molar composition ratio of the bischloroformate composition of this
Example was calculated using $^1$H-NMR spectrum.

$Ar_1/(Ar_1+Ar_2) = 81 (mol\%)$

Description is next made on Example 3-1 in relation to a bischloroformate compound produced by the third production method.

Example 3-1

Bischloroformate Composition of BPZ and OCBP 59.8 g (0.223 mol) of BPZ, 11.6 g (0.054 mol) of OCBP, and 510 mL of MDC were mixed into a suspension and 55.3 g (0.546 mol) of TEA was mixed and dissolved in the suspension. A solution prepared by dissolving 54.5 g (0.551 mol) of phosgene in 225 mL of MDC was dropped into the mixture in a temperature range of 14 degrees C. to 18.5 degrees C. over a period of 2 hours and 50 minutes. After the mixture was fully dropped, the solution was stirred in a temperature range of 18.5 degrees C. to 19 degrees C. for 1 hour, cleaned by adding 4.5 mL of concentrated hydrochloric acid and 73 mL of deionized water, and repeatedly washed with water until an aqueous layer became neutral. An MDC layer was then taken out and condensed under a reduced pressure. The thus-obtained bischloroformate-composition-containing solution had a CF value of 0.89 mol/L, a solid content of $180 \times 10^{-3}$ kg/L, and an average number of monomer units (m1) of 1.07.

The CF value was calculated by quantifying chlorine ions liberated by hydrolysis. The solid content concentration was determined by measuring the amount of a solid residue after removal of the solvent from the solution. The average number of monomer units (m1) was calculated with Y=98.92.

Mav=404.49
M1=383.52
M2=284.60
average number of monomer units (m1)=1.07

The molar composition ratio of the bischloroformate composition of this
Example was calculated using $^1$H-NMR spectrum.

$Ar_1/(Ar_1+Ar_2) = 81 (mol\%)$

Comparative Example 1

(1) Synthesis of OCBP Bischloroformate Compound 150.0 g (0.701 mol) of OCBP was suspended with 1100 mL of methylene chloride and then 186 g (1.88 mol) of phosgene was added and dissolved therein. To this solution, another solution prepared by dissolving 199.4 g (1.97 mol) of triethylamine in 460 mL of methylene chloride was dropped in a temperature range of 13 degrees C. to 16 degrees C. over a period of 2 hours and 50 minutes. The reactant mixture was stirred in a temperature range of 14 degrees C. to 16 degrees C. for 30 minutes. 5.0 mL of concentrated hydrochloric acid and 200 mL of deionized water were added to the reactant mixture for cleaning. Subsequently, washing with water was repeated until an aqueous layer becme neutral, thus preparing a methylene chloride solution of an OCBP bischloroformate compound having a chloroformate group at its molecular end. The obtained solution had a CF value of 0.53 mol/L, a solid content concentration of $92 \times 10^{-3}$ kg/L, and an average number of monomer units of 1.03.

The CF value was calculated by quantifying chlorine ions liberated by hydrolysis. The solid content concentration was determined by measuring the amount of a solid residue after removal of the solvent from the solution.

The average number of monomer units of the bischloroformate compound of Comparative Example 1 was calculated using the expression (Numerical Expression 1), in which M1 is "a molecular weight determined when the OCBP bischloroformate compound has one monomer unit", the CF number is "CF value/concentration", the CF value is "a mole number of a chlorine atom(s) in the OCBP bischloroformate compound contained in 1 L of the reaction solution", the concentration is "the amount of a solid content obtained by condensing 1 L of the reaction solution", and Y is "the total atom weight of two chlorine atoms, one oxygen atom, and one carbon atom" (=98.92).

Mav=347.17
M1=339.17
M2=240.25
average number of monomer units (m1)=1.03

Description is next made on Example 4-1 in relation to a bischloroformate compound produced by the fourth production method.

Example 4-1

Bischloroformate Composition of BPZ and OCBP

The OCBP bischloroformate solution of Comparative Example 1 was mixed with a BPZ bischloroformate solution with a chloroformate concentration of 1.01 mol/L, a solid content concentration of $209 \times 10^{-3}$ kg/L, and an average number of monomer units of 1.02 at a ratio of OCBP bischloroformate : BPZ bischloroformate=30 mass % : 70 mass %. The mixed solution was then condensed under a reduced pressure, thus preparing a bischloroformate-composition-containing solution. The bischloroformate-composition-containing solution had a CF value of 0.87 mol/L, a solid content of $174 \times 10^{-3}$ kg/L, and an average number of monomer units (m1) of 1.05.

The CF value was calculated by quantifying chlorine ions liberated by hydrolysis of a chloroformate group. The solid content concentration was determined by measuring the amount of a solid residue after removal of the solvent from the solution. The average number of monomer units (m1) was calculated with Y=98.92.

Mav=400.00
M1=384.61
M2=285.69
average number of monomer units (m1)=1.05

The molar composition ratio of the bischloroformate composition of this Example was calculated using $^1$H-NMR spectrum.

$$Ar_1/(Ar_1+Ar_2)=82 \text{(mol \%)}$$

TABLE 1

|  | M1 | CF Value [mol/L] | Solid Content Concentration [kg/L] | CF Number | Average Number of Monomer Units (ml) | $Ar_1/(Ar_1 + Ar_2)$ [mol %] |
|---|---|---|---|---|---|---|
| Ex. 1-1 | 384.06 | 0.94 | $186 \times 10^{-3}$ | 5.05 | 1.04 | 83 |
| Ex. 1-2 | 407.35 | 0.87 | $178 \times 10^{-3}$ | 4.89 | 1.01 | 83 |
| Ex. 1-3 | 374.33 | 0.88 | $173 \times 10^{-3}$ | 5.09 | 1.07 | 65 |
| Ex. 1-4 | 358.24 | 0.84 | $165 \times 10^{-3}$ | 5.09 | 1.13 | 68 |
| Ex. 1-5 | 383.52 | 0.90 | $180 \times 10^{-3}$ | 5.00 | 1.06 | 82 |
| Ex. 2-1 | 383.52 | 0.92 | $183 \times 10^{-3}$ | 5.03 | 1.05 | 82 |
| Ex. 3-1 | 383.52 | 0.89 | $180 \times 10^{-3}$ | 4.94 | 1.07 | 82 |
| Ex. 4-1 | 384.61 | 0.87 | $174 \times 10^{-3}$ | 5.00 | 1.05 | 82 |
| Comp. 1 | 339.17 | 0.53 | $92 \times 10^{-3}$ | 5.76 | 1.03 | 0 |

Evaluation

A bischloroformate compound having a biphenol skeleton such as OCBP is less soluble in an organic solvent and thus disadvantageous in solution stability. Further, the use of such a bischloroformate compound for producing a polymer lowers the stability in producing the polymer (molecular weight stability). Accordingly, the bischloroformate compositions each having the OCBP skeleton (Examples 1-1 to 1-5 and 2-1 to 4-1) and the OCBP bischloroformate compound (Comparative Example 1) were evaluated in terms of the above characteristics.

Evaluation 1: Solubility Test

An MDC solution of each of the bischloroformate compositions of Examples 1-1 to 1-5 and 2-1 to 4-1 and the OCBP bischloroformate compound of Comparative Example 1 was adjusted to a predetermined concentration at 23 degrees C. and visually checked for the solubility of a solid content therein. A transparent solution was ranked as "A" and a solution with the precipitation of a solid content was ranked as "B". Table 2 shows the results.

TABLE 2

|  | Concentration | | | | |
|---|---|---|---|---|---|
|  | 80 [g/L] | 90 [g/L] | 100 [g/L] | 130 [g/L] | 160 [g/L] |
| Ex. 1-1 | A | A | A | A | A |
| Ex. 1-2 | A | A | A | A | A |

TABLE 2-continued

|  | Concentration | | | | |
|---|---|---|---|---|---|
|  | 80 [g/L] | 90 [g/L] | 100 [g/L] | 130 [g/L] | 160 [g/L] |
| Ex. 1-3 | A | A | A | A | A |
| Ex. 1-4 | A | A | A | A | A |
| Ex. 1-5 | A | A | A | A | A |
| Ex. 2-1 | A | A | A | A | A |
| Ex. 3-1 | A | A | A | A | A |
| Ex. 4-1 | A | A | A | A | A |
| Comp. 1 | A | A | B | B | B |

As shown in Table 2, the precipitation of a solid content was found in the OCBP bischloroformate compound of Comparative Example 1 at a solid content concentration of 100 (g/L) or more.

In contrast, the bischloroformate composition of each of Examples 1-1 to 1-5 and 2-1 to 4-1 was transparent at any solid content concentration, thus proving to be highly soluble.

Evaluation 2: Solution Stability Test

An MDC solution of each of the bischloroformate compositions of Examples 1-1 to 1-5 and 2-1 to 4-1 and the OCBP bischloroformate compound of Comparative Example 1 was adjusted to 90 (g/L), and then visually checked for the precipitation of a solid content therein after being stored at 5 degrees C. for three months. A transparent solution was ranked as "C" and a solution with the precipitation of a solid content was ranked as "D". Table 3 shows the results.

TABLE 3

|  | Concentration 90 [g/L] |
|---|---|
| Ex. 1-1 | C |
| Ex. 1-2 | C |
| Ex. 1-3 | C |
| Ex. 1-4 | C |
| Ex. 1-5 | C |
| Ex. 2-1 | C |
| Ex. 3-1 | C |
| Ex. 4-1 | C |
| Comp. 1 | D |

As shown in Table 3, the precipitation of a solid content was found in the OCBP bischloroformate compound of Comparative Example 1.The MDC solution of the OCBP bischloroformate compound of Comparative Example 1 is almost saturated even at a solid content concentration of 90 (g/L). Accordingly, the solution is inferred to be easily affected by environmental changes and, consequently, tend to experience the precipitation of fine crystal.

In contrast, the bischloroformate composition of each of Examples 1-1 to 1-5 and 2-1 to 4-1 was still transparent after being stored for three months. The bischloroformate composition of each of Examples 1-1 to 1-5 and 2-1 to 4-1 is inferred to exhibit a stable solid content concentration in the solution, since it is highly soluble.

Evaluation 3: Production Stability Test

Example 5

Methylene chloride (184 mL) was added to the bischloroformate-composition-containing solution (173.1 mL) of Example 1-1 to adjust the solid content concentration of the bischloroformate composition to 90 (g/L). To the obtained solution, p-tert-butylphenol (hereinafter occasionally abbreviated as "PTBP") (0.243 g) as a terminal terminator was added and stirred for sufficient mixing. After a temperature inside the reactor was cooled down to 15 degrees C., an entire amount of the prepared divalent phenol solution was added to the obtained solution, to which 1.5 mL of a triethylamine aqueous solution (7 vol %) was added with stirring and kept on stirring for one hour.

As the above-described dihydric phenol solution, a solution was prepared by cooling 120 mL (sodium hydroxide 10.5 g) of a 1.5N sodium hydroxide solution to a room temperature or below, adding therein 0.30 g of hydrosulfite as an antioxidant and 17.4 g of 3,3'-dimethyl-4,4'-dihydroxybiphenyl, and fully dissolving these antioxidants.

The obtained reactant mixture was diluted with 0.6 L of methylene chloride and 0.05 L of water and cleaned. A lower layer was separated from the reactant mixture. Then, the reactant mixture was cleaned with 0.17 L of water one time, with 0.1 L of 0.03N hydrochloric acid one time, and with 0.17 L of water three times in this order. The obtained methylene chloride solution was dropped into methanol with stirring. The obtained redeposit was filtered and dried to obtain a PC copolymer with a structure represented by a formula (PC-1) below. A copolymerization ratio of the PC copolymer of this Example was calculated through analysis with reference to the $^1$H-NMR spectrum. Table 4 shows the results.

Further, to evaluate the polymerization stability, the polymerization was performed three times under the above-described conditions and the PC copolymer of this Example was examined in terms of a variation in the viscosity average molecular weight. Table 5 shows the results.

[Formula 52]

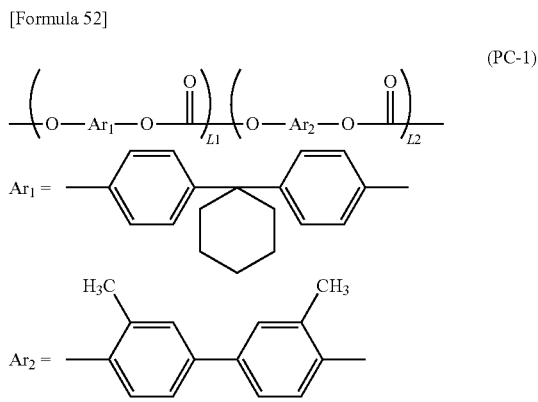

The viscosity average molecular weight (Mv) of the PC copolymer of this Example was calculated as follows.

First, a sample of the PC copolymer of this Example was dissolved in methylene chloride to prepare a solution with a concentration of 0.5 g/dL and an intrinsic viscosity [η] of the solution at a temperature of 20 degrees C. was calculated using an Ubbelohde viscometer. Second, the calculated intrinsic viscosity [η] was converted to Mv by the following Schnell's formula.

$$[\eta] = 1.23 \times 10^{-5} \, Mv^{0.83}$$

Comparative Example 2

Methylene chloride (175 mL) was further added to the methylene chloride solution (297.7 mL) of the OCBP bischloroformate compound of Comparative Example 1 to adjust the solid content concentration of the OCBP bischloroformate compound to 58 (g/L). To this solution, PTBP (0.195 g) was added as a terminal terminator and stirred for sufficient mixing. After a temperature inside the reactor was cooled down to 15 degrees C., an entire amount of the prepared divalent phenol solution was added to the obtained solution, to which 1.5 mL of a triethylamine aqueous solution (7 vol %) was added with stirring and kept on stirring for one hour.

As the above-described dihydric phenol solution, a solution was prepared by cooling 160 mL (potassium hydroxide 13.4 g) of a 1.3N potassium hydroxide solution to a room temperature or below, adding therein 0.15 g of hydrosulfite as an antioxidant and 21.2 g of 1,1-bis(4-hydroxyphenyl)cyclohexane, and fully dissolving these antioxidants.

The obtained reactant mixture was diluted with 0.75 L of methylene chloride and 0.06 L of water and cleaned. A lower layer was separated from the reactant mixture. Then, the reactant mixture was cleaned with 0.22 L of water one time, with 0.1 L of 0.03N hydrochloric acid one time, and with 0.22 L of water three times in this order. The obtained methylene chloride solution was dropped into methanol with stirring. The obtained redeposit was filtered and dried to obtain a PC copolymer with a structure represented by the formula (PC-1). A copolymerization ratio of the PC copolymer of this Comparative Example was calculated through analysis with reference to the $^1$H-NMR spectrum. Table 4 shows the results.

Further, to evaluate the polymerization stability, the polymerization was performed three times under the above-described conditions and the PC copolymer of this Comparative Example was examined in terms of a variation in the viscosity average molecular weight. Table 5 shows the results.

The viscosity average molecular weight (Mv) of the PC copolymer of this Comparative Example was calculated in the same manner as in Example 5.

TABLE 4

| Copolymerization Ratio of PC Copolymer (L2/(L1 + L2)) | | |
|---|---|---|
| 1st Polymerization | 2nd Polymerization | 3rd Polymerization |
| Ex. 5 | 0.52 | 0.52 | 0.52 |
| Comp. 2 | 0.52 | 0.50 | 0.54 |

TABLE 5

| Viscosity Average Molecular Weight of PC Copolymer (Mv) | | | |
|---|---|---|---|
| 1st Polymerization | 2nd Polymerization | 3rd Polymerization | Standard Deviation |
| Ex. 5 | 61200 | 61000 | 61400 | 200 |
| Comp. 2 | 60200 | 63100 | 59000 | 2100 |

As shown in Table 5, the PC copolymer (polymer) of Comparative Example 2 had a variation in molecular weight. The MDC solution of the OCBP bischloroformate compound of Comparative Example 1 is almost saturated even at a solid content concentration of 90 (g/L). Thus, the solution is easily affected by environmental changes and, consequently, tends to experience the precipitation of fine crystal as described above. The solid content concentration thus becomes unstable, which is supposed to be a cause of a poor polymerization balance in producing a PC copolymer (polymer) and, consequently, an unstable molecular weight.

In contrast, the PC copolymer (polymer) of Example 5 was found stable in molecular weight. The bischloroformate composition of Example 1-1 is highly soluble and thus stable in solid content concentration in the solution as described above. Accordingly, the molecular weight is supposed to be stable.

Example 6

Methylene chloride (358 g) was added to the bischloroformate-composition-containing solution (1752 g) of Example 1-6 to adjust the solid content concentration of the bischloroformate composition to 90 (g/L). To this solution, PTBP (1.31 g) was added as a terminal terminator and stirred for sufficient mixing. After a temperature inside the reactor was cooled down to 10 degrees C., an entire amount of the prepared divalent phenol solution was added to the obtained solution, to which 10 mL of a triethylamine aqueous solution (7 vol %) was added with stirring and kept on stirring for one hour.

As the above-described dihydric phenol solution, a solution was prepared by cooling 596 g (sodium hydroxide 54.1 g) of a 2.5N sodium hydroxide solution to a room temperature or below, adding therein 1.0 g of hydrosulfite as an antioxidant and 80.9 g of 3,3'-dimethyl-4,4'-dihydroxybiphenyl, and fully dissolving these antioxidants.

The obtained reactant mixture was diluted with 3 L of methylene chloride and 1 L of water and cleaned. A lower layer was separated from the reactant mixture. Then, the reactant mixture was cleaned with 1 L of water one time, with 1 L of 0.03N hydrochloric acid one time, and with 1 L of water three times in this order. The obtained methylene chloride solution was dropped into methanol with stirring. The obtained redeposit was filtered and dried to obtain a PC copolymer with a structure represented by a formula (PC-2) below. A viscosity average molecular weight (Mv) of the PC copolymer of this Example calculated in the same manner as in Example 5 was 62,000. A copolymerization ratio of the PC copolymer of this Example was calculated through analysis with reference to the $^1$H-NMR spectrum. Table 6 shows the results.

[Formula 53]

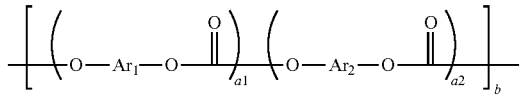

(PC-2)

Respective average chain lengths (a1, a2) of the repetition components $Ar_1$, $Ar_e$ of the obtained PC copolymer were measured by $^{13}$C-NMR. Table 6 shows the results. The details of the measurement, such as a measurement device, are as follows.

Measurement Device
   Device: DRX500 manufactured by Bruker BioSpin AG
   Measurement probe: 5-mm TCI CryroProbe
Measurement Conditions
   Amount of sample: approximately 50 mg
   Solvent: CDCl$_3$
   Measurement method: $^{13}$C-NMR (reverse gate decoupling method)

$^{13}$C resonance frequency: 125 MHz
Frequency of integration: 1024 times
The number of data points: 64 KB
Data point interval: 16.65 μsec
Pulse repetition time: 10 sec
Measurement temperature: 25 degrees C.
Measurement center frequency: 100 ppm
Measurement range: 238 ppm Analyzing Conditions In the $^{13}$C-NMR spectrum, middle one of three peaks attributed to chloroform is set at 77.23 ppm.

At that time, the values of integration of the respective peaks in the following ranges are represented as [1] (BPZ/BPZ), [2] (BPZ/OCBP), and

[3] (OCBP/OCBP).

[1]: 152.3 to 152.2 ppm
[2]: 152.1 to 151.9 ppm
[3]: 151.9 to 151.7 ppm

In this case, the respective dyad chain fractions (mol %) are as follows.

BPZ/BPZ=100×[1]/([1]+[2]+[3])
BPZ/OCBP=100×[2]/([1]+[2]+[3])
OCBP/OCBP=100×[3]/([1]+[2]+[3])

Example 7

Methylene chloride (31 g) was added to the bischloroformate-composition-containing solution (47.4 g) of Example 1-7 to adjust the solid content concentration of the bischloroformate composition to 90 (g/L). To this solution, PTBP (0.051 g) was added as a terminal terminator and stirred for sufficient mixing. After a temperature inside the reactor was cooled down to 10 degrees C., an entire amount of the prepared divalent phenol solution was added to the obtained solution, to which 0.4 mL of a triethylamine aqueous solution (7 vol %) was added with stirring and kept on stirring for one hour.

As the above-described dihydric phenol solution, a solution was prepared by cooling 22 g (sodium hydroxide 2.0 g) of a 2.5N sodium hydroxide solution to a room temperature or below, adding therein 0.1 g of hydrosulfite as an antioxidant and 3.0 g of 3,3'-dimethyl-4,4'-dihydroxybiphenyl, and fully dissolving these antioxidants.

The obtained reactant mixture was diluted with 500 mL of methylene chloride and 100 mL of water and cleaned. A lower layer was separated from the reactant mixture. Then, the reactant mixture was cleaned with 500 mL of water one time, with 500 mL of 0.03N hydrochloric acid one time, and with 500 mL of water three times in this order. The obtained methylene chloride solution was dropped into methanol with stirring. The obtained redeposit was filtered and dried to obtain a PC copolymer with a structure represented by the formula (PC-2). A viscosity average molecular weight (Mv) of the PC copolymer of this Example calculated in the same manner as in Example 5 was 62,000. A copolymerization ratio of the PC copolymer of this Example was calculated through analysis with reference to the $^1$H-NMR spectrum. Table 6 shows the results.

Respective average chain lengths (a1, a2) of the repetition components $Ar_1$, $Ar_e$ of the obtained PC copolymer were measured by $^{13}$C-NMR. Table 6 shows the results. The details of the measurement, such as a measurement device, are as follows.

Measurement Device
  Device: JNM-ECA500 manufactured by JEOL Ltd.
Measurement Conditions
  Amount of sample: approximately 250 mg
  Solvent: 3 mL of $CDCl_3$
  $^{13}$C resonance frequency: 125 MHz
  Frequency of integration: 5000 times
Analyzing Conditions In the $^{13}$C-NMR spectrum, middle one of three peaks attributed to chloroform is set at 77.07 ppm.

An o-methyl group (16.21 ppm) near a central carbonate bonding in a structure where OCBPs are adjacent to each other, an o-methyl group (16.37 ppm) near a central carbonate bonding in a structure where OC-Zs are adjacent to each other, and an o-methyl group (16.18 ppm, 16.40 ppm) near a central carbonate bonding in a structure where OC-BP is adjacent to OC-Z are different in chemical shift at the peak. Accordingly, ratios of (BPCZ/BPCZ), (BPCZ/OCBP) and (OCBP/OCBP) were calculated from the respective peak areas of o-methyl groups of an OC-BP component and an OC-Z component, which are different in detection position.

At that time, the values of integration of the respective peaks in the following ranges are represented as [1] (BPCZ/BPCZ), [2] (BPCZ/OCBP), and [3] (OCBP/OCBP).

[1]: 16.37 ppm
[2]: 16.18 ppm+16.40 ppm
[3]: 16.21 ppm

In this case, the respective dyad chain fractions (mol %) are as follows.

BPCZ/BPCZ=100×[1]/([1]+[2]+[3])
BPCZ/OCBP=100×[2]/([1]+[2]+[3])
OCBP/OCBP=100×[3]/([1]+[2]+[3])

Example 8

Methylene chloride (102 g) was added to the bischloroformate-composition-containing solution (445 g) of Example 1-8 to adjust the solid content concentration of the bischloroformate composition to 90 (g/L). To this solution, PTBP (0.34 g) was added as a terminal terminator and stirred for sufficient mixing. After a temperature inside the reactor was cooled down to 10 degrees C., an entire amount of the prepared divalent phenol solution was added to the obtained solution, to which 3 mL of a triethylamine aqueous solution (7 vol %) was added with stirring and kept on stirring for one hour.

As the above-described dihydric phenol solution, a solution was prepared by cooling 155 g (sodium hydroxide 14.1 g) of a 2.5N sodium hydroxide solution to a room temperature or below, adding therein 1.0 g of hydrosulfite as an antioxidant and 20.9 g of 3,3'-dimethyl-4,4'-dihydroxybiphenyl, and fully dissolving these antioxidants.

The obtained reactant mixture was diluted with 1 L of methylene chloride and 1 L of water and cleaned. A lower layer was separated from the reactant mixture. Then, the reactant mixture was cleaned with 1 L of water one time, with 1 L of 0.03N hydrochloric acid one time, and with 1 L of water three times in this order. The obtained methylene chloride solution was dropped into methanol with stirring. The obtained redeposit was filtered and dried to obtain a PC copolymer with a structure represented by the formula (PC-2). A viscosity average molecular weight (Mv) of the PC copolymer of this Example calculated in the same manner as in Example 5 was 62,000. A copolymerization ratio of the PC copolymer of this Example was calculated through analysis with reference to the $^1$H-NMR spectrum. Table 6 shows the results.

Respective average chain lengths (a1, a2) of the repetition components $Ar_1$, $Ar_2$ of the obtained PC copolymer were measured in the same manner as in Example 6. Table 6 shows the results.

Example 9

Methylene chloride (102 g) was added to the bischloroformate-composition-containing solution (430 g) of Example 1-9 to adjust the solid content concentration of the bischloroformate composition to 90 (g/L). To this solution, PTBP (0.34 g) was added as a terminal terminator and stirred for sufficient mixing. After a temperature inside the reactor was cooled down to 10 degrees C., an entire amount of the prepared divalent phenol solution was added to the obtained solution, to which 3 mL of a triethylamine aqueous solution (7 vol %) was added with stirring and kept on stirring for one hour.

As the above-described dihydric phenol solution, a solution was prepared by cooling 155 g (sodium hydroxide 14.5 g) of a 2.5N sodium hydroxide solution to a room temperature or below, adding therein 0.3 g of hydrosulfite as an antioxidant and 21.5 g of 3,3'-dimethyl-4,4'-dihydroxybiphenyl, and fully dissolving these antioxidants.

The obtained reactant mixture was diluted with 1 L of methylene chloride and 1 L of water and cleaned. A lower layer was separated from the reactant mixture. Then, the reactant mixture was cleaned with 1 L of water one time, with 1 L of 0.03N hydrochloric acid one time, and with 1 L of water three times in this order. The obtained methylene chloride solution was dropped into methanol with stirring. The obtained redeposit was filtered and dried to obtain a PC copolymer with a structure represented by the formula (PC-2). A viscosity average molecular weight (Mv) of the PC copolymer of this Example calculated in the same manner as in Example 5 was 62,000. A copolymerization ratio of the PC copolymer of this Example was calculated through analysis with reference to the $^1$H-NMR spectrum. Table 6 shows the results.

Respective average chain lengths (a1, a2) of the repetition components $Ar_1$, $Ar_2$ of the obtained PC copolymer were measured in the same manner as in Example 6. Table 6 shows the results.

Example 10

Methylene chloride (29 g) was added to the bischloroformate-composition-containing solution (49.8 g) of Example 1-10 to adjust the solid content concentration of the bischloroformate composition to 90 (g/L). To this solution, PTBP (0.050 g) was added as a terminal terminator and stirred for sufficient mixing. After a temperature inside the reactor was cooled down to 10 degrees C., an entire amount of the prepared divalent phenol solution was added to the obtained solution, to which 0.4 mL of a triethylamine aqueous solution (7 vol %) was added with stirring and kept on stirring for one hour.

As the above-described dihydric phenol solution, a solution was prepared by cooling 22 g (sodium hydroxide 2.0 g) of a 2.5N sodium hydroxide solution to a room temperature or below, adding therein 0.1 g of hydrosulfite as an antioxidant and 3.0 g of 3,3'-dimethyl-4,4'-dihydroxybiphenyl, and fully dissolving these antioxidants.

The obtained reactant mixture was diluted with 500 mL of methylene chloride and 100 mL of water and cleaned. A lower layer was separated from the reactant mixture. Then, the reactant mixture was cleaned with 500 mL of water one time, with 500 mL of 0.03N hydrochloric acid one time, and with 500 mL of water three times in this order. The obtained methylene chloride solution was dropped into methanol with stirring. The obtained redeposit was filtered and dried to obtain a PC copolymer with a structure represented by the formula (PC-2). A viscosity average molecular weight (Mv) of the PC copolymer of this Example calculated in the same manner as in Example 5 was 62,000. A copolymerization ratio of the PC copolymer of this Example was calculated through analysis with reference to the $^1$H-NMR spectrum. Table 6 shows the results.

Respective average chain lengths (a1, a2) of the repetition components $Ar_1$, $Ar_2$ of the obtained PC copolymer were measured in the same manner as in Example 7. Table 6 shows the results.

Example 11

Methylene chloride (26 g) was added to the bischloroformate-composition-containing solution (52.4 g) of Example 1-11 to adjust the solid content concentration of the bischloroformate composition to 90 (g/L). To this solution, PTBP (0.050 g) was added as a terminal terminator and stirred for sufficient mixing. After a temperature inside the reactor was cooled down to 10 degrees C., an entire amount of the prepared divalent phenol solution was added to the obtained solution, to which 0.4 mL of a triethylamine aqueous solution (7 vol %) was added with stirring and kept on stirring for one hour.

As the above-described dihydric phenol solution, a solution was prepared by cooling 22 g (sodium hydroxide 2.0 g) of a 2.5N sodium hydroxide solution to a room temperature or below, adding therein 0.1 g of hydrosulfite as an antioxidant and 3.0 g of 3,3'-dimethyl-4,4'-dihydroxybiphenyl, and fully dissolving these antioxidants.

The obtained reactant mixture was diluted with 500 mL of methylene chloride and 100 mL of water and cleaned. A lower layer was separated from the reactant mixture. Then, the reactant mixture was cleaned with 500 mL of water one time, with 500 mL of 0.03N hydrochloric acid one time, and with 500 mL of water three times in this order. The obtained methylene chloride solution was dropped into methanol with stirring. The obtained redeposit was filtered and dried to obtain a PC copolymer with a structure represented by the formula (PC-2). A viscosity average molecular weight (Mv) of the PC copolymer of this Example calculated in the same manner as in Example 5 was 62,000. A copolymerization ratio of the PC copolymer of this Example was calculated through analysis with reference to the $^1$H-NMR spectrum. Table 6 shows the results.

Respective average chain lengths (a1, a2) of the repetition components $Ar_1$, $Ar_2$ of the obtained PC copolymer were measured in the same manner as in Example 7. Table 6 shows the results.

Example 12

Methylene chloride (32 g) was added to the bischloroformate-composition-containing solution (44.8 g) of Example 1-12 to adjust the solid content concentration of the bischloroformate composition to 93 (g/L). To this solution, PTBP (0.055 g) was added as a terminal terminator and stirred for sufficient mixing. After a temperature inside the reactor was cooled down to 10 degrees C., an entire amount of the prepared divalent phenol solution was added to the obtained solution, to which 0.4 mL of a triethylamine aqueous solution (7 vol %) was added with stirring and kept on stirring for one hour.

As the above-described dihydric phenol solution, a solution was prepared by cooling 22 g (sodium hydroxide 2.0 g) of a 2.5N sodium hydroxide solution to a room temperature or below, adding therein 0.1 g of hydrosulfite as an antioxidant and 3.0 g of 3,3'-dimethyl-4,4'-dihydroxybiphenyl, and fully dissolving these antioxidants.

The obtained reactant mixture was diluted with 500 mL of methylene chloride and 100 mL of water and cleaned. A lower layer was separated from the reactant mixture. Then, the reactant mixture was cleaned with 500 mL of water one time, with 500 mL of 0.03N hydrochloric acid one time, and with 500 mL of water three times in this order. The obtained methylene chloride solution was dropped into methanol with stirring. The obtained redeposit was filtered and dried to obtain a PC copolymer with a structure represented by the formula (PC-2). A viscosity average molecular weight (Mv) of the PC copolymer of this Example calculated in the same manner as in Example 5 was 62,000. A copolymerization ratio of the PC copolymer of this Example was calculated through analysis with reference to the $^1$H-NMR spectrum. Table 6 shows the results.

Respective average chain lengths (a1, a2) of the repetition components $Ar_1$, $Ar_2$ of the obtained PC copolymer were measured in the same manner as in Example 7. Table 6 shows the results.

Comparative Example 3

Methylene chloride (22 g) was added to the bischloroformate-composition-containing solution (56.1 g) of Comparative Example 1 to adjust the solid content concentration of the bischloroformate composition to 90 (g/L). To this solution, PTBP (0.061 g) was added as a terminal terminator and stirred for sufficient mixing. After a temperature inside the reactor was cooled down to 10 degrees C., an entire amount of the prepared divalent phenol solution was added to the obtained solution, to which 0.4 mL of a triethylamine aqueous solution (7 vol %) was added with stirring and kept on stirring for one hour.

As the above-described dihydric phenol solution, a solution was prepared by cooling 22 g (sodium hydroxide 2.0 g) of a 2.5N sodium hydroxide solution to a room temperature or below, adding therein 0.1 g of hydrosulfite as an antioxidant and 3.0 g of 3,3'-dimethyl-4,4'-dihydroxybiphenyl, and fully dissolving these antioxidants.

The obtained reactant mixture was diluted with 500 mL of methylene chloride and 100 mL of water and cleaned. A lower layer was separated from the reactant mixture. Then, the reactant mixture was cleaned with 500 mL of water one time, with 500 mL of 0.03N hydrochloric acid one time, and with 500 mL of water three times in this order. The obtained methylene chloride solution was dropped into methanol with stirring. The obtained redeposit was filtered and dried to obtain a PC copolymer with a structure represented by the formula (PC-2). A viscosity average molecular weight (Mv) of the PC copolymer of this Comparative Example calculated in the same manner as in Example 5 was 62,000. A copolymerization ratio of the PC copolymer of this Comparative Example was calculated through analysis with reference to the $^1$H-NMR spectrum. Table 6 shows the results.

Respective average chain lengths (a1, a2) of the repetition components $Ar_1$, $Ar_2$ of the obtained PC copolymer were measured in the same manner as in Example 7. Table 6 shows the results.

Comparative Example 4

A PC copolymer of Comparative Example 4 was prepared in the same manner as that of Comparative Example 3 as disclosed in JP 2012-51983 A. A viscosity average molecular weight (Mv) of the PC copolymer of this Comparative Example calculated in the same manner as in Example 5 was 62,000. A copolymerization ratio of the PC copolymer of this Comparative Example was calculated through analysis with reference to the $^1$H-NMR spectrum. Table 6 shows the results.

Respective average chain lengths (a1, a2) of the repetition components $Ar_1$, $Ar_2$ of the obtained PC copolymer were measured in the same manner as in Example 7. Table 6 shows the results.

TABLE 6

| | $Ar_1$ | OCBP Ratio in Bischloroformate Composition (mol %) | a1 | $Ar_2$ | a2 | b | $Ar_2/(Ar_1 + Ar_2)$ |
|---|---|---|---|---|---|---|---|
| Ex. 6 | BisZ | 35 | 1.36 | OCBP | 1.93 | 36 | 0.59 |
| Ex. 7 | BisCZ | 40 | 1.22 | OCBP | 2.12 | 37 | 0.65 |
| Ex. 8 | BisZ | 32 | 1.27 | OCBP | 1.76 | 40 | 0.58 |
| Ex. 9 | BisZ | 29 | 1.37 | OCBP | 1.62 | 40 | 0.56 |
| Ex. 10 | BisCZ | 45 | 1.16 | OCBP | 2.28 | 35 | 0.68 |
| Ex. 11 | BisCZ | 50 | 1.17 | OCBP | 2.68 | 31 | 0.71 |
| Ex. 12 | BisCZ | 33 | 1.05 | OCBP | 1.78 | 42 | 0.63 |
| Comp. 3 | BisCZ | 60 | — | OCBP | — | — | Insoluble |
| Comp. 4 | BisCZ | — | 1.38 | OCBP | 2.79 | 21 | 0.67 |

As shown in Table 6, it has been demonstrated that the value of a2 can be reduced by reducing the molar composition ratio of $Ar_2$ when the average number of monomer units of bischloroformate composition (material) is 1.99 or less.

Evaluation 4: Evaluation of Solubility

The solubility of the PC copolymer of each of Examples 6 to 12 and Comparative Examples 3 to 4 was evaluated by the following method (1). Table 7 shows the results.

(1) In a screw-cap container with a Teflon™-made packing, 1 g of the PC copolymer was measured off and 9 g of methylene chloride was added. The container was sealed by screwing the cap. The container was then shaken at a room temperature (23 degrees C.) to dissolve the PC copolymer. After the container was left still for one day, the solubility of the PC copolymer was visually evaluated.

The solubility of the PC copolymer of each of Examples 6 to 10 and 12 and Comparative Examples 3 to 4 was evaluated by the following method (2). Table 8 shows the results.

(2) The solubility was evaluated in the same manner as in the method (1) except that 4 g of THF was used in place of the solvent (9 g of methylene chloride) of the above-described solubility evaluation (1).

The solubility of the PC copolymer of each of Examples 8 to 9 and 12 and Comparative Examples 3 to 4 was evaluated by the following method (3). Table 9 shows the results.

(3) In a screw-cap container with a Teflon™-made packing, 1 g of the resin was measured off and 1.5 g of THF was added. The container was sealed by screwing the cap. The container was left still for three hours at a room temperature (23 degrees C). The container was then opened to further add 2.5 g of THF therein and sealed again. After the container was shaken and left still for one day, the solubility was visually evaluated.

In evaluating the solubility, a solution "in which either a gel or an insoluble matter was found" (non-uniform) was ranked as G, a solution "uniformly dissolved and having a HAZE over 10%" (whitening) was ranked as F, and a solution "being uniform and having a HAZE below 10%" (transparent) was ranked as E.

Evaluation 5: Wear Resistance Evaluation

The wear resistance of the PC copolymer of each of Examples 6 to 12 and Comparative Examples 3 to 4 was evaluated. The wear resistance of the PC copolymer was evaluated as follows.

1. Preparation of Sample of PC Copolymer for Wear Resistance Evaluation

The PC copolymer (2 g) was dissolved in methylene chloride (12 mL) and the obtained solution was cast into film on a commercially available PET film using an applicator. This film was heated under reduced pressure and a solvent was removed to obtain a film sample having a thickness of about 30 μm.

2. Preparation of Sample of Photoreceptor for Wear Resistance Evaluation

The PC copolymer (1 g) and a compound (CTM-1) (1 g) represented by a formula (23) below were dissolved in methylene chloride (10 mL) and the obtained solution was cast into film on a commercially available PET film using an applicator. This film was heated under reduced pressure and a solvent was removed to obtain a film sample having a thickness of about 30 μm.

3. Evaluation

A wear resistance of a cast surface of each of the films prepared in [1] and [2] was evaluated using Suga Abrasion Tester NUS-ISO-3 (manufactured by Suga Test Instruments Co.,Ltd). A test was performed by bringing an abrasion paper (containing 3-μm-diameter alumina particles), to which a load of 9.8N was applied, into contact with a surface of the photosensitive layer and reciprocating the abrasion paper 2,000 times. A mass reduction (abrasion amount) was then measured. Table 7 shows the results.

[Formula 54]

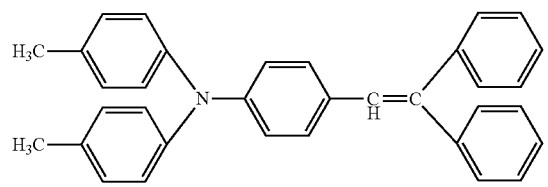

(23)

TABLE 7

| | Solubility Methylene Chloride | Abrasion Amount (mg) | |
|---|---|---|---|
| | (10 mass %) | Resin | Resin/CTM |
| Ex. 6 | E | 0.20 | 0.41 |
| Ex. 7 | E | 0.20 | 0.40 |
| Ex. 8 | E | 0.19 | 0.39 |
| Ex. 9 | E | 0.20 | 0.41 |
| Ex. 10 | E | 0.22 | 0.41 |
| Ex. 11 | F | 0.21 | 0.38 |
| Ex. 12 | E | 0.21 | 0.40 |
| Comp. 3 | G | — | — |
| Comp. 4 | G | — | — |

TABLE 8

| | Solubility THF (20 mass %) |
|---|---|
| Ex. 6 | E |
| Ex. 7 | E |
| Ex. 8 | E |
| Ex. 9 | E |
| Ex. 10 | F |
| Ex. 12 | E |
| Comp. 3 | G |
| Comp. 4 | G |

TABLE 9

| | Solubility THF (40 mass %→20 mass %) |
|---|---|
| Ex. 8 | F |
| Ex. 9 | E |
| Ex. 12 | E |
| Comp. 3 | G |
| Comp. 4 | G |

As shown in Tables 7 to 9, the PC copolymers of Examples have proven to be excellent in solubility as compared with the PC copolymers of Comparative Examples. In particular, the PC copolymer of Comparative Example 4 with a2 over 2.7 was insoluble even in methylene chloride, although the less soluble OCBP composition thereof was lower than that of the PC copolymer of Example 10.

Further, the PC copolymers of Examples have all proven to exhibit a good wear resistance.

It should be noted that the PC copolymers of Comparative Example 3 and Comparative Example 4 were insoluble in a solvent and thus respective samples thereof for wear resistance evaluation could not be prepared.

Production of Coating Liquid and Electrophotographic Photoreceptor

An aluminum film (film thickness: 50 μm) was used as a conductive substrate. A charge generating layer and a charge transporting layer were sequentially laminated on a surface of the conductive substrate to form a laminate sensitive layer, thus producing an electrophotographic photoreceptor. 0.5 g of oxotitanium phthalocyanine was used as a charge generating substance while 0.5 g of a butyral resin was used as a binder resin. The charge generating substance and the binder resin were added into 19 g of methylene chloride (solvent) and dispersed with a ball mill. Then, the dispersion was applied onto the surface of the conductive-substrate film using a bar coater and dried, thereby forming a charge generating layer having a film thickness of approximately 0.5 μm.

Next, 0.5 g of a compound (CTM-1) represented by the formula (23) (charge transporting substance) and 0.5 g of the PC copolymer of each of Examples 6 to 12 were dispersed in 10 mL of tetrahydrofuran to prepare a coating liquid. The coating liquid was applied onto the charge generating layer using an applicator and dried, thereby forming a charge transporting layer having a film thickness of approximately 20 μm.

The thus-obtained photoreceptor was stuck onto a 60-mm-diameter aluminum drum to demonstrate a good electrical conductivity between the aluminum drum and the photoreceptor.

Next, the electrophotographic photoreceptor stuck on the aluminum drum was evaluated in terms of electrophotographic performance using a static electrification tester CYNTHIA54IM (manufactured by GENTEC LTD.) in an EV mode with an initial charge amount of −700 V. As a result, each of the samples has been demonstrated to lower its surface potential in response to light irradiation (light attenuation), thus functioning as a photoreceptor (Table 10). In the above evaluation, a potential at the time of stoppage of potential change caused after sufficient exposure to light was evaluated as a "residual potential".

A residual potential of 50 V or less was ranked as H and a residual potential over 50 V was ranked as I. Table 10 shows the results.

TABLE 10

|  | Light Attenuation | Residual Potential |
|---|---|---|
| Ex. 6 | Yes | H |
| Ex. 7 | Yes | H |
| Ex. 8 | Yes | H |
| Ex. 9 | Yes | H |
| Ex. 10 | Yes | H |
| Ex. 11 | Yes | H |
| Ex. 12 | Yes | H |

As shown in Table 10, the electrophotographic photoreceptors containing the PC copolymers of Examples 6 to 12 have proven to exhibit good electrical characteristics.

The invention claimed is:

1. A polycarbonate resin that is represented by a formula (A1) below and has a molar composition ratio represented by $Ar_2/(Ar_1+Ar_2)$ ranging from 40 mol % to 75 mol % wherein the molar composition ratio means a mole percentage of a skeleton represented by $Ar_2$ with respect to the total mole percentage (100 mol %) of the skeleton represented by $Ar_1$ and a skeleton represented by $Ar_2$,

where:
- $Ar_1$ is a group represented by a formula (2) below;
- $Ar_2$ is a group represented by a formula (3) below;
- a1 represents an average chain length of the component $Ar_1$;
- a2 represents an average chain length of the component $Ar_2$; and
- a1 and a2 are each independently more than 1.0 but not more than 2.7,

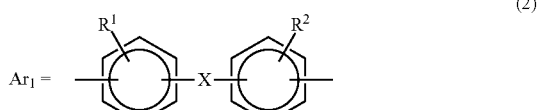

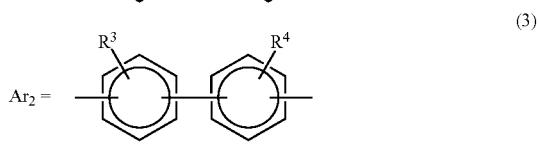

where:
- $R^1$ and $R^2$ in the formula (2) are each independently a hydrogen atom or a substituent, $R^1$ and $R^2$ as substituents being each independently selected from the group consisting of a trifluoromethyl group and an alkyl group having 1 to 3 carbon atoms;
- X is selected from the group consisting of —O—, —CO—, —S—, —SO$_2$—, —CR$^5$R$^6$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below;
- $R^5$ and $R^6$ are each independently a hydrogen atom or a substituent, $R^5$ and $R^6$ as substituents being each independently selected from the group consisting of an alkyl group having 1 to 5 carbon atoms, a trifluoromethyl group, and a substituted or unsubstituted aryl group having 6 to 12 carbon atoms; and
- $R^3$ and $R^4$ in the formula (3) are each independently selected from the group consisting of a perfluoroalkyl group having 1 to 3 carbon atoms and an alkyl group having 1 to 3 carbon atoms,

where R are each independently an aliphatic hydrocarbon group having 1 to 6 carbon atoms.

2. The polycarbonate resin according to claim 1, wherein a solution prepared by dissolving the polycarbonate resin in methylene chloride at a concentration of 10 mass % has a haze value of less than 10% measured according to JIS K 7105 at an optical path length of 10 mm; and a solution prepared by dissolving the polycarbonate resin in tetrahydrofuran at a concentration of 20 mass % has a haze value of less than 10% measured according to JIS K 7105 at an optical path length of 10 mm.

3. The polycarbonate resin according to claim 1, wherein when a solution prepared by dissolving the polycarbonate resin in tetrahydrofuran at a concentration of 40 mass % is left still at a temperature of 20 degrees C. to 28 degrees C. for three hours or more, added with tetrahydrofuran so that a solid content concentration of the polycarbonate resin reaches 20 mass %, and further dissolved by stirring and shaking at a temperature of 20 degrees C. to 28 degrees C. for five hours or more, the solution comprises neither gel component nor insoluble component and has a haze value of less than 10% measured according to JIS K 7105 at an optical path length of 10 mm.

4. A coating liquid comprising:
the polycarbonate resin according to claim 1; and
an organic solvent.

5. An electrophotographic photoreceptor comprising:
a substrate; and
a photosensitive layer on the substrate, the photosensitive layer comprising the polycarbonate resin according to claim 1.

6. The polycarbonate resin according to claim 1, wherein a1 in formula (A1) is more than 1.0 but not more than 1.99.

7. The polycarbonate resin according to claim 1, wherein the molar composition ratio represented by $Ar_2/(Ar_1+Ar_2)$ is from 59 mol % to 75 mol %.

8. The polycarbonate resin according to claim 1, wherein $Ar_1$ is 1,1-bis-(4-hydroxyphenyl)cyclohexane or 1,1-bis-(4-hydroxy-3-methylphenyl)cyclohexane, and $Ar_2$ is 3,3'-dimethyl-4,4'-dihydroxybiphenyl.

9. A polycarbonate resin that is represented by a formula (A2) below and has a molar composition ratio represented by $Ar_2/(Ar_1+Ar_2)$ ranging from 40 mol % to 75 mol % wherein the molar composition ratio means a mole percentage of a skeleton represented by $Ar_2$ with respect to the total mole percentage (100 mol %) of the skeleton represented by $Ar_1$ and a skeleton represented by $Ar_2$,

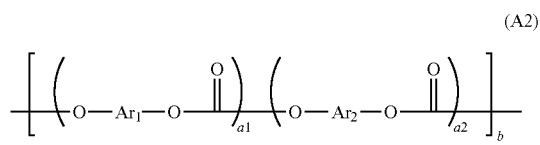

where:
$Ar_1$ is a group represented by a formula (2) below;
$Ar_2$ is a group represented by a formula (3) below;
a1 represents an average chain length of the component $Ar_1$;
a2 represents an average chain length of the component $Ar_2$;
a1 and a2 are each independently more than 1.0 but not more than 2.7;
b represents the number of repetitions of a unit in a square bracket; and (a1+a2)×b, which represents an average number of repetitions of the resin, is a value of 30 to 300,

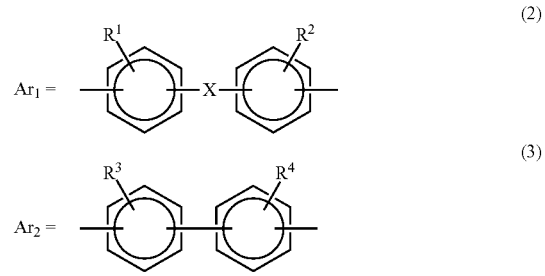

where:
$R^1$ and $R^2$ in the formula (2) are each independently a hydrogen atom or a substituent, $R^1$ and $R^2$ as substituents being each independently selected from the group consisting of a trifluoromethyl group and an alkyl group having 1 to 3 carbon atoms;
X is selected from the group consisting of —O—, —CO—, —S—, —SO$_2$—, —CR$^5$R$^6$—, a substituted or unsubstituted cycloalkylidene group having 5 to 12 carbon atoms, a substituted or unsubstituted adamantane-2,2-diyl group, a substituted or unsubstituted adamantane-1,3-diyl group, a substituted or unsubstituted α,ω-alkylene group having 2 to 12 carbon atoms, a 9,9-fluorenylidene group, a 1,8-menthanediyl group, a 2,8-menthanediyl group, and a group represented by a formula (100) below;
$R^5$ and $R^6$ are each independently a hydrogen atom or a substituent, $R^5$ and $R^6$ as substituents being each independently selected from the group consisting of an alkyl group having 1 to 5 carbon atoms, a trifluoromethyl group, and a substituted or unsubstituted aryl group having 6 to 12 carbon atoms;
$R^3$ and $R^4$ in the formula (3) are each independently selected from the group consisting of a perfluoroalkyl group having 1 to 3 carbon atoms and an alkyl group having 1 to 3 carbon atoms,

where R are each independently an aliphatic hydrocarbon group having 1 to 6 carbon atoms.

10. The polycarbonate resin according to claim 9, wherein a solution prepared by dissolving the polycarbonate resin in methylene chloride at a concentration of 10 mass % has a haze value of less than 10% measured according to JIS K 7105 at an optical path length of 10 mm; and a solution prepared by dissolving the polycarbonate resin in tetrahydrofuran at a concentration of 20 mass % has a haze value of less than 10% measured according to JIS K 7105 at an optical path length of 10 mm.

11. The polycarbonate resin according to claim 9, wherein when a solution prepared by dissolving the polycarbonate resin in tetrahydrofuran at a concentration of 40 mass % is left still at a temperature of 20 degrees C. to 28 degrees C. for three hours or more, added with tetrahydrofuran so that a solid content concentration of the polycarbonate resin reaches 20 mass %, and further dissolved by stirring and shaking at a temperature of 20 degrees C. to 28 degrees C. for five hours or more, the solution comprises neither gel component nor insoluble component and has a haze value of less than 10% measured according to JIS K 7105 at an optical path length of 10 mm.

12. A coating liquid comprising:
   the polycarbonate resin according to claim 9; and
   an organic solvent.

13. An electrophotographic photoreceptor comprising:
   a substrate; and
   a photosensitive layer on the substrate, the photosensitive layer comprising the polycarbonate resin according to claim 9.

14. The polycarbonate resin according to claim 9, wherein a1 in formula (A2) is more than 1.0 but not more than 1.99.

15. The polycarbonate resin according to claim 9, wherein the molar composition ratio represented by $Ar_2/(Ar_1+Ar_2)$ is from 59 mol % to 75 mol %.

16. The polycarbonate resin according to claim 9, wherein $Ar_1$ is 1,1-bis-(4-hydroxyphenyl)cyclohexane or 1,1-bis-(4-hydroxy-3-methylphenyl)cyclohexane, and $Ar_2$ is 3,3'-dimethyl-4,4'-dihydroxybiphenyl.

\* \* \* \* \*